US010844349B2

(12) United States Patent
Merkel et al.

(10) Patent No.: US 10,844,349 B2
(45) Date of Patent: Nov. 24, 2020

(54) ALBUMIN FORMULATION AND USE

(75) Inventors: Sandra Marie Merkel, Raleigh, NC (US); Luke Dimasi, Boston, MA (US); Collette Ann Sheahan, Birkenhead (AU); Philip Harvey Morton, Nottingham (GB)

(73) Assignee: Albumedix Ltd., Nottingham (GB)

( * ) Notice: Subject to any disclaimer, the term of this patent is extended or adjusted under 35 U.S.C. 154(b) by 0 days.

(21) Appl. No.: 14/130,639

(22) PCT Filed: Jul. 5, 2012

(86) PCT No.: PCT/US2012/045505
§ 371 (c)(1),
(2), (4) Date: Jan. 2, 2014

(87) PCT Pub. No.: WO2013/006675
PCT Pub. Date: Jan. 10, 2013

(65) Prior Publication Data
US 2014/0234966 A1 Aug. 21, 2014

Related U.S. Application Data

(60) Provisional application No. 61/504,406, filed on Jul. 5, 2011.

(30) Foreign Application Priority Data

Jul. 15, 2011 (EP) .................................... 11174267

(51) Int. Cl.
*C12N 5/00* (2006.01)
*C07K 14/76* (2006.01)
*C07K 14/435* (2006.01)
*C12N 5/0735* (2010.01)

(52) U.S. Cl.
CPC .......... *C12N 5/0018* (2013.01); *C07K 14/435* (2013.01); *C07K 14/76* (2013.01); *C12N 5/0606* (2013.01); *C12N 2500/30* (2013.01); *C12N 2501/998* (2013.01)

(58) Field of Classification Search
None
See application file for complete search history.

(56) References Cited

U.S. PATENT DOCUMENTS

| 5,692,649 | A | * | 12/1997 | Schwab | ..................... | 222/321.3 |
| 5,876,969 | A | | 3/1999 | Fleer et al. | | |
| 6,060,530 | A | * | 5/2000 | Chaouk et al. | .................. | 521/64 |
| 2003/0036637 | A1 | * | 2/2003 | Fulton | .................. | C07K 14/765 |
| | | | | | | 530/363 |
| 2008/0227202 | A1 | * | 9/2008 | Dancu | ......................... | 435/377 |
| 2009/0181102 | A1 | * | 7/2009 | Jorquera Nieto | .... | C07K 14/765 |
| | | | | | | 424/529 |
| 2010/0168000 | A1 | | 7/2010 | Kiessling | | |
| 2011/0009312 | A1 | * | 1/2011 | Rosen | ..................... | A61K 38/04 |
| | | | | | | 514/1.9 |
| 2012/0220530 | A1 | * | 8/2012 | Plumridge | ........... | C07K 14/765 |
| | | | | | | 514/15.2 |

FOREIGN PATENT DOCUMENTS

| CN | 1724567 A | 1/2006 | |
| CN | 101492493 A | 7/2009 | |
| EP | 0624195 B1 | 9/2004 | |
| EP | 2072056 A1 | 6/2009 | |
| JP | H04-504253 A | 7/1992 | |
| JP | 2002-542761 A | 12/2002 | |
| JP | 2009-137947 A | 6/2009 | |
| WO | WO 90/11091 * | 10/1990 | ........... A61K 39/395 |
| WO | 96/37515 A1 | 11/1996 | |
| WO | 1996-037515 A1 | 11/1996 | |
| WO | 99/011091 A1 | 3/1999 | |
| WO | 00/44772 A2 | 8/2000 | |
| WO | 2001/79271 A1 | 10/2001 | |
| WO | 2003/059934 A2 | 7/2003 | |
| WO | 2003/060071 A2 | 7/2003 | |
| WO | 2006/066595 A2 | 6/2006 | |
| WO | WO 2008/009641 * | 1/2008 | ............... C12N 5/02 |
| WO | 2010/092135 A2 | 8/2010 | |
| WO | 2012/059486 A1 | 5/2012 | |

OTHER PUBLICATIONS

Sigma Product Information, retrieved from the internet, Dec. 16, 2014: https://www.sigmaaldrich.com/content/dam/sigma-aldrich/docs/Sigma/Formulation/m0769for.pdf.*
Sigma Albumin, Product Information, retrieved from the internet:http://www.sigmaaldrich.com/content/dam/sigma-aldrich/docs/Sigma-Aldrich/Product_Information_Sheet/a7284pis.pdf.*
Tarelli et al., Recombinant Human Albumin as a Stabilizer for Biological Materials and for the Preparation of International Reference Reagents, Biologicals (1998) vol. 26, pp. 331-346.*
ZLB Behring AG package insert, Human Albumin 20% Behring Low Salt, retrieved from the internet, Nov. 3, 2015: www.old.health.gov.il/units/pharmacy/trufot/alonim/2752.pdf.*
Gencore sequence search, conducted Nov. 5, 2015, pp. 1-42.*
Boye et al., Interactions Involved in the Gelation of Bovine Serium Albumin, J. Agric. Food Chem., 1996, vol. 44, pp. 996-1004.*
Peters et al., All About Albumin, 1995, Chapter 7, pp. 285-318; retrieved from the internet: https://ac.els-cdn.com/B9780125521109500052/3-s2.0-B9780125521109500052-main.pdf?_tid=48eeb563-2a08-48b2-ae5d-f94941789036&acdnat=1541187309_e4c5bde64e7ece71bc1dbd5acf134875.*

(Continued)

*Primary Examiner* — Scott Long
*Assistant Examiner* — Evelyn Y Pyla
(74) *Attorney, Agent, or Firm* — McCarter & English, LLP; Yu Lu

(57) ABSTRACT

The invention relates to a new formulation of albumin, a method for producing the albumin formulation and to uses of the albumin formulation, for example in cell culture such as mammalian cell culture and particularly in stem cell culture.

19 Claims, 12 Drawing Sheets
Specification includes a Sequence Listing.

(56) References Cited

OTHER PUBLICATIONS

Arakawa et al, 2000, Biochim et Biophys Acta 1479, 32-36.
Francis, 2010, Cytotechnol 62, 1-16.
Hosseini et al, 2002, Iranian Biomedical J 6(4), 135-140.
Lonza, 2011, Product Sheet—Dulbecco Phosphate Buffer Saline.
Matejtschuk et al, 2000, Br J Anaesth 85(6), 887-895.
Novozymes Formulation and Drug Delivery Using Human Serum Albumin Powerpoint presentation (2012).
Sigma, 2008, Product Catalogue 135-137.
Stange et al, 2011, Liver Transpl 17, 705-709.
Dulbecco 2009, http://cshprotocols.cshlp.org/content/2009/3/pdb.rec11725.full?text_only=true.
Dulbecco 2013, HiMedia Cell Culture Enabling Breakthroughs, TS1119.
Svedberg et al., "The PH-stability regions of serum albumin and of serum globulin," J Am Chem Soc. 52(7): 2855-63 (1930).
Product information a6909 Albumin, Human 1996 sigma-aldrich Jun. 8, 2016 (3 pages).
Dulbecco's Phosphate Buffered Saline (DPBS) 2007. Retrieved on 2011: <biocenter.hu/pdf/dpbs.pdf> (1 page).
Anraku et al., "Stabilizing mechanisms in commercial albumin preparations: octanoate and N-acetyl-L-tryptophanate protect human serum albumin against heat and oxidative stress," Biochim Biophys Acta. 1702(1):9-17 (2004).
Holmes et al., "Site specific 1:1 opioid:albumin conjugate with in vitro activity and long in vivo duration," Bioconjug Chem. 11(4): 439-44 (2000).
Chruszcz et al., Serum albumins-unusual allergens. Biochim Biophys Acta. Dec. 2013;1830(12):5375-81.
Kragh-Hansen et al., Practical aspects of the ligand-binding and enzymatic properties of human serum albumin. Biol Pharm Bull. Jun. 2002;25(6):695-704.
Pandjaitan et al., *Escherichia coli* expression and purification of recombinant dog albumin, a cross-reactive animal allergen. J Allergy Clin Immunol. Feb. 2000;105(2 Pt 1):279-85.

\* cited by examiner

FIG. 9

| Fatty Acid | Average FA Content | | | |
|---|---|---|---|---|
| Lipid No. | mg/mL | %wt | mM | % mol |
| C6:0 | 0.001 | 0.039 | 0.01 | 0.09 |
| C8:0 | 0.033 | 1.268 | 0.23 | 2.36 |
| C9:0 | 0.000 | 0.000 | 0.00 | 0.00 |
| C10:0 | 0.001 | 0.039 | 0.01 | 0.06 |
| C11:0 | 0.000 | 0.000 | 0.00 | 0.00 |
| C12:0 | 0.011 | 0.429 | 0.05 | 0.58 |
| C13:0 | 0.000 | 0.000 | 0.00 | 0.00 |
| C14:0 | 0.229 | 8.933 | 1.00 | 10.51 |
| C14:1 | 0.001 | 0.039 | 0.00 | 0.05 |
| C15:0 | 0.010 | 0.390 | 0.04 | 0.43 |
| C15:1 | 0.000 | 0.000 | 0.00 | 0.00 |
| C16:0 | 0.866 | 33.762 | 3.38 | 35.37 |
| C16:1n7 | 0.024 | 0.917 | 0.09 | 0.97 |
| C16:2n4 | 0.000 | 0.000 | 0.00 | 0.00 |
| C16:3n4 | 0.013 | 0.488 | 0.05 | 0.52 |
| C17:0 | 0.014 | 0.527 | 0.05 | 0.52 |
| C17:1 | 0.000 | 0.000 | 0.00 | 0.00 |
| C18:0 | 0.584 | 22.762 | 2.05 | 21.49 |
| C18:1n7 | 0.005 | 0.195 | 0.02 | 0.19 |
| C18:1n9c | 0.227 | 8.836 | 0.80 | 8.40 |
| C18:1n9t | 0.049 | 1.892 | 0.17 | 1.80 |
| C18:2n6c | 0.118 | 4.603 | 0.42 | 4.41 |
| C18:2n6t | 0.000 | 0.000 | 0.00 | 0.00 |
| C18:3n3 | 0.000 | 0.000 | 0.00 | 0.00 |
| C18:4n3 | 0.000 | 0.000 | 0.00 | 0.00 |
| C19:0 | 0.000 | 0.000 | 0.00 | 0.00 |
| C20:0 | 0.187 | 7.275 | 0.60 | 6.25 |
| C20:1n9 | 0.000 | 0.000 | 0.00 | 0.00 |
| C20:2n6 | 0.001 | 0.020 | 0.00 | 0.02 |
| C20:3n3 | 0.000 | 0.000 | 0.00 | 0.00 |
| C20:3n6 | 0.001 | 0.020 | 0.00 | 0.02 |
| C20:4n6 | 0.000 | 0.000 | 0.00 | 0.00 |
| C20:5n3 | 0.000 | 0.000 | 0.00 | 0.00 |
| C22:0 | 0.194 | 7.568 | 0.57 | 5.97 |
| C22:1n11 | 0.000 | 0.000 | 0.00 | 0.00 |
| C22:1n9 | 0.000 | 0.000 | 0.00 | 0.00 |
| C22:2n6 | 0.000 | 0.000 | 0.00 | 0.00 |
| Sum | 2.564 | 100.000 | 9.543 | 100.00 |

FIG. 10

| Metal | Conc (mg/kg solution) |
|---|---|
| Silver | <0.5 |
| Aluminium | <0.5 |
| Arsenic | <0.5 |
| Boron | <0.5 |
| Barium | <0.5 |
| Beryllium | <0.5 |
| Bismuth | <0.5 |
| Calcium | 2.6 |
| Cadmium | <0.5 |
| Cobalt | <0.5 |
| Chromium | <0.5 |
| Copper | <0.5 |
| Iron | <0.5 |
| Gallium | <0.5 |
| Indium | <0.5 |
| Potassium | 1 |
| Lithium | <0.5 |
| Magnesium | <0.5 |
| Manganese | <0.5 |
| Molybdenum | <0.5 |
| Nickel | <0.5 |
| Phosphorus | 2.6 |
| Lead | <0.5 |
| Palladium | <0.5 |
| Platinum | <0.5 |
| Antimony | <0.5 |
| Selenium | <0.5 |
| Silicon | <0.5 |
| Tin | <0.5 |
| Strontium | <0.5 |
| Titanium | <0.5 |
| Thallium | <0.5 |
| Vanadium | <0.5 |
| Zinc | <0.5 |
| Zirconium | <0.5 |

ALBUMIN FORMULATION AND USE

CROSS-REFERENCE TO RELATED APPLICATIONS

This application is a 35 U.S.C. 371 national application of PCT/US2012/045505 filed Jul. 5, 2012, which claims priority or the benefit under 35 U.S.C. 119 of European application no. 11174267.2 filed Jul. 15, 2011 and U.S. provisional application no. 61/504,406 filed Jul. 5, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

The invention relates to a new formulation of albumin and to uses of the albumin formulation.

Albumin is the most abundant protein in plasma. Albumin has been described and characterized from a large number of mammals and birds. Albumin is believed to have a role in maintaining correct osmotic pressure and it also has a role in transport of various compounds in the blood stream. Albumin is a protein which is used to treat patients with severe burns, shock or blood loss. It is also used as an excipient for pharmacologically active compounds, many of which need to be stabilized for example to reduce the formation of soluble aggregates and/or insoluble aggregates of albumin. Furthermore, albumin is used to supplement media used for growing higher eukaryotic cells, including stem cells. Albumin fusion proteins are a fusion of a protein to albumin, or to a variant or fragment thereof, and may increase or decrease the half-life of the protein, for example increased in vivo half-life. Conjugation partners, e.g. proteins or chemicals, can be conjugated to albumin to increase or decrease the half-life of the conjugation partner, for example increased in vivo half-life. At present albumin is obtained from blood products, such as serum, or produced recombinantly in microorganisms such as yeast (e.g. WO 96/37515, WO 2000/044772) or from transgenic plants or animals. Typically, albumin is purified from the production source in order to provide a product which is sufficiently pure to meet the user's needs and/or to achieve a high yield of product. In some technical areas, such as cell culture or pharmaceuticals, there is a desire for products to be substantially free or completely free of animal derived components.

Purified albumin in a final liquid form is relatively unstable (compared to albumin in solid form) and so in order to maximize its shelf life it is either lyophilized and/or stabilizers added to the final liquid formulation. However, lyophilization can add significantly to the overall cost of the preparation and can be inconvenient to the end user who would need to resuspend the lyophilized product if they need a liquid product. For the preferred liquid product, stabilizers that are commonly added to albumin are n-acetyl-tryptophan, octanoic acid (octanoate, caprylate) and/or polysorbate 80 (e.g. Tween®). The albumin of WO 2000/044772 is stabilized by octanoic acid. Arakawa & Kita (2000) discloses stabilizing effects of caprylate and acetyltryptophanate on heat-induced aggregation of bovine serum albumin (*Biochimica et Biophysica Acta* 1479: 32-36). Hosseini et al. (2002) discloses a study of the heat-treated human albumin stabilization by caprylate and acetyltryptophanate (*Iranian Biomedical Journal* 6(4): 135-140).

The present inventors have identified that octanoic acid, can be deleterious to mammalian cell culture particularly to stem cell culture. Furthermore, polysorbate 80 (Tween®) can be deleterious to mammalian cell culture. What is required is a stable liquid formulation of albumin which is not deleterious to mammalian cell culture.

SUMMARY OF THE INVENTION

The invention provides a liquid formulation of albumin with improved stability, where stability is shown, for example, as a reduced level of soluble aggregates of albumin or insoluble aggregates of albumin in the formulation. The invention also provides methods using the formulation and uses of the formulation, such as mammalian culture and particularly stem cell culture.

BRIEF DESCRIPTION OF THE FIGURES

FIG. 9 shows a fatty acid profile of an albumin formulation according to the invention.

FIG. 10 shows a metal ion profile, by ICP-OES, of an albumin formulation according to the invention.

DETAILED DESCRIPTION OF THE INVENTION

Definitions

Figure 1:
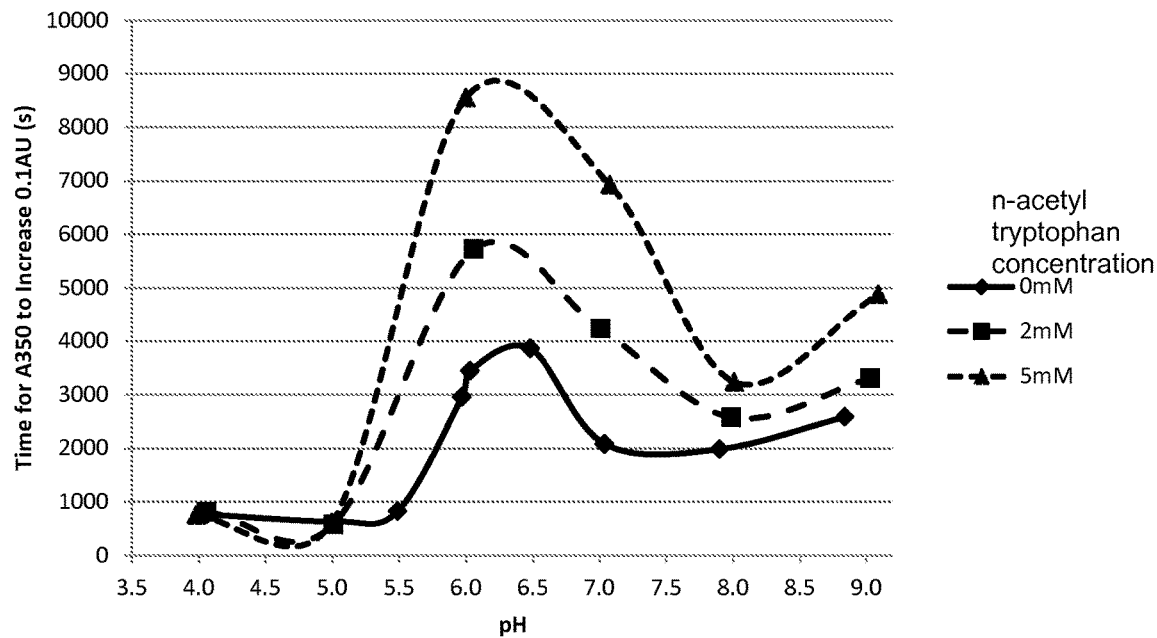
FIG. 1 shows the effect of pH and n-acetyl tryptophan concentration on the stability of albumin compositions (10 mg/mL), as determined by the time taken (seconds) for the absorbance (A350) to increase by 0.1 Absorbance Units (AU), a measure of visible (insoluble) aggregates.
Figure 2:
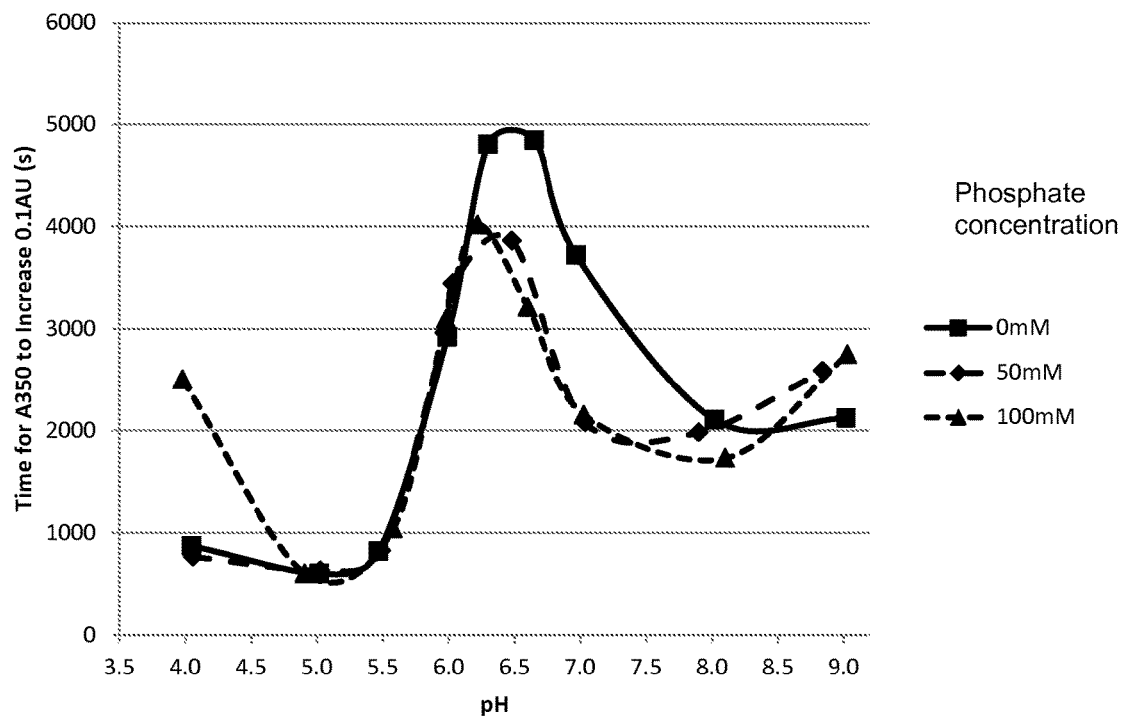
FIG. 2 shows the effect of pH and phosphate concentration on the stability of albumin compositions (10 mg/mL), as determined by the time taken (seconds) for the absorbance (A350) to increase by 0.1 AU.
Figure 3:
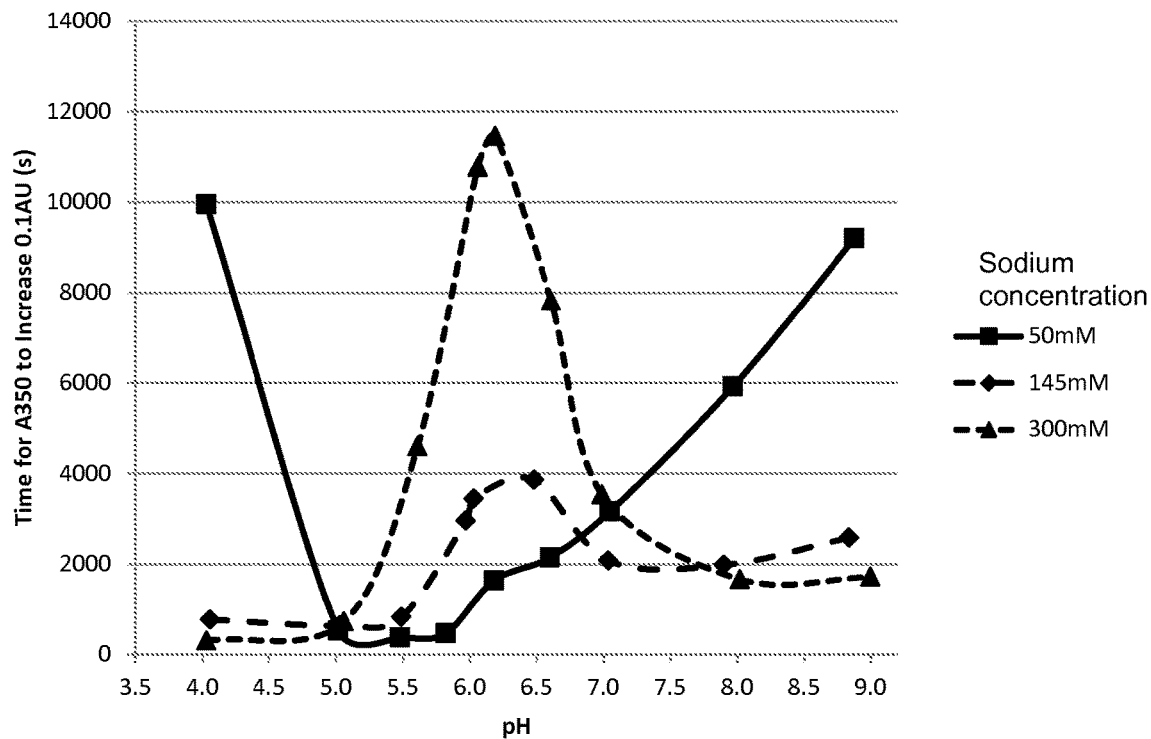
FIG. 3 shows the effect of pH and sodium concentration on the stability of albumin compositions (10 mg/mL), as determined by the time taken (seconds) for the absorbance (A350) to increase by 0.1 AU.

The terms "cell culture medium", "culture medium" and "medium formulation" refer to a nutritive solution for culturing or growing cells.

A "serum-free" medium is a medium that contains no serum (e.g., fetal bovine serum (FBS), horse serum, goat serum, or any other animal-derived serum known to one skilled in the art).

The term "basal medium" refers to any medium which is capable of supporting growth of cells. The basal medium supplies standard inorganic salts, such as zinc, iron, magnesium, calcium and potassium, as well as trace elements, vitamins, an energy source, a buffer system, and essential amino acids. Suitable basal media include, but are not limited to Alpha Minimal Essential Medium (.alpha.MEM); Basal Medium Eagle (BME); Basal Medium Eagle with Earle's BSS; DME/F12; DMEM high Glucose with L-Glutamine; DMEM high glucose without L-Glutamine; DMEM:F12 1:1 with L-Glutamine; Dulbecco's Modified Eagle's Medium (DMEM); F-10; F-12; Glasgow's Minimal Essential Medium (G-MEM); G-MEM with L-glutamine; Grace's Complete Insect Medium; Grace's Insect Medium without FBS; Ham's F-10 with L-Glutamine; Ham's F-12 with L-Glutamine; IMDM with HEPES and L-Glutamine; IMDM with HEPES and without L-Glutamine; IPL-41 Insect Medium; Iscove's Modified Dulbecco's Medium.; L-15 (Leibovitz) without L-Glutamine; L-15 (Leibovitz) (2×) without L-Glutamine or Phenol Red; McCoy's 5A Modified Medium; Medium 199; MEM Eagle without L-Glutamine or Phenol Red (2×); MEM Eagle-Earle's BSS with L-glutamine; MEM Eagle-Earle's BSS without L-Glutamine; MEM Eagle-Hanks BSS without L-Glutamine; Minimal Essential Medium (MEM); Minimal Essential Medium-alpha. (MEM-alpha); NCTC-109 with L-Glutamine; Richter's CM Medium with L-Glutamine; RPMI 1640; RPMI 1640 with L-Glutamine; RPMI 1640 without L-Glutamine; RPMI 1640 with HEPES, L-Glutamine and/or Penicillin-Streptomycin; Schneider's Insect Medium; or any other media known to one skilled in the art. Preferred basal media for stem cell culture include MEF, DMEM, CTS, and DMEM/F-12.

The term "albumin" means a protein having the same and/or very similar tertiary structure as human serum albumin (HSA) or HSA domains and has similar properties of HSA or the relevant domains. Similar tertiary structures are for example the structures of the albumins from the species mentioned under parent albumin. Some of the major properties of albumin are i) its ability to regulate of plasma volume, ii) a long plasma half-life of around 19 days±5 days, iii) ligand-binding, e.g. binding of endogenous molecules such as acidic, lipophilic compounds including bilirubin fatty acids, hemin and thyroxine (see also Table 1 of Kragh-Hansen et al, 2002, Biol. Pharm. Bull. 25, 695, hereby incorporated by reference), iv) binding of small organic compounds with acidic or electronegative features e.g. drugs such as warfarin, diazepam, ibuprofen and paclitaxel (see also Table 1 of Kragh-Hansen et al, 2002, Biol. Pharm. Bull. 25, 695, hereby incorporated by reference). Not all of these properties need to be fulfilled to in order to characterize a protein or fragment as an albumin. If a fragment, for example, does not comprise a domain responsible for binding of certain ligands or organic compounds the variant of such a fragment will not be expected to have these properties either. The term albumin includes variants, and/or derivatives such as fusions and/or conjugations of an albumin or of an albumin variant.

The term "variant" means a polypeptide derived from a parent albumin comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The altered polypeptide (variant) can be obtained through human intervention by modification of the polynucleotide sequence encoding the parental albumin. The variant albumin is preferably at least 70%, preferably at least 75%, more preferably at least 80%, more preferably at least 85%, even more preferably at least 90%, most preferably at least 95%, at least 96%, at least 97%, at least 98%, at least 99%, or 100% identical to SEQ ID NO: 2 and maintains at least one of the major properties of the parent albumin or a similar tertiary structure as HSA. For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows: (Identical Residues×100)/(Length of Alignment−Total Number of Gaps in Alignment).

The variant may possess altered binding affinity to FcRn and/or an altered rate of transcytosis across endothelia, epithelia and/or mesothelia mono cell-layer when compared to the parent albumin. The variant polypeptide sequence is preferably one which is not found in nature. A variant includes a fragment, e.g. comprising or consisting of at least 100, 150, 200, 250, 300, 350, 450, 500, 550 contiguous amino acids of an albumin.

The term "wild-type" (WT) albumin means an albumin having the same amino acid sequence as the albumins naturally found in an animal or in a human being. SEQ ID NO: 2 is an example of a wild-type albumin from *Homo sapiens*.

The term "parent" or "parent albumin" means an albumin to which an alteration is made to produce the albumin variants which may be used in the present invention. The parent may be a naturally occurring (wild-type) polypeptide or an allele thereof or a variant thereof such as a variant described in PCT/EP2010/066572 or a variant or derivative described in PCT/EP2011/055577.

The term "fusion" means a genetic fusion of albumin (or a variant or fragment thereof) and a non-albumin protein. The non-albumin protein may be a therapeutic, prophylactic, or diagnostic protein. Examples of albumin fusions are provided in EP 624195, WO 2001/079271, WO 2003/059934, WO 2003/060071, WO 2011/051489, PCT/EP11/055,577 and EP 11164955 (incorporated herein by reference in their entirety).

The term "conjugation" means an albumin (or a variant or fragment or fusion thereof) to which a non-albumin moiety is chemically conjugated. The non-albumin moiety may be a therapeutic, prophylactic, or diagnostic protein. Examples of albumin conjugations are provided in PCT/EP11/055,577 and EP 11164955 (incorporated herein by reference in their entirety).

The term "suspension culture" refers to cells in culture in which the majority or all of cells in culture are present in suspension, and the minority or none of the cells in the culture vessel are attached to the vessel surface or to another surface within the vessel (adherent cells). The "suspension culture" can have greater than about 50%, 60%, 65%, 75%, 85%, or 95% of the cells in suspension, not attached to a surface on or in the culture vessel.

The term "adherent culture" refers to cells in culture in which the majority or all of cells in culture are present attached to the vessel surface or to another surface within the vessel, and the minority or none of the cells in the culture vessel are in suspension. The "adherent culture" can have greater than 50%, 60%, 65%, 75%, 85%, or 95% of the cells adherent.

As used herein, the term "mammal" includes any human or non-human mammal, including but not limited to porcine, ovine, bovine, rodents, ungulates, pigs, sheep, lambs, goats, cattle, deer, mules, horses, primates (such as monkeys), dogs, cats, rats, and mice.

The term "cell" includes any cell such as, but not limited to, any human or non-human mammalian cell as described herein. A cell may be a normal cell or an abnormal cell (e.g. transformed cells, established cells, or cells derived from diseased tissue samples). The cell may be a somatic cell such as a fibroblast or keratinocyte. Preferred cells are stem cells such as, but not limited to, embryonic stem cells, fetal stem cells, adult stem cells and pluripotent stem cells such as induced pluripotent stem cells. Particularly preferred cells are human embryonic stem cells, human fetal stem cells, human adult stem cells and human pluripotent stem cells such as induced human pluripotent stem cells.

A first aspect of the invention provides a composition comprising albumin, a solvent, at least 175 mM cations, having a pH from about 5.0 to about 9.0 and wherein the composition comprises equal to or less than 30 mM octanoate. An advantage of such a composition is that this formulation provides an albumin which is sufficiently stable to have a useful shelf-life and is not deleterious to the health of mammalian cells (e.g. it is not toxic) when the composition is used in mammalian cell culture.

It is preferred that the composition contains anions to balance the cations.

The solvent may be an inorganic solvent such as water or an inorganic buffer such as a phosphate buffer such as sodium phosphate, potassium phosphate, or an organic buffer such as sodium acetate or sodium citrate. The buffer may stabilize pH. Sodium phosphate (e.g. $NaH_2PO_4$) is a preferred pH buffer, such as pH 5.0, 5.5, 6.0, 6.5, 7.0, 7.5, 8.0.

The inventors have observed that octanoate is deleterious to mammalian cells in cell culture. Therefore, the composition comprises low levels of octanoate. For example, it is preferred that the composition comprises less than 30 mM octanoate, more preferably less than about 28, 26, 24, 22, 20, 18, 16, 15, 14, 12, 10, 8 mM octanoate, even more preferably less than about 6, 5, 4, 3 mM octanoate, most preferably less than about 2, 1, 0.5, 0.4, 0.3, 0.2, 0.1, 0.01, or 0.001 mM octanoate. It is preferred that the composition is substantially free of octanoate. That is, it is preferred that the level of octanoate in the composition is not sufficient to cause a deleterious effect on cells during culture, for example mammalian cells (particularly stem cells such as human stem cells) in cell culture such as in vitro cell culture. Most preferably the composition is free of octanoate (0 mM octanoate).

Preferred parameters for fatty acids are provided below. The fatty acid content is preferably an average of multiple samples, for example 2, 3, 4 or 5 samples:

| Fatty Acid | Preferred range (mM) |
| --- | --- |
| C6:0 | ≤0.1 mM, more preferably ≤0.01 mM, most preferably 0 mM |
| C8:0 | ≤2.5 mM, more preferably ≤0.23 mM, most preferably 0 mM |
| C9:0 | ≤0.1 mM, more preferably ≤0.01 mM, most preferably 0 mM |
| C10:0 | ≤0.1 mM, more preferably ≤0.01 mM, most preferably 0 mM |
| C11:0 | ≤0.1 mM, more preferably ≤0.01 mM, most preferably 0 mM |
| C12:0 | ≤0.5 mM, more preferably ≤0.05 mM, most preferably 0 mM |
| C13:0 | ≤0.1 mM, more preferably ≤0.01 mM, most preferably 0 mM |
| C14:0 | ≤10 mM, more preferably 1 ≤mM, most preferably 0 mM |
| C14:1 | ≤0.1 mM, more preferably ≤0.01 mM, most preferably 0 mM |
| C15:0 | ≤0.4 mM, more preferably ≤0.04 mM, most preferably 0 mM |
| C15:1 | ≤0.1, more preferably ≤0.01 mM, most preferably 0 mM |

-continued

| Fatty Acid | Preferred range (mM) |
|---|---|
| C16:0 | ≤34 mM, more preferably ≤3.38 mM, most preferably 0 mM |
| C16:1n7 | ≤0.9 mM, more preferably ≤0.09 mM, most preferably 0 mM |
| C16:2n4 | ≤0.1 mM, more preferably ≤0.01 mM, most preferably 0 mM |
| C16:3n4 | ≤0.5 mM, more preferably ≤0.05 mM, most preferably 0 mM |
| C17:0 | ≤0.5 mM, more preferably ≤0.05 mM, most preferably 0 mM |
| C17:1 | ≤0.1, more preferably ≤0.01 mM, most preferably 0 mM |
| C18:0 | ≤20 mM, more preferably ≤2.05 mM, most preferably 0 mM |
| C18:1n7 | ≤0.2 mM, more preferably ≤0.02 mM, most preferably 0 mM |
| C18:1n9c | ≤8 mM, more preferably ≤0.8 mM, most preferably 0 mM |
| C18:1n9t | ≤1.7 mM, more preferably ≤0.17 mM, most preferably 0 mM |
| C18:2n6c | ≤4.2 mM, more preferably ≤042 mM, most preferably 0 mM |
| C18:2n6t | ≤0.1 mM, more preferably ≤0.01 mM, most preferably 0 mM |
| C18:3n3 | ≤0.1 mM, more preferably ≤0.01 mM, most preferably 0 mM |
| C18:4n3 | ≤0.1 mM, more preferably ≤0.01 mM, most preferably 0 mM |
| C19:0 | ≤0.1 mM, more preferably ≤0.01 mM, most preferably 0 mM |
| C20:0 | ≤6 mM, more preferably ≤0.6 mM, most preferably 0 mM |
| C20:1n9 | ≤0.1 mM, more preferably ≤0.01 mM, most preferably 0 mM |
| C20:2n6 | ≤0.1 mM, more preferably ≤0.01 mM, most preferably 0 mM |
| C20:3n3 | ≤0.1 mM, more preferably ≤0.01 mM, most preferably 0 mM |
| C20:3n6 | ≤0.1 mM, more preferably ≤0.01 mM, most preferably 0 mM |
| C20:4n6 | ≤0.1 mM, more preferably ≤0.01 mM, most preferably 0 mM |
| C20:5n3 | ≤0.1 mM, more preferably ≤0.01 mM, most preferably 0 mM |
| C22:0 | ≤5.7 mM, more preferably ≤0.57 mM, most preferably 0 mM |
| C22:1n11 | ≤0.1 mM, more preferably ≤0.01 mM, most preferably 0 mM |
| C22:1n9 | ≤0.1 mM, more preferably ≤0.01 mM, most preferably 0 mM |
| C22:2n6 | ≤0.1 mM, more preferably ≤0.01 mM, most preferably 0 mM |

It is also preferred that the overall fatty acid content of the composition is less than or equal to 20 mM, more preferably less than or equal to 15, 10, 5, 4, 3, 2 or 1 mM. It is more preferred that the composition is substantially free of fatty acids, more preferably free of fatty acids.

A fatty acid profile and a metal ion profile of an albumin formulation comprising 100 g·L$^{-1}$ albumin, ≤1 mM octanoate, 250 mM Na$^+$ and having a pH of about 6.5 are provided in FIGS. 9 and 10, respectively. These are particularly preferred profiles. The albumin composition may comply with one or both of the profiles of FIG. 9 and FIG. 10.

It is preferred that the cations are present from at least about 175 mM, for example from at least about 200, 225, 250, 275, 300, 325, 350, 375, 400, 425, 450, 475, 500, 525, 550, 575, 600, 650, 700, 750, 800, 850, 900, 950, 1000 mM. Preferred maximum cation concentrations include 1000, 950, 900, 850, 800, 750, 700, 650, 600, 575, 550, 525, 500, 475, 450, 425, 400, 375, 350, 325, 300, 275 and 250 mM. Preferred cation concentrations include 200 to 500 mM. More preferred is a cation concentration of about 200 to 350 mM. Most preferred is a cation concentration of about 250 mM.

The pH of the composition may be between about 5.0 and about 9.0, for example from about 5.0, 5.25, 5.5, 5.75, 6.0, 6.25, 6.5, 6.75, 7.0, 7.25, 7.5, 7.75, 8.0, 8.25, or 8.5 to about 5.5, 5.75, 6.0, 6.25, 6.5, 6.75, 7.0, 7.25, 7.5, 7.75, 8.0, 8.25, 8.5, 8.75 or 9.0. It is preferred that pH is from about 5.0 to 8.0, such as from about 6.0 to about 8.0, more preferably from about 6.0 to about 7.0 or 6.0 to 6.5. Most preferred the pH is about 6.5.

The cations of the composition may be provided by any cation and may be provided by one or more (several) classes or species as described below. For example, the cations may be either mono or bivalent, monoatomic or polyatomic and may be provided by one or more (several) of an alkali metal (such as sodium, potassium), an alkaline earth metal (such as calcium, magnesium) or ammonium. It is preferred that the cations are provided by sodium and/or potassium and/or magnesium, most preferably sodium or magnesium.

Cations may be provided by a salt of an inorganic acid (e.g. a group 1 or 2 metal or ammonium salt such as sodium chloride), a salt of a divalent acid (e.g. a group 1 or group 2 metal or ammonium sulphate or phosphate such as sodium sulphate) or a salt of an organic acid (e.g. a group 1 or group 2 metal or ammonium salt of acetate or citrate such as sodium acetate).

Cations and anions used to stabilize the albumin may be provided by (i) salts and/or (ii) pH buffers such as described herein. Therefore, there may be more than one (several) species of cation or anion, such as 2, or 3 species. There may be more than one (several) source of a single cation, for example Na which may be provided by both a pH buffer (such as sodium phosphate) and a salt (such as NaCl).

Anions useful to the invention include inorganic anions such as phosphate, and halides such as chloride, and organic anions such as acetate and citrate. Anions may be either mono or bivalent, monoatomic or polyatomic. Preferred anions include sulphate, acetate phosphate and chloride, particularly chloride, sulphate and acetate.

Therefore, the composition may comprise one or more (several) of an alkali metal phosphate or chloride (such as sodium phosphate, potassium phosphate, sodium chloride or potassium chloride), an alkaline earth metal phosphate (such as calcium phosphate, magnesium phosphate, calcium chloride, magnesium chloride) or ammonium phosphate or ammonium chloride.

The composition may have an overall ionic strength of at least 175 mmol·L$^{-1}$. For example, from about 175 to 1000 mmol·L$^{-1}$ such as from about 175, 200, 225, 250, 275, 300, 325, 350, 375, 400, 425, 450, 475, 500, 525, 550, 575, 600, 650, 700, 750, 800, 850, 900, 950, 1000 mmol·L$^{-1}$ to about 1000, 950, 900, 850, 800, 750, 700, 650, 600, 575, 550, 525, 500, 475, 450, 425, 400, 375, 350, 325, 300, 275, 250 mmol·L$^{-1}$. More preferred is an overall ionic strength of about 200 to 350 mmol·L$^{-1}$. Most preferred is an ionic strength of about 250 mmol·L$^{-1}$.

The inventors have realized that the presence of stabilizers such as detergents (e.g. polysorbate 80 (Tween®)) can be deleterious to mammalian cells in cell culture. Therefore, it is preferred that the composition comprises less than 20 mg·L$^{-1}$ detergent (e.g. polysorbate 80), preferably less than 15, 10, 5, 4, 3, 2, 1, 0.5, 0.1, 0.01, 0.001 mg·L$^{-1}$ detergent (e.g. polysorbate 80). Even more preferably, the composition is substantially free of detergent (e.g. polysorbate 80). That is, it is preferred that the level of detergent (e.g. polysorbate 80) in the composition is not sufficient to cause a deleterious effect on cells during culture, for example mammalian cells (particularly stem cells such as human stem cells) in cell culture such as in vitro cell culture. Most preferably the composition is free of detergent (e.g. polysorbate 80). Detergent (e.g. polysorbate 80) levels can be assayed by techniques known to the skilled person for example, but not limited to, the assay disclosed in WO 2004/099234 (incorporated herein by reference).

For some cell media, it is preferred that the media is substantially free or free of tryptophan (e.g. tryptophan-free RPMI 1640 as disclosed by Lee et al., 2002, *Immunology* 107(4): 452-460). An albumin composition may be added to a medium. Therefore, in order to maintain the tryptophan free character of a medium, an albumin composition which has low levels of amino acids (e.g. N-acetyl tryptophan), is substantially free of amino acids (e.g. N-acetyl tryptophan) or is free of amino acids (e.g. N-acetyl tryptophan) is useful. Therefore, it is preferred that the albumin composition comprises less than 5 mM amino acids (e.g. N-acetyl tryptophan), preferably less than 4, 3, 2, 1, 0.5, 0.1, 0.01, 0.005, 0.001 mM amino acids (e.g. N-acetyl tryptophan). Even more preferably, the composition is substantially free of amino acids (e.g. N-acetyl tryptophan). That is, it is preferred that the level of amino acids (e.g. N-acetyl tryptophan) in the composition is not sufficient to cause a deleterious effect on cells during culture, for example mammalian cells (particularly stem cells such as human stem cells) in cell culture such as in vitro cell culture. Most preferably the composition is free of amino acids (e.g. N-acetyl tryptophan).

It is even more preferred that the composition is substantially free of, or completely free of, octanoate, amino acids (e.g. N-acetyl tryptophan) and detergent (e.g. polysorbate 80).

In order to identify whether or not there is a deleterious or toxic effect of the albumin formulation on cell culture, a test may be carried out by preparing a first cell culture medium containing the albumin formulation of the invention and preparing one or more (several) control cell culture media and monitoring their effect on cell lines. A control cell culture medium is identical to the first cell culture medium except that the albumin formulation of the invention is replaced with another albumin formulation, e.g. an albumin formulation stabilized with octanoate, a detergent (e.g. polysorbate 80) and/or an amino acid (e.g. n-acetyl tryptophan). The test media and controls may be used to cultivate one or more (several) cell lines (e.g. a cell line as described herein) and the effect of the albumin on the cells monitored e.g. by monitoring cell growth, cell morphology and/or cell differentiation. It is preferred that the test is carried out over multiple passages of the cell line, e.g. at least 2, 3, 4, 5, 6, 7, 8, 9 or 10 passages. Suitable methods are known in the art. It is preferred that the albumin formulation of the present invention is less toxic or deleterious to cells than an albumin stabilized with higher levels of octanoate, detergent or amino acids. For example, a medium comprising the albumin composition of the invention may show at least a 2-, 5-, 10-, 100-, 1000-, 10000-, or 100000-fold improvement over a control medium comprising another albumin formulation, e.g. an albumin formulation stabilized with octanoate, a detergent (e.g. polysorbate 80) and/or an amino acid (e.g. n-acetyl tryptophan). The 2, 5, 10, 100, 1000, 10000, or 100000-fold improvement may relate to viable cell numbers, correct or healthy cell morphology and/or to the number or relative number of differentiated cells, particularly cells showing differentiation to a desired cell class or type.

It is preferred that the stability of the albumin composition is higher than that of equivalent albumin in water or in 150 mM Na. One method to compare stability, particularly related to the formation of insoluble aggregates of albumin, is:

i) place an aliquot (e.g. 1 mL) of the albumin composition in a cuvette (e.g. a polystyrene cuvette, such as Sarstedt 10×4×45 mm);

ii) place the cuvette in a temperature controlled spectrophotometer that has been pre-equilibrated and controlled at a desired temperature, e.g. 65° C.;

iii) Monitor/measure the absorbance of the composition at 350 nm, referenced against an empty cuvette over a desired time period (e.g. 2 hours) by taking a reading at defined intervals (e.g. every 18 seconds)

iv) Process the data by taking the first several (e.g. seven) data points, average the data point readings and subtract this data point from all data points in order to provide base absorbance values of around 0.

v) Determine and/or record the time taken for the processed absorbance values to increase by 0.1 AU (Absorbance Units) above this baseline.

It is preferred that stability analysis is performed in duplicate.

It is preferred that the stability of the albumin composition of the invention is sufficiently high so that the time taken for the measured absorbance to increase by 0.1 AU above the baseline (according to the above described test carried out at 65° C.), compared to a control solution of albumin at the same concentration in a solvent such as 150 mM Na or water and measured under the same conditions is at least 10% better. It is more preferred that the stability is at least 20, 30, 40, 50, 60, 70, 80, 90 or 100% better.

An alternative or additional stability test, particularly for the formation of soluble aggregates of albumin, is to monitor the formation of soluble albumin polymer by GP-HPLC over time at a set temperature. One suitable stability study with measurement by GP HPLC includes:

i) Placing 10 mL sterilely (e.g. by filtration through a sterile 0.22 µm filter) of each sample to be investigated into sterile vials (e.g. baked 10 mL glass vials) which are then stoppered (e.g. with a sterile butyl rubber seal and optionally over-sealed).

ii) A T0 sample of ~200 µL is then taken and the vial is incubated at a specified temperature (e.g. placed in a water bath that is set at a specified temperature (e.g. at 40° C.)).

iii) Samples (~200 µL) are then taken from each of the vials after certain time points (e.g. 14 days).

iv) injecting an aliquot (e.g. 25 µL) of the albumin sample taken out of the vial (at <50 mg/mL) onto a GP-HPLC column (e.g. 7.8 mm id×300 mm length TSK G3000SWXL column, (Tosoh Bioscience), with a 6.0 mm id×40 mm length TSK SW guard column (Tosoh Bioscience));

v) chromatographing the aliquot in a suitable buffer (e.g. 25 mM sodium phosphate, 100 mM sodium sulphate, 0.05% (w/v) sodium azide, pH 7.0) at a suitable speed (e.g. 1 mL/min)

vi) monitoring the chromatograph procedure e.g. by UV detection at 280 nm;

vii) quantifying one or more (several), or all, of monomer, dimer, trimer and polymer content of the aliquot as % (w/w) by identifying their respective peak area relative to the total peak area.

It is preferred that the test is carried out in triplicate.

Therefore, the invention also provides an albumin composition having a stability as defined in one or both of the above mentioned tests, and a method for producing an albumin composition including one or both of the above mentioned tests.

Albumin has been described and characterized from a large number of mammals and birds (e.g. albumins listed in WO 2010/092135 (particularly Table 1) and PCT/EP11/055, 577 (particularly page 9 and SEQ ID NO: 2, 4-19 and 31), both incorporated herein by reference in their entirety).

The composition of the invention may comprise one or more (several) albumins. Preferably the composition comprises an albumin selected from human albumin (e.g. AAA98797 or P02768-1, SEQ ID NO: 2 (mature), SEQ ID NO: 3 (immature)), non-human primate albumin, (such as chimpanzee albumin (e.g. predicted sequence XP_517233.2 SEQ ID NO: 4), gorilla albumin or macaque albumin (e.g. NP_001182578, SEQ ID NO: 5), rodent albumin (such as hamster albumin (e.g. A6YF56, SEQ ID NO: 6), guinea pig albumin (e.g. Q6WDN9-1, SEQ ID NO: 7), mouse albumin (e.g. AAH49971 or P07724-1 Version 3, SEQ ID NO: 8, or the mature sequence SEQ ID NO: 19) and rat albumin (e.g. AAH85359 or P02770-1 Version 2, SEQ ID NO: 9))), bovine albumin (e.g. cow albumin P02769-1, SEQ ID NO: 10), equine albumin such as horse albumin (e.g. P35747-1, SEQ ID NO: 11) or donkey albumin (e.g. Q5XLE4-1, SEQ ID NO: 12), rabbit albumin (e.g. P49065-1 Version 2, SEQ ID NO: 13), goat albumin (e.g. ACF10391, SEQ ID NO: 14), sheep albumin (e.g. P14639-1, SEQ ID NO: 15), dog albumin (e.g. P49822-1, SEQ ID NO: 16), chicken albumin (e.g. P19121-1 Version 2, SEQ ID NO: 17) and pig albumin (e.g. P08835-1 Version 2, SEQ ID NO: 18). Mature forms of albumin are particularly preferred and the skilled person is able to identify mature forms using publicly available information such as protein databanks and/or by using signal peptide recognition software such as SignalP (e.g., SignalP (Nielsen et al., 1997, *Protein Engineering* 10:1-6)). SignalP Version 4.0 is preferred (Petersen et al., 2011, *Nature Methods* (8): 785-786).

Human albumin as disclosed in SEQ ID NO: 2 or any naturally occurring allele thereof, is the preferred albumin of the albumin composition according to the invention. SEQ ID NO: 2 may be encoded by the nucleotide sequence of SEQ ID NO: 1.

The albumin, particularly the human albumin, may be a variant, or a derivative such as fusion of conjugation of an albumin or of an albumin variant. It is preferred that the albumin has at least 70% identity to HSA (SEQ ID NO: 2), more preferably at least 72, 73, 75, 80, 85, 90, 95, 96, 97, 98, 99, 99.5% identity to HSA. The albumin variant may have one or more point (several) mutations, e.g. K573P, K573Y, K573W, K500A compared to a parent albumin such as those provided in the sequence listing, particularly SEQ ID NO: 2 (mutations are described in relation to SEQ ID NO: 2 and the skilled person can identify equivalent mutations in other albumins by aligning an albumin sequence against SEQ ID NO: 2 using the EMBOSS software described herein). For an albumin having about 70 to 80% identity to SEQ ID NO: 2 (such as mouse albumin e.g. SEQ ID NO: 19), it is more preferred that the cation is present from at least 250 mM.

It is preferred that the albumin is present in the composition at a concentration of from about 1 $g \cdot L^{-1}$ to about 400 $g \cdot L^{-1}$. For example, the concentration may be from about 1, 5, 10, 25, 50, 75, 100, 125, 150, 175, 200, 225, 250, 275 $g \cdot L^{-1}$ to about 5, 10, 25, 50, 75, 100, 125, 150, 175, 200, 225, 250, 275, 300, 325, 350, 375 or 400 $g \cdot L^{-1}$. It is preferred that the concentration of albumin is from about 50 $g \cdot L^{-1}$ to about 200 $g \cdot L^{-1}$ Advantageously, the composition may comprise a recombinant albumin. That is, the albumin may be sourced from a recombinant organism such as a recombinant microorganism, recombinant plant or recombinant animal. Since some users prefer animal-free ingredients, it is more preferred that the albumin is sourced from a non-animal recombinant source, such as a recombinant microorganism or recombinant plant. Preferred microorganisms include prokaryotes and, more preferably, eukaryotes such as animals, plants, fungi or yeasts, for example, but not limited to, the following species in which albumins have been successfully expressed as recombinant proteins:

fungi (including but not limited to *Aspergillus* (WO 2006/066595), *Kluyveromyces* (Fleer, 1991, *Bio/technology* 9: 968-975), *Pichia* (Kobayashi, 1998, *Therapeutic Apheresis* 2: 257-262) and *Saccharomyces* (Sleep, 1990, *Bio/technology* 8: 42-46)), bacteria (Pandjaitab, 2000, *J. Allergy Clin. Immunol.* 105: 279-285)), animals (Barash, 1993, *Transgenic Research* 2: 266-276)

plants (including but not limited to potato and tobacco (Sijmons, 1990, *Bio/technology* 8: 217 and Farran, 2002, *Transgenic Research* 11: 337-346) and rice e.g. *Oryza sativa*)

mammalian cells such as CHO and HEK.

All citations are incorporated herein by reference in their entirety.

The albumin of the invention is preferably produced recombinantly in a suitable host cell. Non-animal host cells are preferred. A preferred host is yeast, preferably selected among *Pichia* or Saccharomycacae, more preferred *Saccharomyces cerevisiae*.

A preferred composition comprises 50 to 250 $g \cdot L^{-1}$ albumin, 200 to 300 mM $Na^+$, 20 to 30 mM phosphate, comprises less than 2 mM octanoate and has a pH between about 6.0 and 7.0. A particularly preferred composition comprises 50 to 150 $g \cdot L^{-1}$ albumin, 225 to 275 mM $Na^+$, 20 to 30 mM phosphate, comprises less than 1 mM octanoate and has a pH of about 6.5.

Another aspect of the invention provides a composition comprising albumin, a solvent, at least 175 mM cations, having a pH from about 5.0 to about 8.0 or 9.0. An advantage of such a composition is that this formulation provides an albumin which is sufficiently stable to have a useful shelf-life and is not deleterious to the health of mammalian cells when the composition is used in mammalian cell culture. Preferred parameters for the solvent, cations, ionic strength, and pH are the same as those disclosed in relation to the first aspect of the invention.

The albumin composition according to the invention may be provided in a flexible polymeric container, such as a bag. Suitable container volumes include from about 50 mL to about 10 000 mL, e.g. 50 mL, 1000 mL, 5000 mL and 10 000 mL. It is preferred that the container comprises one or more (several) inlets or outlets to allow filling of the container and/or dispensing from the bag. The albumin composition may be sterilized, e.g. prior to or after being filled in the container.

The production of recombinant albumin is known in the art and numerous hosts such as *Escherichia coli* (EP 73,646), yeast has been reported in WO 00/44772, EP 0683233 A2, and U.S. Pat. No. 5,612,196, and *Bacillus subtillis* (Saunders et al., 1987, *J. Bacteriol.* 169: 2917-2925), *Aspergillus*. Production of albumin has been demonstrated in transgenic plants such as but not limited to tobacco, rice, and maize and in transgenic animals such as but not limited to chicken and bovine.

A second aspect of the invention provides a cell culture medium comprising a composition as described herein and a basal medium. The cell culture medium may, for example, be for the culture of mammalian cells such as human cells. The cell culture medium may, for example, be for the culture of stem cells or of gametes or of embryos for example cell culture for assisted reproductive technology (ART) purposes.

It is preferred that the cell culture medium is substantially free of animal-derived components. It is more preferred that the cell culture medium is free of animal-derived components. In this context, 'animal-derived' component means a component which has been obtained from an animal. It does not include a component which is identical or substantially identical to an animal-derived component but which, instead of being obtained from an animal, is obtained as a recombinant component from a non-animal. A non-animal includes a plant, such as rice, a microorganism such as a yeast or bacterium.

Examples of cell culture media in which the albumin formulation may be used include those described in WO 2008/009641 (incorporated herein by reference in its entirety).

A cell culture medium comprising the albumin formulation of the first aspect of the invention may or may not comprise one or more (several) fatty acids, such as provided by a fatty acid supplement. Fatty acid supplements are commercially available, e.g. F7050 Fatty Acid Supplement (Animal-component free, liquid, sterile-filtered, suitable for cell culture) available from Sigma-Aldrich.

A third aspect of the invention relates to use of an albumin formulation, composition or cell culture medium as described herein to culture cells, such as cells described with reference to the second aspect of the invention and or described below the fifth aspect of the invention.

A fourth aspect of the invention relates to a method of culturing cells comprising incubating cells in a culture medium as described herein. The cells may be the cells described with reference to the second aspect of the invention and or described below the fifth aspect of the invention.

A fifth aspect of the invention relates to use of the albumin formulation of the first aspect of the invention in pharmaceutical products. Therefore, the invention also provides a pharmaceutical composition comprising the albumin formulation and an active pharmaceutical ingredient (API).

A sixth aspect of the invention relates to the use of a high cation concentration to stabilize albumin, e.g. from at least 175 mM cations as described for the first aspect of the invention.

The compositions and media of the present invention may be used to culture a variety of cells. In one embodiment, the medium is used to culture eukaryotic cells such as plant and/or animal cells. The cells can be mammalian cells, fish cells, insect cells, amphibian cells or avian cells. The medium can be used to culture cells selected from the group consisting of MK2.7 cells, PER-C6 cells, NS0, GS-NS0, CHO cells, HEK 293 cells, COS cells and Sp2/0 cells. MK2.7 (ATCC Catalogue Number CRL 1909) is an anti-murine VCAM IgGl expressing Hybridoma cell line derived from the fusion of a rat splenocyte and a mouse Sp2/0 myeloma. MK2.7 is a non-adherent cell line that can be grown in serum-free media. Other types of cells can be selected from the group consisting of 5L8 hybridoma cells, Daudi cells, EL4 cells, HeLa cells, HL-60 cells, K562 cells, Jurkat cells, THP-1 cells, Sp2/0 cells; and/or the hybridoma cells listed in Table 2, WO 2005/070120 which is hereby incorporated by reference or any other cell type disclosed herein or known to one skilled in the art.

Preferred cells includes stem cells such as but not limited to, embryonic stem cells, fetal stem cells, adult stem cells and pleuripotent stem cells such as induced pleuripotent stem cells. Particularly preferred cells are human embryonic stem cells, human fetal stem cells, human adult stem cells and human pleuripotent stem cells such as induced human pleuripotent stem cells. The cell line may be derived from a blastocyst. The cell line may test positive for one or more (several) of the following cell markers: POU5F1 (OCT-4), SSEA-3, SSEA-4, TRA1-60, TRA1-81, ALPL, telomerase activity, and/or hES-Cellect™ (Cellartis AB, Gothenburg Sweden). The cell line may test negative for cell marker ALPL and/or SSEA-1. Particularly preferred cell lines include SA121 and SA181 (Cellartis AB, Gothenburg, Sweden).

Additional mammalian cell types can include, but are not limited to, including primary epithelial cells (e.g. keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 91 1 cells, CRFK cells, MDCK cells, CHO cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI2650 cells, SW-13 cells, T24 cells, WI-28 VA13, 2RA cells, WISH cells, BS-C-I cells, LLC-PK.sub.2 cells, Clone M-3 cells, 1-10 cells, RAG cells, TCMK-1 cells, Y-1 cells, LLC-PK.sub.1 cells, PK(15) cells, GH.1 cells, GH3 cells, L2 cells, LLC-RC 256 cells, MH.sub.IC1 cells, XC cells, MDOK cells, VSW cells, and TH-1, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-2 1 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl.sub.1 cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDM.sub.IC3 cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntjac cells, SIRC cells, CII cells, and Jensen cells, or derivatives thereof).

Cells include cancer cells such, but not limited to, the following cancer cell lines: human myeloma (e.g., KMM-1, KMS-11, KMS-12-PE, KMS-12-BM, KMS-18, KMS-20, KMS-21-PE, U266, RPMI8226); human breast cancer (e.g., KPL-1, KPL-4, MDA-MB-231, MCF-7, KPL-3C, T47D, SkBr3, HS578T, MDA4355, Hs 606 (CRL-7368), Hs 605.T (CRL-7365) HS 742.T (CRL-7482), BT-474, HBL-100, HCC202, HCC1419, HCC1954, MCF7, MDA-361 MDA-436, MDA-453, SK-BR-3, ZR-75-30, UACC-732, UACC-812, UACC-893, UACC-3133, MX-1 and EFM-192A); ductal (breast) carcinoma (e.g., HS 57HT (HTB-126), HCC1008 (CRL-2320), HCC1954 (CRL-2338; HCC38 (CRL-2314), HCC1143 (CRL-2321), HCC1187 (CRL-2322), HCC1295 (CRL-2324), HCC1599 (CRL-2331), HCC1937 (CRL-2336), HCC2157 (CRL-2340), HCC2218 (CRL-2343), Hs574.T (CRL-7345), Hs 742.T (CRL-7482); skin cancer (e.g., COLO 829 (CRL-1974), TE 354.T (CRL-7762), Hs 925.T (CIU-7677)); human prostate cancer (e.g., MDA PCa 2a and MDA PCa 2b); bone cancer (e.g., Hs 919.T (CRL-7672), Hs 821.T (CRL-7554), Hs 820.T (CRL-7552)y HS 704.T (CRL-7444), HS 707(A).T (CRL-7448), HS 735.T (CRL-7471), HS 860.T (CRL-7595)y HS 888.T (CRL-7622); HS 889.T (CRL-7626); HS 890.T (CRL-7628), Hs 709.T (CRL-7453)); human lymphoma (e.g., K562); human cervical carcinoma (e.g., HeLA); lung carcinoma cell lines (e.g., H125, H522, H1299, NCI-H2126 (ATCC CCL-256), NCI-H1672 (ATCC CRL-5886), NCl-2171 (CRL-5929); NCI-H2195 (CRL05931); lung adenocarcinoma (e.g., NCI-H1395 (CRL-5856), NCI-H1437 (CRL-5872), NCI-H2009 (CRL-5911), NCI-H2122 (CRL-5985), NCI-H2087 (CRL-5922); metastatic lung cancer (e.g., bone) (e.g., NCI-H209 (HTB-172); colon carcinoma cell lines (e.g., LN235, DLD2, Colon A, LIM2537, LIM1215, LIM1863, LIM1899, LIM2405, LIM2412, SK-CO1 (ATCC HTB-77), HT29 (ATCC HTB38), LoVo (ATCC CCL-229), SW1222 (ATCC HB-11028), and SW480 (ATCC CCL-228); ovarian cancer (e.g., OVCAR-3 (ATCC HTB-161) and SKOV-3 (ATCC HTB-77); mesothelioma (e.g., NCl-h2052 (CRL-5915); neuroendocrine carcinoma (e.g., HCl—H1770 (e.g., CRL-5893); gastric cancer (e.g., LIM1839); glioma (e.g., T98, U251, LN235); head and neck squamous cell carcinoma cell lines (e.g., SCC4, SCC9 and SCC25); medulloblastoma (e.g., Daoy, D283 Med and D341 Med); testicular non-seminoma (e.g., TERA1); prostate cancer (e.g., 178-2BMA, Du145, LNCaP, and PC-3). Other cancer cell lines are well known in the art.

The media disclosed herein can be used to culture cells in suspension or adherent cells. The media of the present invention are suitable for adherent, monolayer or suspension culture, transfection, and/or cultivation of cells, and for expression of proteins or antibodies in cells in monolayer or suspension culture.

Cell culture can be performed using various culture devices, for example, a fermenter type tank culture device, an air lift type culture device, a culture flask type culture device, a spinner flask type culture device, a microcarrier type culture device, a fluidized bed type culture device, a hollow fiber type culture device, a roller bottle type culture device, a packed bed type culture device or any other suitable device known to one skilled in the art.

The present invention is further described by the following examples that should not be construed as limiting the scope of the invention.

EXAMPLES

Example 1

Effect of n-Acetyl-Tryptophan, Phosphate Concentration and Sodium Concentration on the Stability of Albumin Aim:

Previous work indicated that monitoring the formation of insoluble aggregates at 65° C., through an increase in absorption at 350 nm, is a valid method for screening of the effect of different formulation (composition) parameters on the stability of albumin. Since octanoate and polysorbate 80 appear to be detrimental to stem cell growth, it is preferred that an albumin formulation is substantially free of these components. This Example analyzes the effect of pH, sodium ion and buffer concentration on the stability of albumin. A common stabilizer for albumin is n-acetyl-tryptophan, therefore it is included in this Example as a test constituent.

Method:

Albumin at 100 mg/mL in 145 mM NaCl (albumin batch 1401) was diluted to 10 mg/mL according to Table 3. The buffers used for dilution are shown in Tables 1 and 2.

TABLE 1

| | rHSA Conc (g/L) | Na Molarity (mM) | Tryptophan Molarity (mM) |
|---|---|---|---|
| rHSA solution (1401) | 100 | 154 | |
| 5M NaCl | | 5000 | |
| Tryptophan | | 501 | 500 |

TABLE 2

| Buffer Stock Solution | Phosphate (mM) | Na (mM) |
|---|---|---|
| 0.5M Phosphate pH 4 | 502 | 500 |
| 0.5M Phosphate pH 5 | 500 | 518 |
| 0.5M Phosphate pH 6 | 500 | 634 |
| 0.5M Phosphate pH 7 | 500 | 851 |
| 0.5M Phosphate pH 8 | 500 | 970 |
| 0.5M Phosphate pH 9 | 500 | 992 |

TABLE 3

| | Stock Volumes to Add (mL) | | | | | |
|---|---|---|---|---|---|---|
| Sample | rHSA | Sodium Phosphate | NaCl | Tryptophan | Water | Actual pH |
| pH 4, 145 mM Sodium, 50 mM Phosphate | 0.500 | 0.498 | 0.080 | 0.000 | 3.922 | 4.06 |
| pH 5, 145 mM Sodium, 50 mM Phosphate | 0.500 | 0.500 | 0.078 | 0.000 | 3.922 | 5.03 |
| pH 6, 145 mM Sodium, 50 mM Phosphate | 0.500 | 0.500 | 0.066 | 0.000 | 3.934 | 6.03 |
| pH 7, 145 mM Sodium, 50 mM Phosphate | 0.500 | 0.500 | 0.045 | 0.000 | 3.956 | 7.04 |

TABLE 3-continued

| Sample | Stock Volumes to Add (mL) | | | | | Actual pH |
|---|---|---|---|---|---|---|
| | rHSA | Sodium Phosphate | NaCl | Tryptophan | Water | |
| pH 8, 145 mM Sodium, 50 mM Phosphate | 0.500 | 0.500 | 0.033 | 0.000 | 3.967 | 7.90 |
| pH 9, 145 mM Sodium, 50 mM Phosphate | 0.500 | 0.500 | 0.030 | 0.000 | 3.970 | 8.84 |
| pH 5.5, 145 mM Sodium, 50 mM Phosphate | 0.500 | 0.500 | 0.078 | 0.000 | 3.922 | 5.49 |
| pH 6, 145 mM Sodium, 50 mM Phosphate | 0.500 | 0.500 | 0.066 | 0.000 | 3.934 | 5.97 |
| pH 6.5, 145 mM Sodium, 50 mM Phosphate | 0.500 | 0.500 | 0.066 | 0.000 | 3.934 | 6.48 |
| pH 4, 145 mM Sodium, 50 mM Phosphate, 5 mM Tryptophan | 0.500 | 0.498 | 0.075 | 0.050 | 3.877 | 3.98 |
| pH 5, 145 mM Sodium, 50 mM Phosphate, 5 mM Tryptophan | 0.500 | 0.500 | 0.073 | 0.050 | 3.877 | 5.00 |
| pH 6, 145 mM Sodium, 50 mM Phosphate, 5 mM Tryptophan | 0.500 | 0.500 | 0.061 | 0.050 | 3.889 | 6.00 |
| pH 7, 145 mM Sodium, 50 mM Phosphate, 5 mM Tryptophan | 0.500 | 0.500 | 0.039 | 0.050 | 3.911 | 7.08 |
| pH 8, 145 mM Sodium, 50 mM Phosphate, 5 mM Tryptophan | 0.500 | 0.500 | 0.028 | 0.050 | 3.922 | 8.01 |
| pH 9, 145 mM Sodium, 50 mM Phosphate, 5 mM Tryptophan | 0.500 | 0.500 | 0.025 | 0.050 | 3.925 | 9.09 |
| pH 4, 145 mM Sodium, 50 mM Phosphate, 2 mM Tryptophan | 0.500 | 0.498 | 0.078 | 0.020 | 3.904 | 4.06 |
| pH 5, 145 mM Sodium, 50 mM Phosphate, 2 mM Tryptophan | 0.500 | 0.500 | 0.076 | 0.020 | 3.904 | 5.01 |
| pH 6, 145 mM Sodium, 50 mM Phosphate, 2 mM Tryptophan | 0.500 | 0.500 | 0.064 | 0.020 | 3.916 | 6.06 |
| pH 7, 145 mM Sodium, 50 mM Phosphate, 2 mM Tryptophan | 0.500 | 0.500 | 0.042 | 0.020 | 3.938 | 7.01 |
| pH 8, 145 mM Sodium, 50 mM Phosphate, 2 mM Tryptophan | 0.500 | 0.500 | 0.031 | 0.020 | 3.949 | 7.99 |
| pH 9, 145 mM Sodium, 50 mM Phosphate, 2 mM Tryptophan | 0.500 | 0.500 | 0.028 | 0.020 | 3.952 | 9.03 |
| pH 4, 50 mM Sodium, 25 mM Phosphate | 0.500 | 0.249 | 0.010 | 0.000 | 4.241 | 4.03 |
| pH 5, 50 mM Sodium, 25 mM Phosphate | 0.500 | 0.250 | 0.009 | 0.000 | 4.241 | 5.02 |
| pH 6, 50 mM Sodium, 25 mM Phosphate | 0.500 | 0.250 | 0.003 | 0.000 | 4.247 | 5.82 |
| pH 7, 50 mM Sodium, 25 mM Phosphate | 0.500 | 0.250 | 0.000 | 0.000 | 4.250 | 7.05 |
| pH 8, 50 mM Sodium, 25 mM Phosphate | 0.500 | 0.250 | 0.000 | 0.000 | 4.250 | 7.97 |
| pH 9, 50 mM Sodium, 25 mM Phosphate | 0.500 | 0.250 | 0.000 | 0.000 | 4.250 | 8.88 |
| pH 5.5, 50 mM Sodium, 25 mM Phosphate | 0.500 | 0.250 | 0.009 | 0.000 | 4.241 | 5.48 |
| pH 6, 50 mM Sodium, 25 mM Phosphate | 0.500 | 0.250 | 0.003 | 0.000 | 4.247 | 6.18 |
| pH 6.5, 50 mM Sodium, 25 mM Phosphate | 0.500 | 0.250 | 0.003 | 0.000 | 4.247 | 6.60 |
| pH 4, 300 mM Sodium, 25 mM Phosphate | 0.500 | 0.249 | 0.260 | 0.000 | 3.991 | 4.03 |
| pH 5, 300 mM Sodium, 25 mM Phosphate | 0.500 | 0.250 | 0.259 | 0.000 | 3.991 | 5.06 |
| pH 6, 300 mM Sodium, 25 mM Phosphate | 0.500 | 0.250 | 0.253 | 0.000 | 3.997 | 6.06 |
| pH 7, 300 mM Sodium, 25 mM Phosphate | 0.500 | 0.250 | 0.242 | 0.000 | 4.008 | 6.99 |
| pH 8, 300 mM Sodium, 25 mM Phosphate | 0.500 | 0.250 | 0.236 | 0.000 | 4.014 | 8.02 |

TABLE 3-continued

| Sample | rHSA | Sodium Phosphate | NaCl | Tryptophan | Water | Actual pH |
|---|---|---|---|---|---|---|
| pH 9, 300 mM Sodium, 25 mM Phosphate | 0.500 | 0.250 | 0.235 | 0.000 | 4.015 | 9.00 |
| pH 5.5, 300 mM Sodium, 25 mM Phosphate | 0.500 | 0.250 | 0.259 | 0.000 | 3.991 | 5.61 |
| pH 6, 300 mM Sodium, 25 mM Phosphate | 0.500 | 0.250 | 0.253 | 0.000 | 3.997 | 6.19 |
| pH 6.5, 300 mM Sodium, 25 mM Phosphate | 0.500 | 0.250 | 0.253 | 0.000 | 3.997 | 6.61 |
| pH 4, 145 mM Sodium, 0 mM Phosphate | 0.500 | 0.000 | 0.130 | 0.000 | 4.370 | 4.05 |
| pH 5, 145 mM Sodium, 0 mM Phosphate | 0.500 | 0.000 | 0.130 | 0.000 | 4.370 | 5.02 |
| pH 6, 145 mM Sodium, 0 mM Phosphate | 0.500 | 0.000 | 0.130 | 0.000 | 4.370 | 5.99 |
| pH 7, 145 mM Sodium, 0 mM Phosphate | 0.500 | 0.000 | 0.130 | 0.000 | 4.370 | 6.97 |
| pH 8, 145 mM Sodium, 0 mM Phosphate | 0.500 | 0.000 | 0.130 | 0.000 | 4.370 | 8.02 |
| pH 9, 145 mM Sodium, 0 mM Phosphate | 0.500 | 0.000 | 0.130 | 0.000 | 4.370 | 9.02 |
| pH 5.5, 145 mM Sodium, 0 mM Phosphate | 0.500 | 0.000 | 0.130 | 0.000 | 4.370 | 5.47 |
| pH 6, 145 mM Sodium, 0 mM Phosphate | 0.500 | 0.000 | 0.130 | 0.000 | 4.370 | 6.30 |
| pH 6.5, 145 mM Sodium, 0 mM Phosphate | 0.500 | 0.000 | 0.130 | 0.000 | 4.370 | 6.65 |
| pH 4, 145 mM Sodium, 100 mM Phosphate | 0.500 | 0.996 | 0.030 | 0.000 | 3.474 | 3.98 |
| pH 5, 145 mM Sodium, 100 mM Phosphate | 0.500 | 1.000 | 0.026 | 0.000 | 3.474 | 4.91 |
| pH 6, 145 mM Sodium, 100 mM Phosphate | 0.500 | 0.999 | 0.003 | 0.000 | 3.498 | 5.98 |
| pH 7, 145 mM Sodium, 100 mM Phosphate | 0.500 | 1.000 | −0.041 | 0.000 | 3.541 | 7.03 |
| pH 8, 145 mM Sodium, 100 mM Phosphate | 0.500 | 1.000 | −0.064 | 0.000 | 3.564 | 8.10 |
| pH 9, 145 mM Sodium, 100 mM Phosphate | 0.500 | 0.999 | −0.069 | 0.000 | 3.569 | 9.03 |
| pH 5.5, 145 mM Sodium, 100 mM Phosphate | 0.500 | 0.999 | 0.026 | 0.000 | 3.474 | 5.58 |
| pH 6, 145 mM Sodium, 100 mM Phosphate | 0.500 | 0.999 | 0.003 | 0.000 | 3.498 | 6.22 |
| pH 6.5, 145 mM Sodium, 100 mM Phosphate | 0.500 | 0.999 | 0.003 | 0.000 | 3.498 | 6.60 |

Once diluted the samples were adjusted to their target pH with 1 M HCl, the volume of which was insignificant and does not alter the final albumin or constituent concentrations. An aliquot (1 mL) of the resulting solution was then placed in a polystyrene cuvette (Sarstedt 10×4×45 mm). The cuvette was then placed into a temperature controlled spectrophotometer that had been pre-equilibrated and controlled at 65° C. The absorbance at 350 nm, referenced against an empty cuvette, was then monitored over a 2 hour period with a reading being taken every 18 seconds. The data were processed by taking the first 7 data points, averaging them (calculating the mean) and then subtracting this from all data points in order to give base absorbance values of around 0. The time taken for this absorbance to then increase by 0.1 AU (Absorbance Units) above this baseline was then recorded for that particular formulation sample. Each formulation sample was performed in duplicate and the time for the absorbance to increase by 0.1 AU for each replicate averaged.

Results:

The processed data with the time for each sample to increase by 0.1 AU, were plotted for time for absorbance increase against pH for each of the formulation constituents tested; n-acetyl-tryptophan, phosphate concentration and sodium concentration. Values above 7200 sec were extrapolated. The data are presented in FIGS. 1 (pH and n-acetyl tryptophan), 2 (pH and phosphate) and 3 (pH and sodium).

Conclusions:

For all the data, except for 50 mM sodium, the optimum pH was between pH 6 and 7. For 50 mM sodium, although insoluble aggregates were not forming, it is possible that high levels of soluble oligomers were being generated and these were not coalescing to form insoluble aggregates. Soluble aggregates can be identified by GP-HPLC.

For the phosphate buffer concentration, there was no significant difference between 50 and 100 mM. However, 0 mM phosphate did appear to be slightly more stable between pH 6 to 8. Although using no phosphate would be best in terms of stability, the use of a buffer aids pH control, for example because it reduces or eliminates the requirement to pH-adjust an albumin prior to formulation.

Increasing sodium levels had a significant effect on stability with a large increase in stability between 145 and 300 mM sodium.

Example 2

Effect of Increasing Sodium Concentration on Albumin Stability

Aim:

Example 1 indicated that increased levels of sodium had a beneficial effect on albumin stability. To investigate this further, increasing concentrations of sodium over a wider range than in Example 1 at the optimum pH range were investigated.

Method:

Albumin at 100 mg/mL in 145 mM NaCl (albumin batch 1401) was diluted to 10 mg/mL according to the Table 6. The buffers used for dilution are shown in Tables 4 and 5.

TABLE 4

| | rHSA Conc (g/L) | Na Molarity (mM) | Tryptophan Molarity (mM) |
|---|---|---|---|
| rHSA solution (1401) | 100 | 154 | — |
| 5M NaCl | — | 5000 | — |
| Tryptophan | — | 501 | 500 |

TABLE 5

| Buffer Stock Solution | Phosphate (mM) | Na (mM) |
|---|---|---|
| 0.5M Phosphate pH 4 | 502 | 500 |
| 0.5M Phosphate pH 5 | 500 | 518 |
| 0.5M Phosphate pH 6 | 500 | 634 |
| 0.5M Phosphate pH 7 | 500 | 851 |
| 0.5M Phosphate pH 8 | 500 | 970 |
| 0.5M Phosphate pH 9 | 500 | 992 |

TABLE 6

| | Stock Volumes to Add (mL) | | | |
|---|---|---|---|---|
| Sample | rHSA | Sodium Phosphate | NaCl | Water |
| pH 6.5, 50 mM Sodium, 25 mM Phosphate | 0.500 | 0.250 | 0.003 | 4.247 |
| pH 6.5, 100 mM Sodium, 25 mM Phosphate | 0.500 | 0.250 | 0.053 | 4.197 |
| pH 6.5, 150 mM Sodium, 25 mM Phosphate | 0.500 | 0.250 | 0.103 | 4.147 |
| pH 6.5, 200 mM Sodium, 25 mM Phosphate | 0.500 | 0.250 | 0.153 | 4.097 |
| pH 6.5, 250 mM Sodium, 25 mM Phosphate | 0.500 | 0.250 | 0.203 | 4.047 |
| pH 6.5, 400 mM Sodium, 25 mM Phosphate | 0.500 | 0.250 | 0.353 | 3.897 |
| pH 6.0, 50 mM Sodium, 25 mM Phosphate | 0.500 | 0.250 | 0.003 | 4.247 |
| pH 6.0, 100 mM Sodium, 25 mM Phosphate | 0.500 | 0.250 | 0.053 | 4.197 |
| pH 6.0, 150 mM Sodium, 25 mM Phosphate | 0.500 | 0.250 | 0.103 | 4.147 |
| pH 6.0, 200 mM Sodium, 25 mM Phosphate | 0.500 | 0.250 | 0.153 | 4.097 |
| pH 6.0, 250 mM Sodium, 25 mM Phosphate | 0.500 | 0.250 | 0.203 | 4.047 |
| pH 6.0, 400 mM Sodium, 25 mM Phosphate | 0.500 | 0.250 | 0.353 | 3.897 |
| pH 7.0, 50 mM Sodium, 25 mM Phosphate | 0.500 | 0.250 | 0.000 | 4.250 |
| pH 7.0, 100 mM Sodium, 25 mM Phosphate | 0.500 | 0.250 | 0.042 | 4.208 |
| pH 7.0, 150 mM Sodium, 25 mM Phosphate | 0.500 | 0.250 | 0.092 | 4.158 |
| pH 7.0, 200 mM Sodium, 25 mM Phosphate | 0.500 | 0.250 | 0.142 | 4.108 |
| pH 7.0, 250 mM Sodium, 25 mM Phosphate | 0.500 | 0.250 | 0.192 | 4.058 |
| pH 7.0, 400 mM Sodium, 25 mM Phosphate | 0.500 | 0.250 | 0.342 | 3.908 |

The dilution was performed by first mixing the albumin and buffer as a bulk and then adjusting it to the correct pH by the addition of 1 M HCl. This was then divided and water and 5 M NaCl added as appropriate. This ensured that all samples were at exactly the same pH. An aliquot (1 mL) of the resulting solution was then placed in a polystyrene cuvette (Sarstedt 10×4×45 mm). The cuvette was then placed into a temperature controlled spectrophotometer that had been pre-equilibrated and controlled at 65° C. The absorbance at 350 nm, referenced against an empty cuvette, was then monitored over a 2 hour period with a reading being taken every 18 seconds. The data were processed by taking the first 7 data points, averaging them (calculating the mean) and then subtracting this from all data points in order to give base absorbance values of around 0. The time taken for this absorbance to then increase by 0.1 AU above this baseline was then recorded for that particular formulation sample. Each formulation sample was performed in duplicate and the time for the absorbance to increase by 0.1 AU for each replicate averaged.

Figure 4:
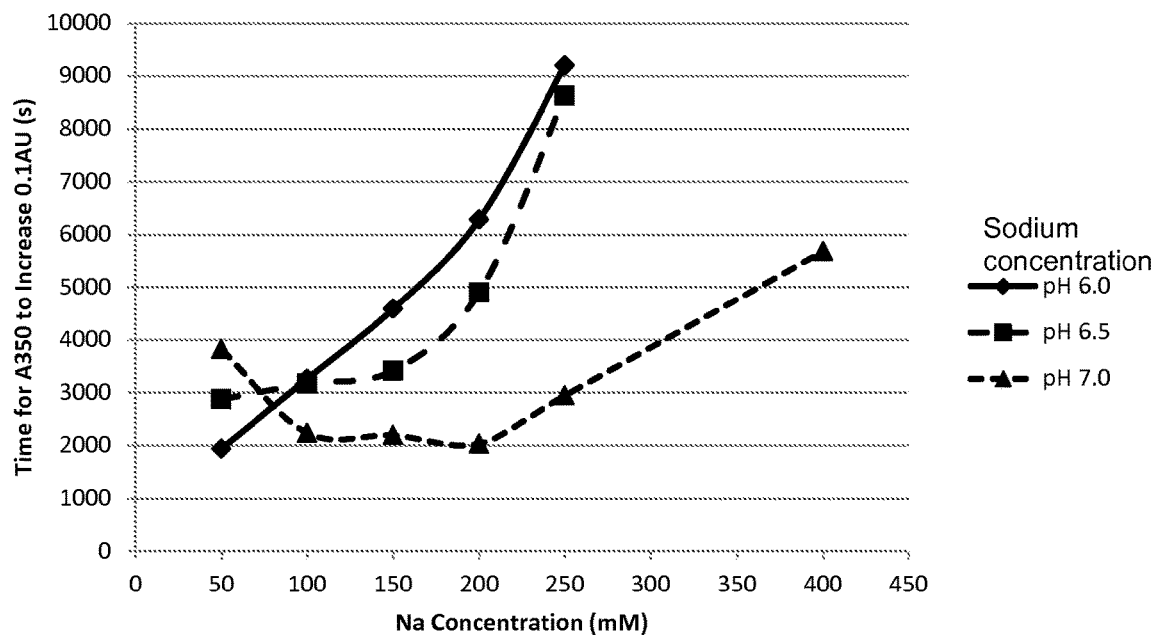
FIG. 4 shows the effect of pH and sodium concentration (for a wide range of sodium concentrations) on the stability of albumin compositions (10 mg/mL), as determined by the time taken (seconds) for the absorbance (A350) to increase by 0.1 AU.

Results:

The processed data with the time for each sample to increase by 0.1 AU, were plotted for time for absorbance increase against Na concentration for each pH. Values above 7200 sec were extrapolated. The data are shown in FIG. 4.

Conclusion:

Consistent with Example 1, increasing levels of sodium increased albumin stability. This was particularly the case around 200 mM where there was a sudden increase in stability. This was the case for all pHs, although it was less obvious at pH 6 since even at <200 mM increasing salt was still having a beneficial effect. The fact that the increase was around 200 mM maybe the reason that it has not been observed previously, since most other albumin formulations are 150 mM or lower in order to keep them approximately physiological. For an albumin used in cell culture media, this should not be an issue as the albumin will be diluted down into the media and the overall salt concentration of the media will be suitable for cell culture.

pH 6 was slightly better than pH 6.5, both being significantly better than pH 7.

Example 3

Effect of Sodium Concentration on the Stability of Different Concentrations of Albumin Aim:

Example 2 shows that sodium concentration is important to stability of albumin. Example 2 was done at an albumin concentration of 10 mg/mL. In order to confirm that this effect is also true at higher concentrations the effect of sodium at higher albumin concentrations was investigated.

Method:

Albumin at 100 mg/mL in 145 mM NaCl (albumin batch 1401) was diluted to 50 or 90 mg/mL according to Table 9. The buffers used for dilution are shown in Tables 7 and 8.

TABLE 7

|  | rHSA Conc (g/L) | Na Molarity (mM) | Tryptophan Molarity (mM) |
|---|---|---|---|
| rHSA solution (1401) | 100 | 154 | — |
| 5M NaCl | — | 5000 | — |
| Tryptophan | — | 501 | 500 |

TABLE 8

| Buffer Stock Solution | Phosphate (mM) | Na (mM) |
|---|---|---|
| 0.5M Phosphate pH 4 | 502 | 500 |
| 0.5M Phosphate pH 5 | 500 | 518 |
| 0.5M Phosphate pH 6 | 500 | 634 |
| 0.5M Phosphate pH 7 | 500 | 851 |
| 0.5M Phosphate pH 8 | 500 | 970 |
| 0.5M Phosphate pH 9 | 500 | 992 |

The dilution was performed by first mixing the albumin and buffer as a bulk and then adjusting it to the correct pH by the addition of 1 M HCl. This was then divided and water and 5 M NaCl added as appropriate. This ensured that all samples were at exactly the same pH.

An aliquot (1 mL) of the resulting solution was then placed in a polystyrene cuvette (Sarstedt 10×4×45 mm). The cuvette was then placed into a temperature controlled spectrophotometer that had been pre-equilibrated and controlled at 65° C. The absorbance at 350 nm, referenced against an empty cuvette, was then monitored over a 2 hour period with a reading being taken every 18 seconds. The data were processed by taking the first 7 data points, averaging them (calculating the mean) and then subtracting this from all data points in order to give base absorbance values of around 0. The time taken for this absorbance to then increase by 0.1 AU above this baseline was then recorded for that particular formulation sample. Each formulation sample was performed in duplicate and the time for the absorbance to increase by 0.1 AU for each replicate averaged.

Figure 5:
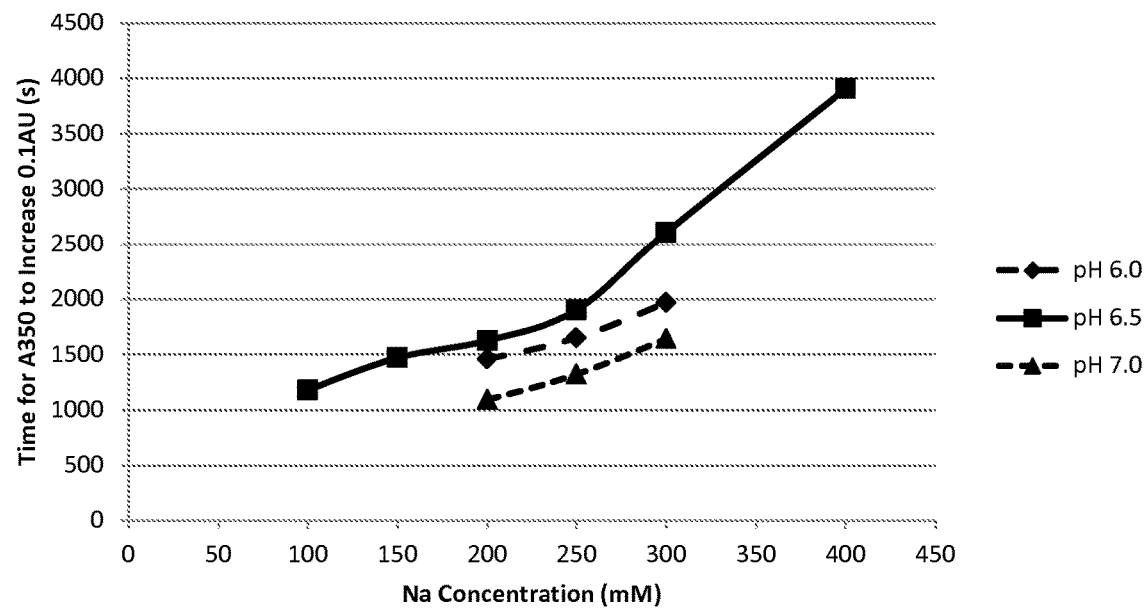
FIG. 5 shows the effect of pH and sodium concentration on the stability of albumin compositions (50 mg/mL), as determined by the time taken (seconds) for the absorbance (A350) to increase by 0.1 AU.
Figure 6:
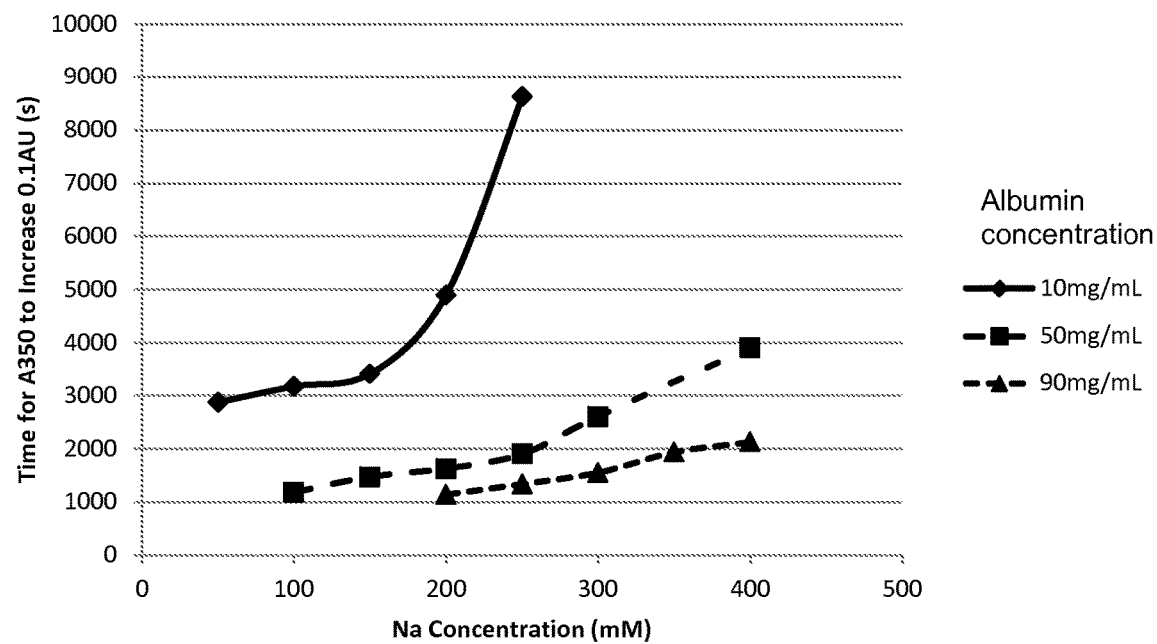
FIG. 6 shows the effect of sodium concentration and albumin concentration on the stability of albumin compositions at pH 6.5, as determined by the time taken (seconds) for the absorbance (A350) to increase by 0.1 AU.

Results:

The processed data with the time for each sample to increase by 0.1 AU were plotted for time for absorbance increase against Na concentration for each pH (6.0, 6.5 and 7.0) at 50 mg/mL albumin and then for 3 different albumin concentrations (10, 50 and 90 mg/mL) at pH 6.5. The data are shown in FIGS. 5 and 6.

Conclusions:

- At 50 mg/mL albumin the trend of increasing sodium concentration improving albumin stability was confirmed at all 3 pHs. In this instance pH 6.5 was the best.
- At pH 6.5, the trend of increased sodium improving stability was again confirmed at all albumin concentrations. The trend was not as pronounced at 90 g/L, but it was still the case that sodium concentrations above 200 mM significantly improved the albumin stability.

TABLE 9

| Sample | rHSA conc (mg/mL) | rHSA | Sodium Phosphate | NaCl | H$_2$O |
|---|---|---|---|---|---|
| pH 6.5, 100 mM Sodium, 25 mM Phosphate | 50 | 1.500 | 0.150 | 0.000 | 1.350 |
| pH 6.5, 150 mM Sodium, 25 mM Phosphate | 50 | 1.500 | 0.150 | 0.025 | 1.325 |
| pH 6.5, 200 mM Sodium, 25 mM Phosphate | 50 | 1.500 | 0.150 | 0.055 | 1.295 |
| pH 6.5, 250 mM Sodium, 25 mM Phosphate | 50 | 1.500 | 0.150 | 0.085 | 1.265 |
| pH 6.5, 300 mM Sodium, 25 mM Phosphate | 50 | 1.500 | 0.150 | 0.115 | 1.235 |
| pH 6.5, 400 mM Sodium, 25 mM Phosphate | 50 | 1.500 | 0.150 | 0.175 | 1.175 |
| pH 6.0, 200 mM Sodium, 25 mM Phosphate | 50 | 1.500 | 0.150 | 0.055 | 1.295 |
| pH 6.0, 250 mM Sodium, 25 mM Phosphate | 50 | 1.500 | 0.150 | 0.085 | 1.265 |
| pH 6.0, 300 mM Sodium, 25 mM Phosphate | 50 | 1.500 | 0.150 | 0.115 | 1.235 |
| pH 7.0, 200 mM Sodium, 25 mM Phosphate | 50 | 1.500 | 0.150 | 0.048 | 1.302 |
| pH 7.0, 250 mM Sodium, 25 mM Phosphate | 50 | 1.500 | 0.150 | 0.078 | 1.272 |
| pH 7.0, 300 mM Sodium, 25 mM Phosphate | 50 | 1.500 | 0.150 | 0.108 | 1.242 |
| pH 6.5, 200 mM Sodium, 25 mM Phosphate | 90 | 2.700 | 0.150 | 0.018 | 0.132 |
| pH 6.5, 250 mM Sodium, 25 mM Phosphate | 90 | 2.700 | 0.150 | 0.048 | 0.102 |
| pH 6.5, 300 mM Sodium, 25 mM Phosphate | 90 | 2.700 | 0.150 | 0.078 | 0.072 |
| pH 6.5, 300 mM Sodium, 25 mM Phosphate | 90 | 2.700 | 0.150 | 0.078 | 0.072 |
| pH 6.5, 350 mM Sodium, 25 mM Phosphate | 90 | 2.700 | 0.150 | 0.108 | 0.042 |
| pH 6.5, 400 mM Sodium, 25 mM Phosphate | 90 | 2.700 | 0.150 | 0.138 | 0.012 |

Example 4

Effect of Sodium Concentration on the Production of Soluble Aggregates in Albumin Aim:
Examples 1 to 3 show, using the formulation screening assay that measures insoluble aggregates, that increasing sodium concentrations improved albumin stability. In order to look at soluble aggregates (albumin polymer) GP-HPLC needs to be used as the measurement tool with polymer formation monitored in an accelerated stability trial at 40° C. over a 2 week period. The tests were carried out at pH 6.5 because this was shown, by Examples 1 to 3, to be a preferred pH. A control of albumin in previous formulation conditions (pH 8.6, 150 mM Na) was also used to confirm that a new formulation would be significantly beneficial. The actual albumin concentration was 90 mg/mL instead of the anticipated 100 mg/mL as this was the highest that could be used allowing for dilution into the various formulations. However, it is thought that observed trends at this slightly lower concentration will be the same at higher albumin concentrations.

Method:
Albumin at 100 mg/mL in 145 mM NaCl (albumin batch 1401) was diluted to 90 mg/mL according to Table 12. The buffers used for dilution are shown in Tables 10 and 11.

TABLE 10

|  | rHSA Conc (g/L) | Na Molarity (mM) |
|---|---|---|
| rHSA solution (1401) | 100 | 154 |
| 5M NaCl | — | 5000 |

TABLE 11

| Buffer Stock Solution | Make up Vol (mL) | $NaH_2PO_4 \cdot 2H_2O$ (g) | 27% NaOH (mL)* | Phosphate (mM) | Na (mM) |
|---|---|---|---|---|---|
| 0.5M Phosphate pH 6 | 250 | 19.51 | 3.8 | 500 | 634 |

*27% w/w NaOH density = 1.3

TABLE 12

| | | Stock Volumes to Add (mL) | | |
|---|---|---|---|---|
| Sample | rHSA | Sodium Phosphate | NaCl | $H_2O$ |
| pH 8.6, 150 mM Sodium | 9.0 | 0.000 | 0.023 | 0.977 |
| pH 6.5, 150 mM Sodium, 25 mM Phosphate | 9.0 | 0.500 | 0.000 | 0.500 |
| pH 6.5, 200 mM Sodium, 25 mM Phosphate | 9.0 | 0.500 | 0.059 | 0.441 |
| pH 6.5, 250 mM Sodium, 25 mM Phosphate | 9.0 | 0.500 | 0.159 | 0.341 |
| pH 6.5, 300 mM Sodium, 25 mM Phosphate | 9.0 | 0.500 | 0.259 | 0.241 |
| pH 6.5, 350 mM Sodium, 25 mM Phosphate | 9.0 | 0.500 | 0.359 | 0.141 |

The dilution was performed by first mixing the albumin and buffer as a bulk and then adjusting it to the correct pH by the addition of 1 M HCl. This was then divided into appropriate sized aliquots and water and 5 M NaCl added as required. This ensured that all samples were at exactly the same pH.

10 mL of each sample was then sterile filtered into a baked 10 mL glass vial stopped with a sterile butyl rubber seal and then over-sealed. A T0 sample of ~200 μL was then taken and the vial placed in a water bath that was set at 40° C. Samples (~200 μL) were then taken from each of the vials after 14 days, diluted 2 fold and injected in triplicate on the GP-HPLC system.

The GP-HPLC system was run, by injecting (25 μL) onto a 7.8 mm id×300 mm length TSK $G3000SW_{XL}$ column (Tosoh Bioscience), with a 6.0 mm id×40 mm length TSK SW guard column (Tosoh Bioscience). Samples were chromatographed in 25 mM sodium phosphate, 100 mM sodium sulphate, 0.05% (w/v) sodium azide, pH 7.0 at 1 mL/min and monitored by UV detection at 280 nm. Monomer, dimer, trimer and polymer content were quantified as % w/w by their respective peak area relative to the total peak area. Results from the triplicate injections were averaged to get a mean result for each sample.

Figure 7:
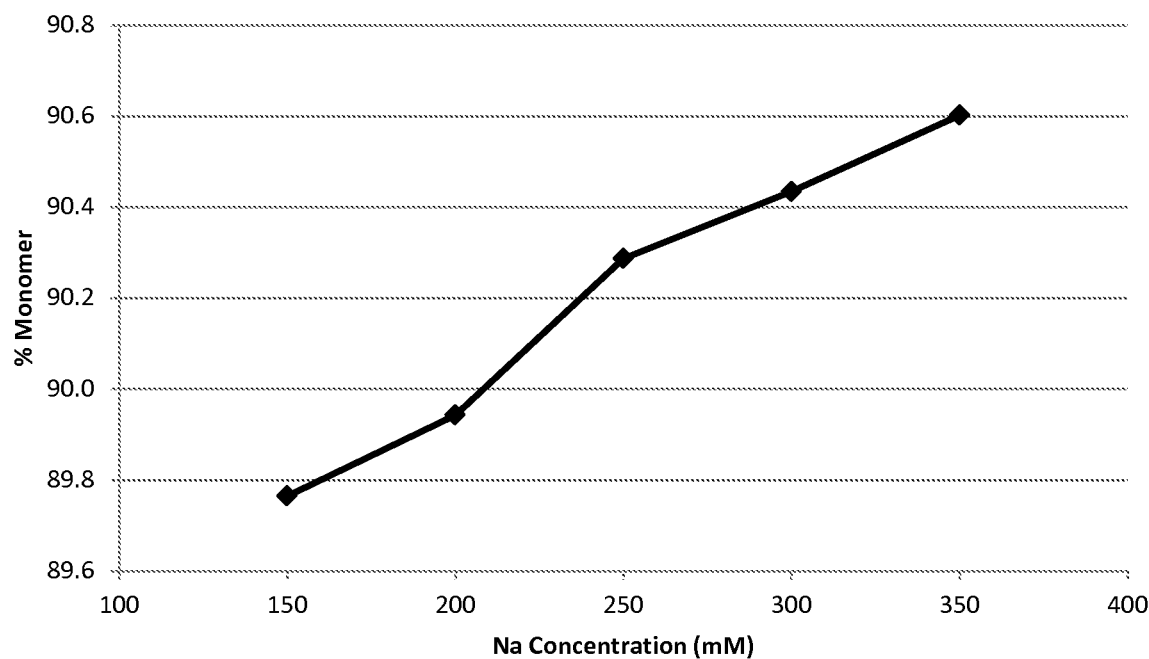
FIG. 7 shows the relationship between sodium concentration and relative monomer content (%) for albumin compositions incubated at 40° C. for 14 days.
Figure 8:
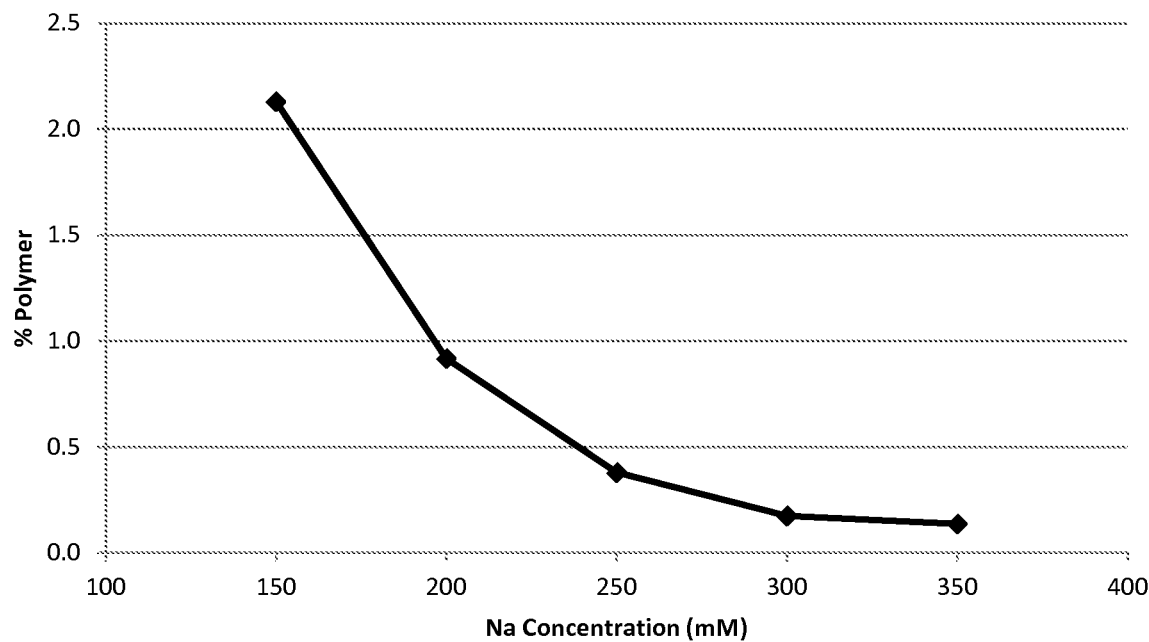
FIG. 8 shows the relationship between sodium concentration and relative polymer content (%) for albumin compositions incubated at 40° C. for 14 days.

Results:
The data for the 14 day time point for monomer (FIG. 7) and polymer (FIG. 8) were plotted against sodium concentration.

Conclusions:
The formulation at pH 6.5 was significantly better than that at pH 8.6 used for albumin batch 1401. The level of polymer significantly increased at pH 8.6, rising to approximately 20% after 2 weeks at 40° C. compared to ~2% for the same sodium concentration at pH 6.5.
The proposed trend of increasing sodium increasing albumin stability observed with the screening assay is confirmed here for soluble aggregates with a significant trend of reduced polymer formation with increasing sodium concentration. Going from 150 mM, a standard albumin concentration due to it being close to physiological conditions, to 200 mM sodium the level of polymer decreases by >2 fold with then a further decrease of ~2 fold going from 200 to 250 mM. Although the polymer decreases even further with higher salt concentrations up to 350 mM (and potentially beyond) the rate of decrease is slower. These results are matched in an increase in monomer remaining with increased sodium. Overall there is a >4 fold decrease in polymer formation going from 150 to 250 mM sodium. Consequently, a preferred albumin formulation is 25 mM phosphate buffer pH 6.5, 250 mM sodium. The phosphate is present to aid pH control.

Notably, sodium will come from both sodium chloride and sodium phosphate (including any NaOH used to ensure the pH of the phosphate is correct) and therefore the buffer is not 250 mM NaCl.

Although this work has all been performed with sodium, similar monovalent or bivalent metal ions are expected to have a similar effect. However, sodium is a preferred metal ion because it is known to be compatible with stem cell culture.

Example 5

Effect of Albumin Concentration and Sodium Ion Concentration on Stability of Albumin Method:

A sample of purified albumin containing low octanoate (~0.2 mM octanotae, 100 g/L albumin) was diafiltered against a minimum of 10 continuous volumes of 25 mM phosphate, 50 mM sodium pH 6.5 and then concentrated to 338 g/L using a 10 KDa Pall Omega crossflow UF to generate a 50 mM sodium starting material. The sample was then diluted with water, 5 M NaCl and 0.5 M sodium phosphate pH 6.5 as shown in Table 13:

TABLE 13

| | | | | | |
|---|---|---|---|---|---|
| | Sample details | | Volume of stock required (mL) | | |
| Sample | rHSA (mg/mL) | Na+ (mM) | rHSA (338 g/L) | Sodium Phosphate (0.5M, pH 6.5) | NaCl (5M) | Water |
| 1 | 100 | 50 | 1.78 | 0.21 | 0.01 | 4.00 |
| 2 | 100 | 100 | 1.78 | 0.21 | 0.07 | 3.94 |
| 3 | 100 | 150 | 1.78 | 0.21 | 0.13 | 3.88 |
| 4 | 100 | 200 | 1.78 | 0.21 | 0.19 | 3.82 |
| 5 | 100 | 250 | 1.78 | 0.21 | 0.25 | 3.76 |
| 6 | 100 | 300 | 1.78 | 0.21 | 0.31 | 3.70 |
| 7 | 100 | 400 | 1.78 | 0.21 | 0.43 | 3.58 |
| 8 | 100 | 500 | 1.78 | 0.21 | 0.55 | 3.46 |
| 9 | 150 | 50 | 2.67 | 0.17 | 0.01 | 3.16 |
| 10 | 150 | 100 | 2.67 | 0.17 | 0.07 | 3.10 |
| 11 | 150 | 150 | 2.67 | 0.17 | 0.13 | 3.04 |
| 12 | 150 | 200 | 2.67 | 0.17 | 0.19 | 2.98 |
| 13 | 150 | 250 | 2.67 | 0.17 | 0.25 | 2.92 |
| 14 | 150 | 300 | 2.67 | 0.17 | 0.31 | 2.86 |
| 15 | 150 | 400 | 2.67 | 0.17 | 0.43 | 2.74 |
| 16 | 150 | 500 | 2.67 | 0.17 | 0.55 | 2.62 |
| 17 | 200 | 50 | 3.56 | 0.12 | 0.01 | 2.32 |
| 18 | 200 | 100 | 3.56 | 0.12 | 0.07 | 2.26 |
| 19 | 200 | 150 | 3.56 | 0.12 | 0.13 | 2.20 |
| 20 | 200 | 200 | 3.56 | 0.12 | 0.19 | 2.14 |
| 21 | 200 | 250 | 3.56 | 0.12 | 0.25 | 2.08 |
| 22 | 200 | 300 | 3.56 | 0.12 | 0.31 | 2.02 |
| 23 | 200 | 400 | 3.56 | 0.12 | 0.43 | 1.90 |
| 24 | 200 | 500 | 3.56 | 0.12 | 0.55 | 1.78 |
| 25 | 250 | 50 | 4.44 | 0.08 | 0.00 | 1.47 |
| 26 | 250 | 100 | 4.44 | 0.08 | 0.06 | 1.41 |
| 27 | 250 | 150 | 4.44 | 0.08 | 0.12 | 1.35 |
| 28 | 250 | 200 | 4.44 | 0.08 | 0.18 | 1.29 |
| 29 | 250 | 250 | 4.44 | 0.08 | 0.24 | 1.23 |
| 30 | 250 | 300 | 4.44 | 0.08 | 0.30 | 1.17 |
| 31 | 250 | 400 | 4.44 | 0.08 | 0.42 | 1.05 |
| 32 | 250 | 500 | 4.44 | 0.08 | 0.54 | 0.93 |

The samples were then aseptically filtered (0.22 μm filter) into sterile 5 mL glass vials and the vials placed in a 40° C. incubator for 4 weeks. An aliquot from each sample was taken out at intervals, diluted to 40 g/L with water and assayed for soluble aggregates by GP-HPLC as per Example 4.

Figure 11:
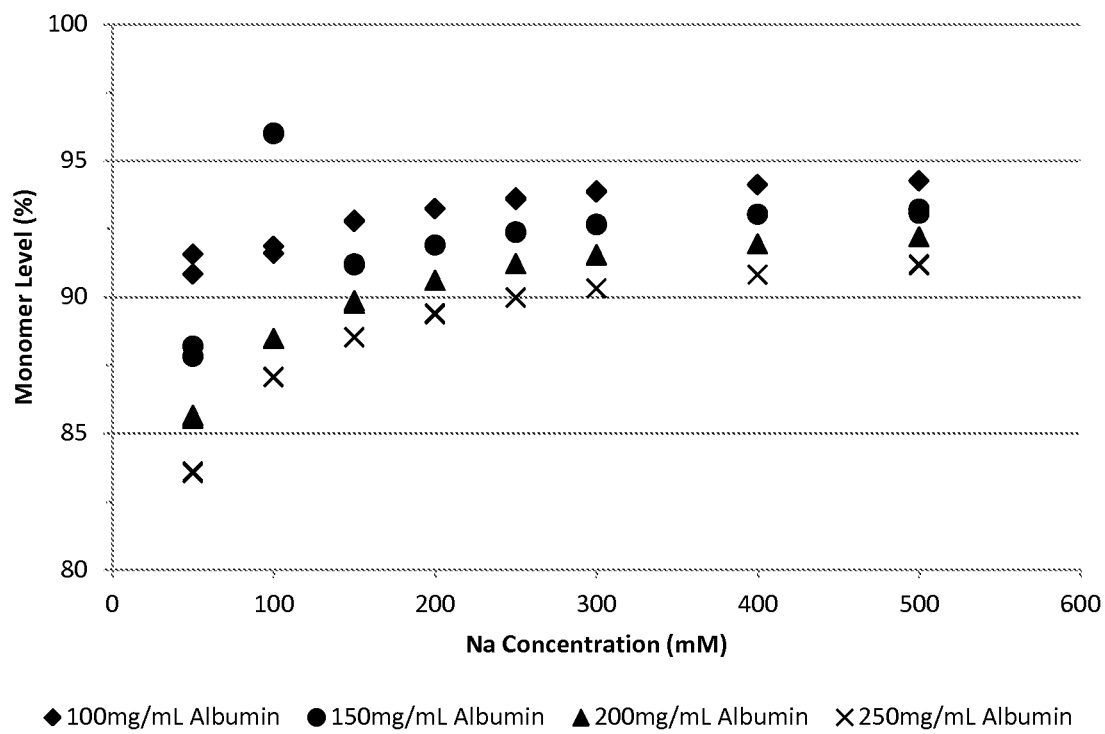
FIG. 11 shows the effect of sodium concentration and albumin concentration on albumin stability as determined by the remaining monomer content following incubation at 40° C. for 4 weeks.

Results:

FIG. 11 shows monomer levels after a 4 week incubation. A higher monomer content shows better stability.

Conclusions:

All points follow a trend apart from the 150 g/L albumin, 100 mM sodium sample. It is unclear why this sample is out of trend but is likely to be an outlier and does not detract from the overall conclusions of the experiment.

For all albumin concentrations tested, there is a clear correlation of increasing monomer content i.e. increasing stability with increasing sodium content.

The majority of the improved stability comes with increasing the sodium ion concentration up to ~200 mM. Above this concentration, although there is some further increase in stability it has mostly levelled off. Consequently the optimum sodium ion concentration is 200 mM or higher.

Example 6

Effect of Different Cations on Stability of Albumin

Method:

A sample of purified albumin containing low octanoate (~0.2 mM @ 100 g/L albumin) was diluted initially to 50 mg/mL with water such that it contained 50 mg/mL albumin, 75 mM NaCl and no pH buffer constituent. The pH was adjusted with 0.5 M HCl to pH 6.43, the amount of HCl added was insignificant and would not have altered the albumin or other constituent concentrations. The samples were then diluted further to 10 mg/mL in UV transparent microtitre plate wells using 1 M cation stocks (KCl, NH$_4$Cl, CaCl$_2$, MgCl$_2$, NaCl) as shown in Table 14.

TABLE 14

| | Sample parameters | | | | Stock Volumes to Add (μL) | | |
|---|---|---|---|---|---|---|---|
| | Cation (mM) | Final Vol (ML) | rHSA (mg/mL) | Na+ (mM) | rHSA (50 g/L) | Cation (1M) | Water |
| A | 50 mM | 250 | 10 | 50 | 50.0 | 8.75 | 191.3 |
| B | 100 mM | 250 | 10 | 100 | 50.0 | 21.25 | 178.8 |
| C | 150 mM | 250 | 10 | 150 | 50.0 | 33.75 | 166.3 |
| D | 200 mM | 250 | 10 | 200 | 50.0 | 46.25 | 153.8 |
| E | 250 mM | 250 | 10 | 250 | 50.0 | 58.75 | 141.3 |
| F | 300 mM | 250 | 10 | 300 | 50.0 | 71.25 | 128.8 |
| G | 400 mM | 250 | 10 | 400 | 50.0 | 96.25 | 103.8 |
| H | 500 mM | 250 | 10 | 500 | 50.0 | 121.25 | 78.8 |

Samples for each of KCl, NH$_4$Cl, CaCl$_2$, MgCl$_2$, NaCl were prepared according to Table 14. Therefore, in total, 40 different samples were prepared. Each sample was tested in duplicate on a microtitre plate.

The microtitre plate was gently rocked to mix the contents of each well, centrifuged to remove any air bubbles and placed in a Biotek Synergy Mx (Potton, UK) plate reader that had been pre-equilibrated and controlled at 65° C. The plate was then read at 350 nm every minute over a total incubation time of 8 hours. Gen5 software (Biotek software for the plate reader version 2.00.18) was used to calculate the time taken for the A350 nm absorbance to increase by 0.2 adsorption units above a base line. The base line was calculated from the mean of the first 5 data points.

Figure 12:
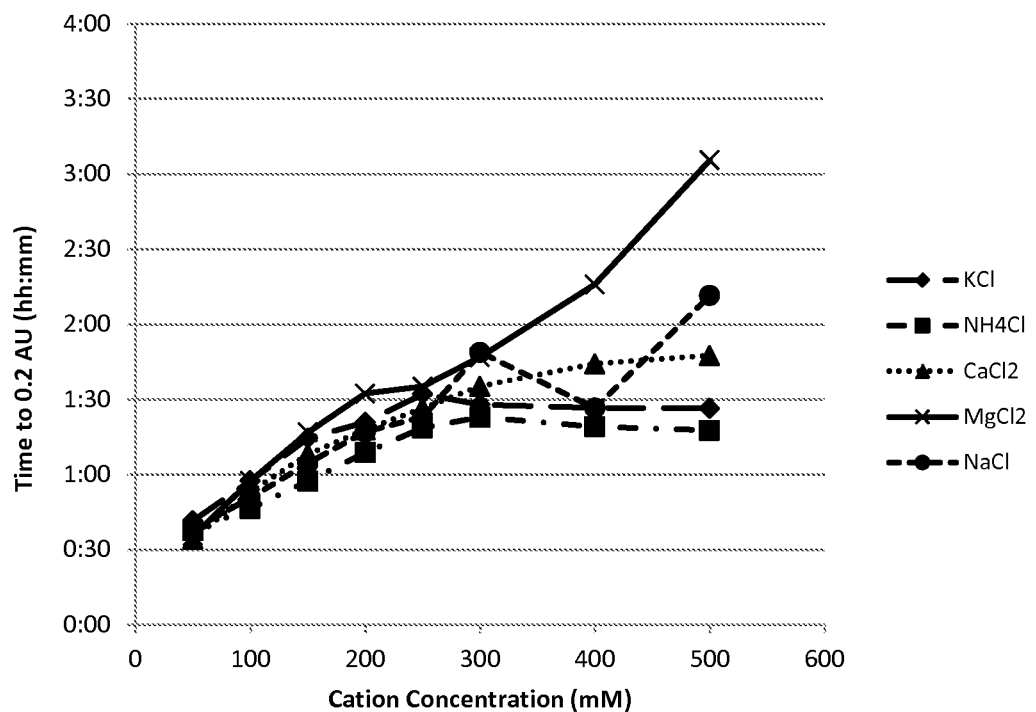
FIG. 12 shows the effect of cation species and cation concentration on albumin stability as determined by the time taken (seconds) for the absorbance (A350) to increase by 0.2 AU.

Results:

FIG. 12 shows the time taken for the absorbance of samples to increase to 0.2 units above the baseline. A longer time shows better stability.

Conclusions:

The control using NaCl shows the same trend as per the other examples i.e. increasing sodium levels improves the stability. This confirms that this microtitre plate method is suitable for testing stability effects.

For all the different cations, both single and dual valency (group 1 metals and group 2 metals, respectively) there was a clear increase in albumin stability with increasing cation concentration up to 500 mM and probably beyond.

These data indicate that while all cations improve stability albumin, $MgCl_2$ is very good.

Example 7

Effect of Different Anions on the Stability of Albumin

Method:

A sample of purified albumin containing a low concentration of octanoate (~0.2 mM, 100 g/L albumin) was diluted initially to 50 mg/mL with water such that it contained 50 mg/mL albumin, 75 mM NaCl and no pH buffer constituent. The sample was pH adjusted with 0.5 M HCl to 6.43, the amount of HCl added was insignificant and would not have altered the albumin or constituent concentrations. 1 M sodium anion stock solutions were prepared according to Table 15.

TABLE 15

Anion stocks

| Anion Stock Solution | MW* of chemical | Number of Na atoms in chemical | Mass Chemical (g) | 27% NaOH (mL) | Sodium ion (mM) |
|---|---|---|---|---|---|
| NaCl | 58.44 | 1 | 5.84 | 0.0 | 1000 |
| $Na_2SO_4$ | 142.04 | 2 | 7.12 | 0.0 | 1003 |
| $NaH_2PO_4 \cdot 2H_2O$ | 156.02 | 1 | 15.61 | 6.2 | 1545 |
| Trisodium citrate | 294.1 | 3 | 9.80 | 0.0 | 1000 |
| Na Acetate | 136.08 | 1 | 13.61 | 0.0 | 1000 |

*MW: molecular weight

The albumin and anion stocks were used as detailed below, being made to a final volume of 1 mL in a polystyrene cuvette (Sarstedt 10×4×45 mm). The samples were gently mixed prior to the cuvettes being placed into a temperature controlled spectrophotometer that had been pre-equilibrated and controlled at 65° C. The absorbance at 350 nm, referenced against an empty cuvette, was then monitored over a 2 hour period with a reading taken every 30 seconds. The data was processed by taking the first 9 data points (~the first 4 minutes), calculating the mean (average) and then subtracting this from all data points in order to give a baseline absorbance. The time taken for the absorbance to increase by 0.1 AU above this baseline was recorded for that particular sample. If the absorbance did not go above 0.1 AU in 2 hours (7200 seconds), then the data was extrapolated in order to get an approximate time. Samples for which the absorbance does not go above 0.1 AU in 2 hours are significantly improved in stability compared to samples having lower cation concentrations.

A six cuvette holder in the spectrophotometer was used with the first sample always being a control and the other five samples using an increasing excipient (i.e. test material such as NaCl, $Na_2SO_4$) concentration. The control was always a pH 6.5 sample containing 250 mM NaCl, this needed to remain in solution with no insoluble aggregates over the full 2 hour 65° C. incubation for the test to be considered to be valid.

TABLE 16

| Sample | Anion concentration and source | Sample parameters (final volume = 1000 µL) rHSA (mg/mL) | $Na^+$ (mM) | Stock Volumes to Add (µL) rHSA (50 mg/mL) | Anion * (1M) | Water |
|---|---|---|---|---|---|---|
| 1 | 50 mM NaCl | 10 | 50 | 200 | 35.0 | 765.0 |
| 2 | 150 mM NaCl | 10 | 150 | 200 | 135.0 | 665.0 |
| 3 | 200 mM NaCl | 10 | 200 | 200 | 185.0 | 615.0 |
| 4 | 250 mM NaCl | 10 | 250 | 200 | 235.0 | 565.0 |
| 5 | 300 mM NaCl | 10 | 300 | 200 | 285.0 | 515.0 |
| 6 | 400 mM NaCl | 10 | 400 | 200 | 385.0 | 415.0 |
| 7 | 50 mM $Na_2SO_4$ | 10 | 50 | 200 | 34.9 | 765.1 |
| 8 | 150 mM $Na_2SO_4$ | 10 | 150 | 200 | 134.7 | 665.3 |
| 9 | 200 mM $Na_2SO_4$ | 10 | 200 | 200 | 184.5 | 615.5 |
| 10 | 250 mM $Na_2SO_4$ | 10 | 250 | 200 | 234.4 | 565.6 |
| 11 | 400 mM $Na_2SO4$ | 10 | 400 | 200 | 384.0 | 416.0 |
| 12 | 70 mM $NaH_2PO_4$ | 10 | 69 | 200 | 35.0 | 765.0 |
| 13 | 220 mM $NaH_2PO_4$ | 10 | 223 | 200 | 134.7 | 665.3 |
| 14 | 300 mM $NaH_2PO_4$ | 10 | 300 | 200 | 184.5 | 615.5 |
| 15 | 380 mM $NaH_2PO_4$ | 10 | 377 | 200 | 234.4 | 565.6 |
| 16 | 600 mM $NaH_2PO_4$ | 10 | 608 | 200 | 384.0 | 416.0 |
| 17 | 50 mM Na Citrate | 10 | 50 | 200 | 35.0 | 765.0 |
| 18 | 150 mM Na Citrate | 10 | 150 | 200 | 135.0 | 665.0 |
| 19 | 200 mM Na Citrate | 10 | 200 | 200 | 185.1 | 614.9 |
| 20 | 250 mM Na Citrate | 10 | 250 | 200 | 235.1 | 564.9 |

TABLE 16-continued

| Sample | Anion concentration and source | Sample parameters (final volume = 1000 μL) rHSA (mg/mL) | Na+ (mM) | rHSA (50 mg/mL) | Stock Volumes to Add (μL) Anion * (1M) | Water |
|---|---|---|---|---|---|---|
| 21 | 400 mM Na Citrate | 10 | 400 | 200 | 385.1 | 414.9 |
| 22 | 50 mM Na Acetate | 10 | 50 | 200 | 35.0 | 765.0 |
| 23 | 150 mM Na Acetate | 10 | 150 | 200 | 135.0 | 665.0 |
| 24 | 200 mM Na Acetate | 10 | 200 | 200 | 185.0 | 615.0 |
| 25 | 250 mM Na Acetate | 10 | 250 | 200 | 235.0 | 565.0 |
| 26 | 400 mM Na Acetate | 10 | 400 | 200 | 384.9 | 415.1 |

* Anion stock solutions are described in Table 15

For the citrate samples, the stabilizing effect of the sodium was inconclusive when measuring the insoluble aggregates as detected by the A350 nm absorbance increase. Therefore after the 2 hour, 65° C. incubation in the spectrophotometer, the samples were removed, centrifuged to remove any large particles and the samples were analyzed for soluble aggregates by GP-HPLC (as per Example 4). The data was expressed as % monomeric albumin remaining (the higher the value the more stable the formulation). This was also done for the phosphate samples.

Figure 13:
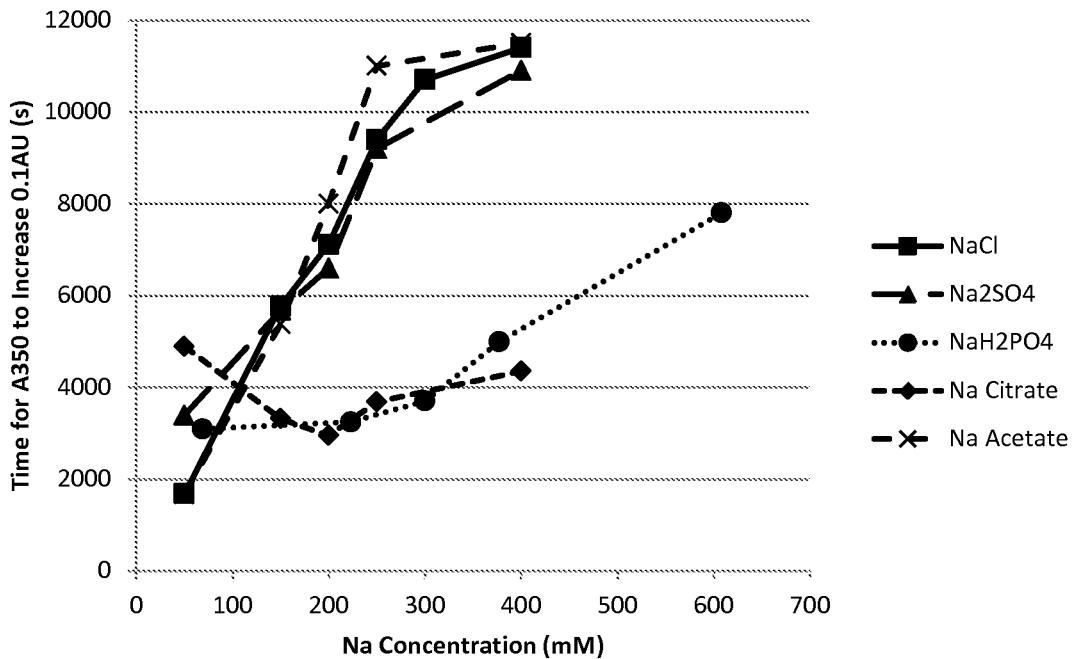
FIG. 13 shows the effect of sodium ion concentration and anion species on albumin stability as determined by the time taken (seconds) for the absorbance (A350) to increase by 0.1 AU.
Figure 14:
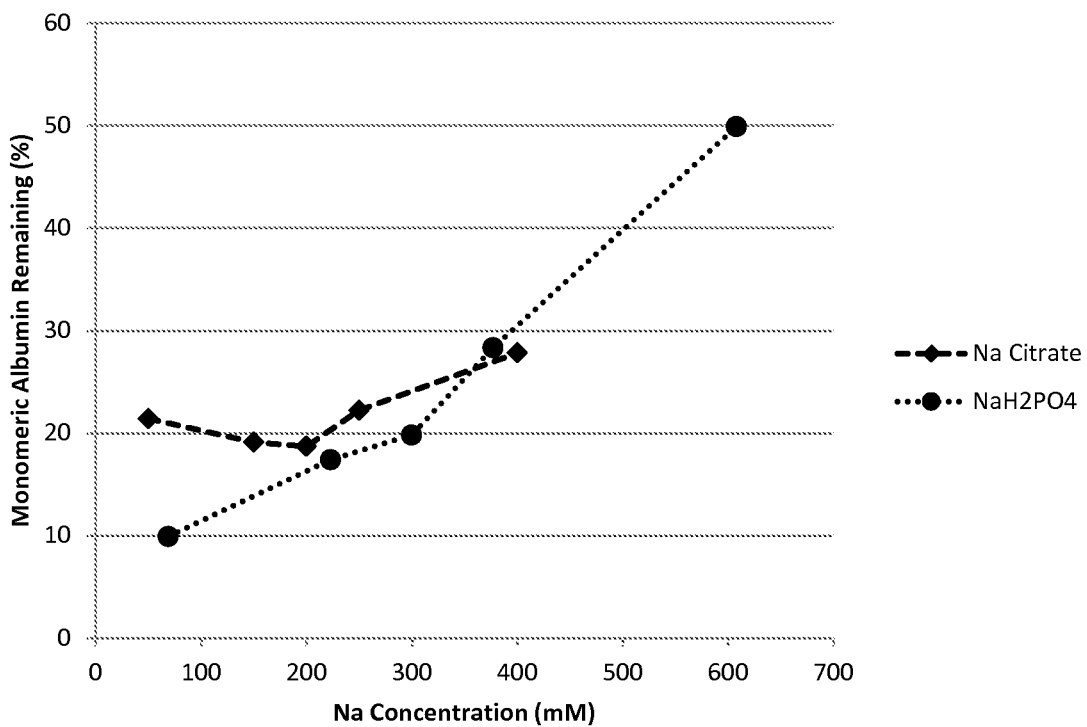
FIG. 14 shows the effect of sodium ion concentration and anion species on albumin stability as determined by the remaining monomer content following incubation at 65° C. for 2 hours.

Results:

All controls were valid. FIG. 13 shows the effect of sodium ion concentration and anion species on the time taken for the A350 absorbance to increase to 0.1 AU above the base line. FIG. 14 shows, the effect of citrate, phosphate and sodium on the stability of albumin following a 65° C., 2 hour incubation. A higher monomer level shows a higher stability. The results for the pH 6.5 controls (250 mM sodium) run at the same time gave a mean result of 81% monomer content.

Conclusions:

Sodium chloride (sodium salt of an inorganic acid), sodium sulphate (sodium salt of a divalent acid) and sodium acetate (sodium salt of an organic acid) all gave a strong increase in albumin stability with increasing sodium concentration.

For sodium dihydrogen phosphate the trend was not as strong as sodium chloride, sodium sulphate and sodium acetate. However, at 150 mM and above there is an increasing trend of stability with increasing sodium content. This trend was confirmed when the soluble aggregates were measured as shown by the strong trend of increasing monomer remaining with increasing sodium concentration.

The trend of increasing stability with increasing sodium concentration for the sodium phosphate samples continued through to 600 mM sodium and would probably continue to higher sodium concentrations.

For sodium citrate there was no obvious trend in albumin stability with sodium concentration as measured by the A350 nm absorbance for the presence of insoluble aggregates. However, when the samples (after incubation at 65° C. for 2 hours) were assessed for soluble aggregates through the measurement of % monomer content remaining by GP-HPLC then there was a trend. At 200 mM sodium and below, the monomer content was fairly flat but as the sodium content increased above 200 mM there was a definite trend of increasing monomer content and therefore albumin stability. Citrate is a chelating agent and therefore the sodium present is chelated to the citrate and is unlikely to be as available to stabilize the albumin as the sodium provided, for example, by NaCl.

Consequently, the inventors believe that any sodium salt (or any other mono or divalent anion based on the previous example) will impart stability on albumin, with a trend of increasing stability with increasing anion concentration.

Example 8

Effect of Different Buffers on Albumin Stability

Method:

A sample of purified albumin containing a low concentration of octanoate (~0.2 mM, 100 g/L albumin) was diluted initially to 50 mg/mL with water such that it contained 50 mg/mL albumin, 75 mM NaCl and no buffer constituent. The sample was pH adjusted with 0.5 M HCl to pH 6.43, the amount of HCl added was insignificant and would not have altered the albumin or constituent concentrations.

An unbuffered stock of 1 M NaCl together with the following buffers (Table 17) pH adjusted to pH 6.43 as per the albumin stock (so that when added to the albumin the pH would not change) was prepared. For phosphate the pH was adjusted with 27% NaOH, for citrate it was adjusted with citric acid (citric acid powder) and for acetate it was adjusted with acetic acid (glacial acetic acid):

TABLE 17

| Anion Stock Solution | Final Vol (mL) | MW of chemical | Number of Na atoms in chemical | Mass Chemical (g) | 27% NaOH (mL) | Na (mM) | Buffer Molarity (mM) |
|---|---|---|---|---|---|---|---|
| NaCl | 100 | 58.44 | 1 | 5.84 | 0.0 | 1000 | N/A |
| NaH$_2$PO$_4$•2H$_2$O | 100 | 156.02 | 1 | 15.61 | 6.2 | 1545 | 1001 |
| Na Citrate | 100 | 294.1 | 3 | 9.80 | 0.0 | 1000 | 333 |
| Na Acetate | 100 | 136.08 | 1 | 13.61 | 0.0 | 1000 | 1000 |

The amount of acid added was insignificant and would not have altered the albumin or constituent concentrations.

The albumin and buffer stocks were used as detailed below, being made to a final volume of 1 mL in a polystyrene cuvette (Sarstedt 10×4×45 mm). The samples were gently mixed prior to the cuvettes being placed into a temperature controlled spectrophotometer that had been pre-equilibrated and controlled at 65° C. The absorbance at 350 nm, referenced against an empty cuvette, was then monitored over a 2 hour period with a reading taken every 30 seconds. The data was processed by taking the first 9 data points (~the first 4 minutes), calculating the mean and then subtracting this from all data points in order to give a baseline absorbance. The time taken for the absorbance to increase by 0.1 AU above this baseline was recorded for that particular formulation sample. If the absorbance did not go above 0.1 AU in 2 hours (7200 seconds) then the data was extrapolated in order to get and approximate time.

A six cuvette holder in the spectrophotometer was used with the first sample always being a control and the other five samples using an increasing excipient concentration. The control was always a pH 6.5 sample containing 250 mM NaCl, this needed to remain in solution with no insoluble aggregates over the full 2 hour 65° C. incubation for the test to be considered to be valid.

Figure 15:
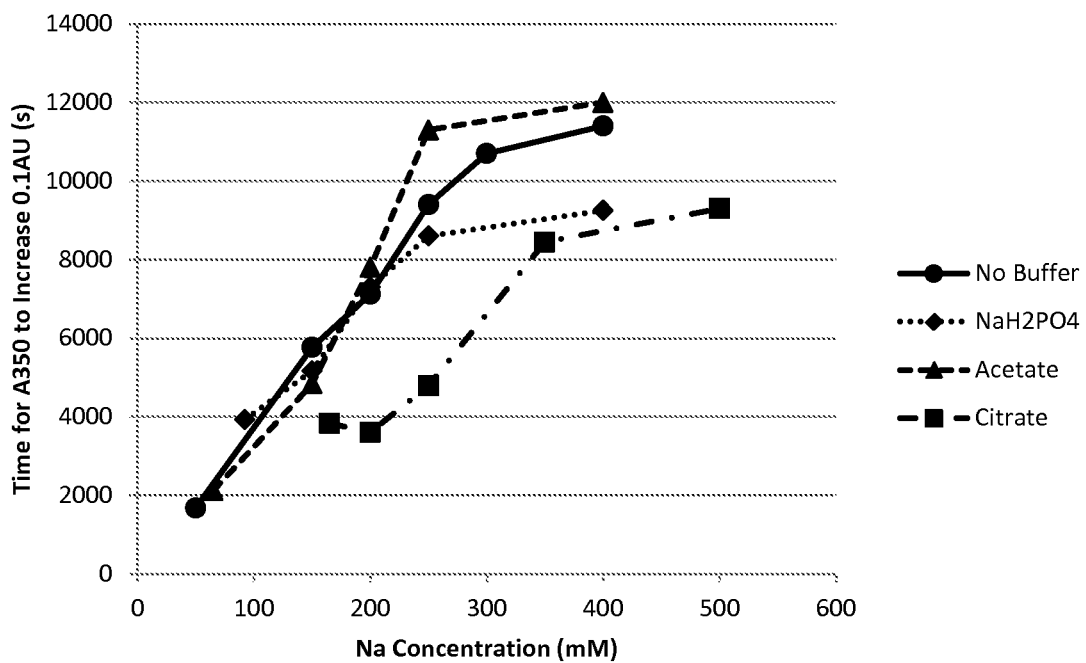
FIG. 15 shows the effect of sodium ion concentration in the presence of different buffer anions on albumin stability wherein the contribution of sodium from both NaCl and the buffer is included, as determined by the time taken (seconds) for the absorbance (A350) to increase by 0.1 AU.

Results:

All controls were valid. For the samples, the time taken for the A350 absorbance to increase to 0.1 AU above the base line was plotted against the sodium concentration. FIG. 15 shows that for all buffers, albumin stability increases as sodium ion concentration increases.

Figure 16:
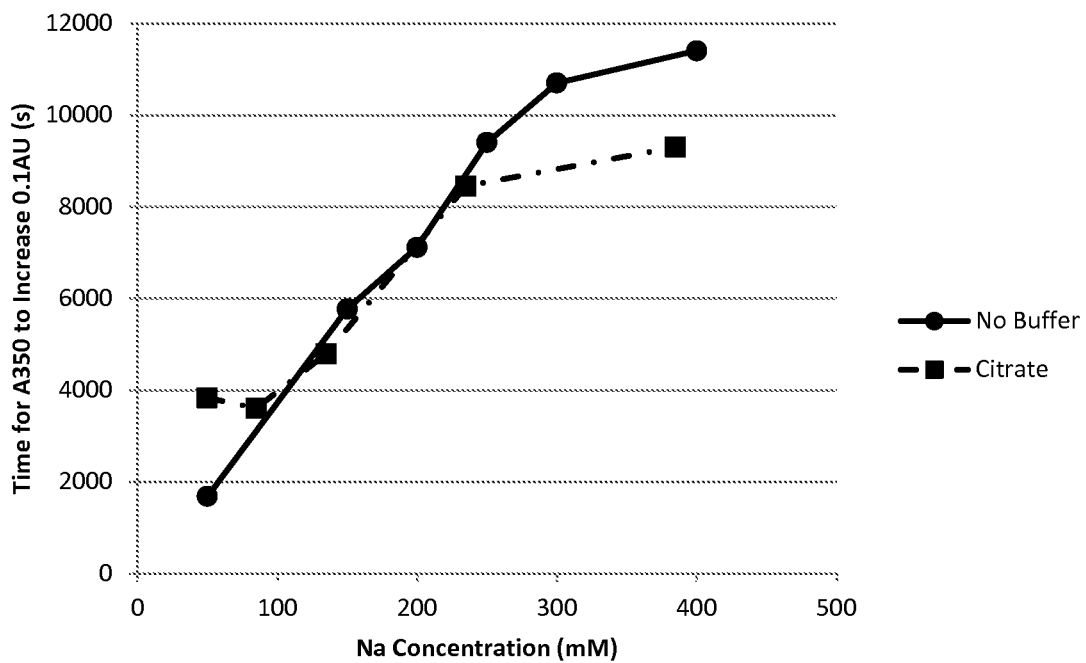
FIG. 16 shows the effect of sodium ion concentration in the presence of no buffering ion or 50 mM citrate as a buffering ion on albumin stability where the contribution of sodium ion from the sodium citrate buffer is ignored, as determined by the time taken (seconds) for the absorbance (A350) to increase by 0.1 AU.

For the citrate samples the trend appears offset relative to the other samples. Consequently, the data for no buffer (sodium provided only by NaCl) was plotted together with the samples buffered with sodium citrate, but with the sodium concentration coming from the sodium citrate ignored (FIG. 16).

Conclusions:

For all buffers, and also with no buffer, there is a clear trend of increasing albumin stability with increasing sodium concentration.

Even with citrate, which did not appear to be as good a sodium donator for albumin stability as NaCl, there was a trend of increasing stability within increasing sodium concentration but it was offset slightly. The reason for this offset is that, like for all the buffers, the sodium from the buffer was used in the calculation of the total sodium content. Consequently, if this sodium is not as effective (e.g. available) as sodium from sodium chloride (as shown in the previous examples) then there will be an offset. This was confirmed by FIG. 16.

TABLE 18

| Sample (final volume = 1000 µL) | Sample parameters | | | Stock Volumes to Add (µL) | | | |
|---|---|---|---|---|---|---|---|
| | rHSA (mg/mL) | Buffer (mM) | Na+ (mM) | rHSA (50 mg/mL) | Buffer stock* | NaCl (1M) | Water |
| pH 6.4, 50 mM NaCl | 10 | 0 | 50 | 20 | 0.0 | 35.0 | 765.0 |
| pH 6.4, 150 mM NaCl | 10 | 0 | 150 | 20 | 0.0 | 135.0 | 665.0 |
| pH 6.4, 200 mM NaCl | 10 | 0 | 200 | 20 | 0.0 | 185.0 | 615.0 |
| pH 6.4, 250 mM NaCl | 10 | 0 | 250 | 200 | 0.0 | 235.0 | 565.0 |
| pH 6.4, 300 mM NaCl | 10 | 0 | 300 | 200 | 0.0 | 285.0 | 515.0 |
| pH 6.4, 400 mM NaCl | 10 | 0 | 400 | 200 | 0.0 | 385.0 | 415.0 |
| pH 6.4, 50 mM NaH$_2$PO$_4$, 50 mM Na | 10 | 50 | 92 | 200 | 50 | 0.0 | 750.0 |
| pH 6.4, 50 mM NaH$_2$PO$_4$, 150 mM Na | 10 | 50 | 150 | 200 | 50 | 57.8 | 692.2 |
| pH 6.4, 50 mM NaH$_2$PO$_4$, 200 mM Na | 10 | 50 | 200 | 200 | 50 | 107.8 | 642.2 |
| pH 6.4, 50 mM NaH$_2$PO$_4$, 250 mM Na | 10 | 50 | 250 | 200 | 50 | 157.8 | 592.2 |
| pH 6.4, 50 mM NaH$_2$PO$_4$, 400 mM Na | 10 | 50 | 400 | 200 | 50 | 307.8 | 442.2 |
| pH 6.4, 50 mM Acetate, 50 mM Na | 10 | 50 | 65 | 200 | 50 | 0 | 750.0 |
| pH 6.4, 50 mM Acetate, 150 mM Na | 10 | 50 | 150 | 200 | 50 | 85.0 | 665.0 |
| pH 6.4, 50 mM Acetate, 200 mM Na | 10 | 50 | 200 | 200 | 50 | 135.0 | 615.0 |
| pH 6.4, 50 mM Acetate, 250 mM Na | 10 | 50 | 250 | 200 | 50 | 185.0 | 565.0 |
| pH 6.4, 50 mM Acetate, 400 mM Na | 10 | 50 | 400 | 200 | 50 | 335.0 | 415.0 |
| pH 6.4, 50 mM Citrate, 50 mM Na | 10 | 50 | 165 | 200 | 150.1 | 0 | 649.9 |
| pH 6.4, 50 mM Citrate, 150 mM Na | 10 | 50 | 200 | 200 | 150.1 | 35.0 | 614.9 |
| pH 6.4, 50 mM Citrate, 200 mM Na | 10 | 50 | 250 | 200 | 150.1 | 85.0 | 564.9 |
| pH 6.4, 50 mM Citrate, 250 mM Na | 10 | 50 | 350 | 200 | 150.1 | 185.0 | 464.9 |
| pH 6.4, 50 mM Citrate, 400 mM Na | 10 | 50 | 500 | 200 | 150.1 | 335.0 | 314.9 |

*Buffer stocks were as per Table 17

Sodium phosphate is a good pH buffer, but as a donator for sodium for stabilization there are better donators and therefore it may be advantageous to combine sodium phosphate with another donator of cation (sodium or other cation) to stabilize albumin.

Consequently, the inventors believe that the buffer in the formulation is not particularly important and any buffer, or no buffer, can be used. However, if the buffer is chelating then the anion present from the buffer should not be included in the calculation of the required concentration of anion.

Example 9

Effect of High Salt Concentration on Stability of Albumin Variants

Method:

Various albumins and variants (Table 19) were diluted with 0.5 M sodium phosphate buffer (pH 6.5). The variants were mature HSA (SEQ ID No: 2) with point mutations (K573P, K500A, K573Y, K573W) and mouse serum albumin (MSA, SEQ ID No: 19). The rHSA concentration and sodium ion concentration of the stock solutions of the albumin variants are provided in Table 20.

TABLE 19

| Albumin Variant | Stock Volumes Added (mL) | | | Sample details | | | |
|---|---|---|---|---|---|---|---|
| | Albumin ** | Phosphate (0.5M, pH 6.5)*** | Water | Albumin (mg/mL) | Phosphate (mM) | Na (mM) | Actual pH |
| HSA-K573P | 3.00 | 1.572 | 1.716 | 50.0 | 125 | 256 | 6.50 |
| HSA-K500A | 3.00 | 1.450 | 1.350 | 50.0 | 125 | 261 | 6.49 |
| HSA-K573Y | 4.50 | 1.710 | 0.650 | 50.0 | 125 | 281 | 6.49 |
| HSA-K573W | 4.50 | 1.520 | 0.073 | 50.0 | 125 | 293 | 6.51 |
| HSA-K573H | 4.00 | 1.750 | 1.250 | 50.0 | 125 | 269 | 6.50 |
| HSA-K573F | 4.00 | 1.640 | 0.900 | 50.0 | 125 | 276 | 6.50 |
| HSA-wild-type* | 2.50 | 1.250 | 1.250 | 50.0 | 125 | 263 | 6.50 |
| MSA-wild-type | 3.00 | 1.440 | 1.310 | 50.0 | 125 | 262 | 6.48 |

*HSA wild-type was spiked with 5 μL 2M octanoate (equivalent to 4 mM octanoate, 100 g/L)
** Albumin: see Table 20
***Phosphate (0.5M, pH 6.5) is described in Table 20b

TABLE 20

| | rHSA Conc (mg/mL) | Na (mM) |
|---|---|---|
| K573P Stock | 104.8 | 145 |
| K500A Stock | 96.7 | 145 |
| K573Y Stock | 76.2 | 145 |
| K573W Stock | 67.7 | 145 |
| K573H Stock | 87.5 | 145 |
| K573F Stock | 81.8 | 145 |
| HSA Wild-type | 100 | 150 |
| Mouse | 95.8 | 145 |

TABLE 20b

| Buffer Stock Solution | Make up Vol (mL) | $NaH_2PO_4 \cdot 2H_2O$ (g) | 27% NaOH (mL) | Sodium Phosphate (mM) | Na (mM) |
|---|---|---|---|---|---|
| 0.5M Sodium Phosphate pH 6.5 | 250 | 19.50 | 7.0 | 500 | 746 |

As all the variants had been purified slightly differently to the wild type human albumin, the levels of octanoate present would have been slightly different for each variant. From previous results, it was estimated that the octanoate present in the variants would have been equivalent to ~4 mM at 100 g/L albumin. As the wild-type stock had negligible levels of octanoate present, this stock was subsequently spiked with 5 μL of 2 M octanoate into the final volume to give an approximately equivalent concentration of octanoate, relative to the variant albumins.

The albumin stocks and a 1 M NaCl stock were used according to Table 21, each sample being made to a final volume of 1 mL in a polystyrene cuvette (Sarstedt 10×4×45 mm). The samples were gently mixed prior to the cuvettes being placed into a temperature controlled spectrophotometer that had been pre-equilibrated and controlled at 65° C.

The absorbance at 350 nm, referenced against an empty cuvette, was then monitored over a 2 hour period with a reading taken every 30 seconds. The data was processed by taking the first 9 data points (~the first 4 minutes), calculating the mean (average) and then subtracting this from all data points in order to give a baseline absorbance. The time taken for the absorbance to then increase by 0.1 AU above this baseline was recorded for that particular formulation sample. If the absorbance did not go above 0.1 AU in 2 hours (7200 seconds) then the data was extrapolated in order to get and approximate time.

A six cuvette holder in the spectrophotometer was used with the first sample always a control and the other five samples using an increasing excipient concentration. The control was always a pH 6.5 sample containing 250 mM NaCl, this needed to remain in solution with no insoluble aggregates over the full 2 hour 65° C. incubation for the test to be considered to be valid.

TABLE 21

| Sample | Albumin Variant | Actual concentration | | | Stock Volumes to Add (µL) | | |
|---|---|---|---|---|---|---|---|
| | | rHSA (mg/mL) | Phosphate (mM) | Na (mM) | Albumin* | NaCl (1M) | Water |
| 1 | K573P | 10 | 25 | 51 | 200.0 | 0.0 | 800.0 |
| 2 | K573P | 10 | 25 | 150 | 200.0 | 98.9 | 701.1 |
| 3 | K573P | 10 | 25 | 200 | 200.0 | 148.9 | 651.1 |
| 4 | K573P | 10 | 25 | 250 | 200.0 | 198.9 | 601.1 |
| 5 | K573P | 10 | 25 | 400 | 200.0 | 348.9 | 451.1 |
| 6 | K500A | 10 | 25 | 52 | 199.9 | 0.0 | 800.1 |
| 7 | K500A | 10 | 25 | 150 | 199.9 | 97.7 | 702.3 |
| 8 | K500A | 10 | 25 | 200 | 199.9 | 147.7 | 652.3 |
| 9 | K500A | 10 | 25 | 250 | 199.9 | 197.7 | 602.3 |
| 10 | K500A | 10 | 25 | 400 | 199.9 | 347.7 | 452.3 |
| 11 | K573Y | 10 | 25 | 56 | 200.1 | 0.1 | 799.8 |
| 12 | K573Y | 10 | 25 | 150 | 200.1 | 93.8 | 706.2 |
| 13 | K573Y | 10 | 25 | 200 | 200.1 | 143.8 | 656.2 |
| 14 | K573Y | 10 | 25 | 250 | 200.1 | 193.8 | 606.2 |
| 15 | K573Y | 10 | 25 | 400 | 200.1 | 343.8 | 456.2 |
| 16 | K573W | 10 | 25 | 59 | 200.0 | 0.0 | 800.0 |
| 17 | K573W | 10 | 25 | 150 | 200.0 | 91.4 | 708.6 |
| 18 | K573W | 10 | 25 | 200 | 200.0 | 141.4 | 658.6 |
| 19 | K573W | 10 | 25 | 250 | 200.0 | 191.4 | 608.6 |
| 20 | K573W | 10 | 25 | 400 | 200.0 | 341.4 | 458.6 |
| 21 | K573H | 10 | 25 | 54 | 200.0 | 0.0 | 800.0 |
| 22 | K573H | 10 | 25 | 150 | 200.0 | 96.1 | 703.9 |
| 23 | K573H | 10 | 25 | 200 | 200.0 | 146.1 | 653.9 |
| 24 | K573H | 10 | 25 | 250 | 200.0 | 196.1 | 603.9 |
| 25 | K573H | 10 | 25 | 400 | 200.0 | 346.1 | 453.9 |
| 26 | K573F | 10 | 25 | 55 | 199.9 | 0.0 | 800.1 |
| 27 | K573F | 10 | 25 | 150 | 199.9 | 94.9 | 705.2 |
| 28 | K573F | 10 | 25 | 200 | 199.9 | 144.9 | 655.2 |
| 29 | K573F | 10 | 25 | 250 | 199.9 | 194.9 | 605.2 |
| 30 | K573F | 10 | 25 | 400 | 199.9 | 344.9 | 455.2 |
| 31 | HSA Wild-type | 10 | 25 | 53 | 200.0 | 0.0 | 800.0 |
| 32 | HSA Wild-type | 10 | 25 | 150 | 200.0 | 97.3 | 702.7 |
| 33 | HSA Wild-type | 10 | 25 | 200 | 200.0 | 147.3 | 652.7 |
| 34 | HSA Wild-type | 10 | 25 | 250 | 200.0 | 197.3 | 602.7 |
| 35 | HSA Wild-type | 10 | 25 | 400 | 200.0 | 347.3 | 452.7 |
| 36 | Mouse | 10 | 25 | 52 | 200.1 | 0.0 | 799.9 |
| 37 | Mouse | 10 | 25 | 150 | 200.1 | 97.5 | 702.4 |
| 38 | Mouse | 10 | 25 | 200 | 200.1 | 147.5 | 652.4 |
| 39 | Mouse | 10 | 25 | 250 | 200.1 | 197.5 | 602.4 |
| 40 | Mouse | 10 | 25 | 400 | 200.1 | 347.5 | 452.4 |

*Albumin concentration is provided in Table 20.

Figure 17:
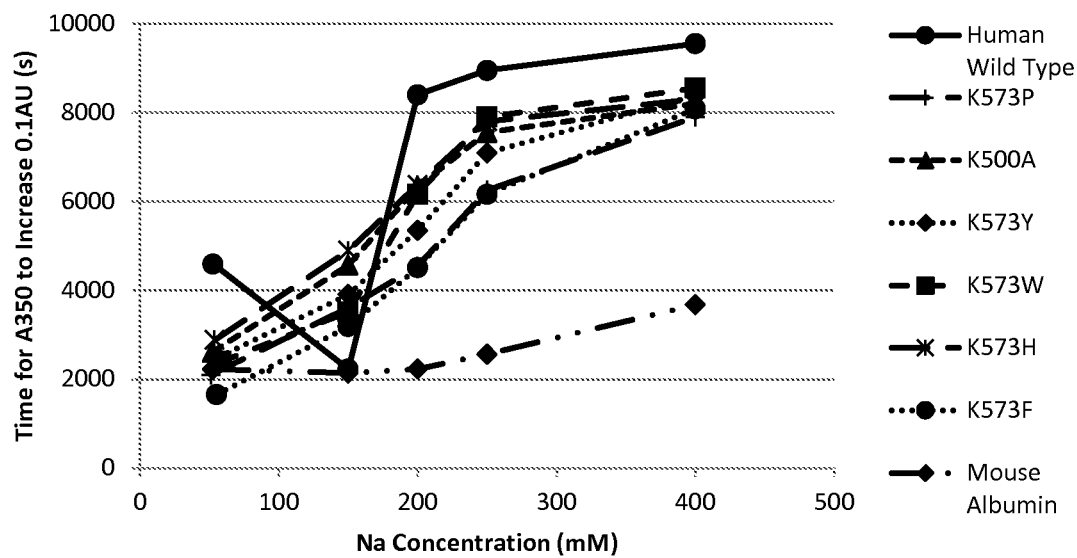
FIG. 17 shows the effect of sodium ion concentration on the stability of different albumins and albumin variants as determined by the time taken (seconds) for the absorbance (A350) to increase by 0.1 AU.
Figure 18:
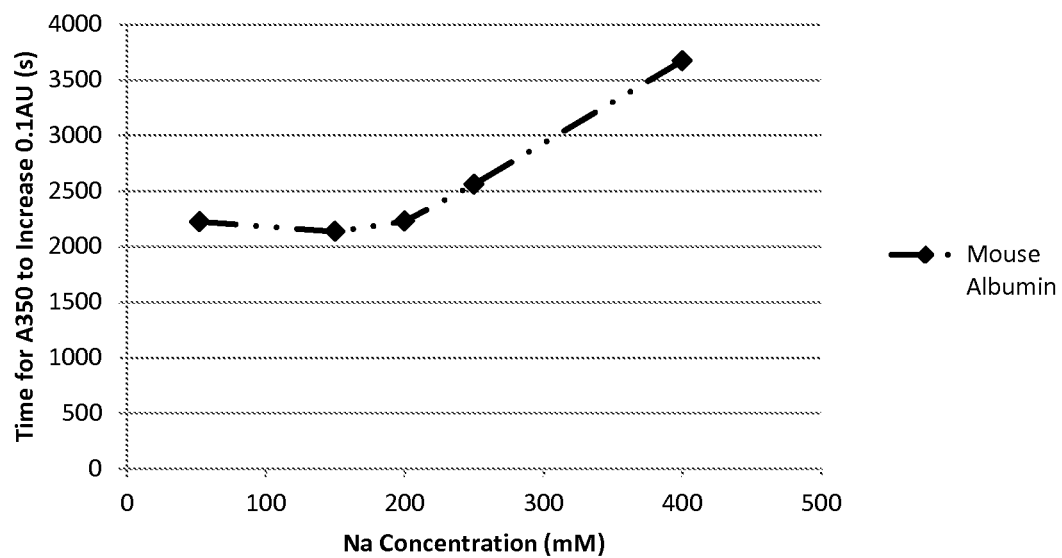
FIG. 18 shows the effect of sodium ion concentration on the stability of mouse serum albumin as determined by the time taken (seconds) for the absorbance (A350) to increase by 0.1 AU.

Results:

All controls were valid. FIGS. 17 and 18 shows the effect of sodium ion concentration on the time taken for the A350 absorbance to increase by 0.1 AU above the base line.

Conclusions:

All points follow a trend apart from the wild type albumin, 150 mM sodium sample. It is unclear why this point is out of trend but is likely to be an outlier and does not detract from the overall conclusions.

For all albumin variants there is a clear trend of increasing albumin stability with increasing sodium concentration.

Mature mouse serum albumin (SEQ ID No: 19) is 72.1% identical (using the algorithim described herein) to mature wild-type human serum albumin (SEQ ID NO: 2) and even though the overall stability was not as high as HSA, or HSA variants, there was still a clear trend of increasing stability with increasing sodium concentration at and above 200 mM.

It is difficult to say whether or not there is a significant difference in stability between the different variants because it is difficult to compare the stabilities of the variants to the stability of wild type albumin since the base formulation with respect to the level of octanoate present was not absolutely controlled to be the same between each variant. However, within the data sets for each variant the level of octanoate will be the same and therefore the increase in stability can only be due to the increasing level of sodium.

The one sample where the octanoate was known (wild type human serum albumin, equivalent to 4 mM at 100 g/L albumin) shows that the observed stability increase with sodium is also valid at this level of octanoate.

Example 10

Effect of pH on Albumin Stability

Method:

A sample of purified albumin containing low octanoate (~0.2 mM, 100 g/L albumin) was diluted initially to 50 mg/mL according to Table 22, using phosphate stocks according to Table 23.

TABLE 22

| Sample | pH of phosphate buffer | Stock Volumes Added (mL) | | | Final parameters of sample | | |
|---|---|---|---|---|---|---|---|
| | | rHSA (50 mg/mL) | Sodium Phosphate buffer (0.5M)* | Water | rHSA Conc (mg/mL) | Sodium Phosphate (mM) | Na (mM) |
| 1 | pH 5.0 | 2.50 | 1.25 | 1.25 | 50.0 | 125 | 204 |
| 2 | pH 6.5 | 2.50 | 1.25 | 1.25 | 50.0 | 125 | 261 |
| 3 | pH 7.0 | 2.50 | 1.25 | 1.25 | 50.0 | 125 | 288 |
| 4 | pH 8.0 | 2.50 | 1.25 | 1.25 | 50.0 | 125 | 318 |

*Sodium phosphate buffer stock solutions are described in Table 23

TABLE 23

| Buffer Stock Solution | Components (made up to a final volume of 250 mL with water) | | Buffer parameters | |
|---|---|---|---|---|
| | $NaH_2PO_4 \cdot 2H_2O$ (g) | 27% NaOH (mL) | Phosphate (mM) | Na Molarity (mM) |
| 0.5M Phosphate pH 5 | 19.50 | 0.5 | 500 | 518 |
| 0.5M Phosphate pH 6 | 19.51 | 3.8 | 500 | 634 |
| 0.5M Phosphate pH 7 | 19.50 | 10.0 | 500 | 851 |
| 0.5M Phosphate pH 8 | 19.50 | 13.4 | 500 | 970 |
| 0.5M Phosphate pH 6.5 | 19.50 | 7.0 | 500 | 746 |

The samples were pH adjusted with 0.5 M HCl (i.e. no added sodium) to give final pHs of 5.02 and 5.55 using the pH 5 stock, pHs of 6.00 and 6.49 using the pH 6.5 stock, pH of 7.04 using the pH 7 stock and pHs of 7.55 and 7.98 using the pH 8 stock. The amount of HCl added was insignificant and would not have altered the albumin or constituent concentrations.

The stocks were used as detailed below (Table 24), being made to a final volume of 1 mL in a polystyrene cuvette (Sarstedt 10×4×45 mm). The samples were gently mixed prior to the cuvettes being placed into a temperature controlled spectrophotometer that had been pre-equilibrated to and controlled at 65° C. The absorbance at 350 nm, referenced against an empty cuvette, was then monitored over a 2 hour period with a reading taken every 30 seconds. The data was processed by taking the first 9 data points (~the first 4 minutes), calculating the mean (average) and then subtracting this from all data points in order to give a baseline absorbance. The time taken for the absorbance to then increase by 0.1 AU above this baseline was recorded for that particular formulation sample. If the absorbance did not go above 0.1 AU in 2 hours (7200 seconds) then the data was extrapolated in order to get and approximate time.

A six cuvette holder in the spectrophotometer was used with the first sample always being a control and the other five samples using an increasing excipient concentration. The control was always a pH 6.5 sample containing 250 mM NaCl, this needed to remain in solution with no insoluble aggregates over the full 2 hour 65° C. incubation for the test to be considered to be valid.

TABLE 24

| Sample | | Actual Final | | | | Stock Volumes to Add (μL) | | |
|---|---|---|---|---|---|---|---|---|
| Number | pH | Na (mM) | Vol (μL) | rHSA (mg/mL) | Phosphate (mM) | Na (mM) | rHSA (50 mg/mL)* | NaCl (1M) | Water |
| 1 | 6.49 | 50 | 1000 | 10 | 25 | 52 | 200.0 | 0.0 | 800.0 |
| 2 | 6.49 | 150 | 1000 | 10 | 25 | 150 | 200.0 | 97.7 | 702.3 |
| 3 | 6.49 | 200 | 1000 | 10 | 25 | 200 | 200.0 | 147.7 | 652.3 |
| 4 | 6.49 | 250 | 1000 | 10 | 25 | 250 | 200.0 | 197.7 | 602.3 |
| 5 | 6.49 | 400 | 1000 | 10 | 25 | 400 | 200.0 | 347.7 | 452.3 |
| 6 | 5.02 | 50 | 1000 | 10 | 25 | 50 | 200.0 | 9.1 | 790.9 |
| 7 | 5.02 | 150 | 1000 | 10 | 25 | 150 | 200.0 | 109.1 | 690.9 |
| 8 | 5.02 | 200 | 1000 | 10 | 25 | 200 | 200.0 | 159.1 | 640.9 |
| 9 | 5.02 | 250 | 1000 | 10 | 25 | 250 | 200.0 | 209.1 | 590.9 |
| 10 | 5.02 | 400 | 1000 | 10 | 25 | 400 | 200.0 | 359.1 | 440.9 |
| 11 | 5.55 | 50 | 1000 | 10 | 25 | 50 | 200.0 | 9.1 | 790.9 |
| 12 | 5.55 | 150 | 1000 | 10 | 25 | 150 | 200.0 | 109.1 | 690.9 |
| 13 | 5.55 | 200 | 1000 | 10 | 25 | 200 | 200.0 | 159.1 | 640.9 |
| 14 | 5.55 | 250 | 1000 | 10 | 25 | 250 | 200.0 | 209.1 | 590.9 |
| 15 | 5.55 | 400 | 1000 | 10 | 25 | 400 | 200.0 | 359.1 | 440.9 |
| 16 | 6.00 | 50 | 1000 | 10 | 25 | 52 | 200.0 | 0.0 | 800.0 |
| 17 | 6.00 | 150 | 1000 | 10 | 25 | 150 | 200.0 | 97.7 | 702.3 |
| 18 | 6.00 | 200 | 1000 | 10 | 25 | 200 | 200.0 | 147.7 | 652.3 |
| 19 | 6.00 | 250 | 1000 | 10 | 25 | 250 | 200.0 | 197.7 | 602.3 |
| 20 | 6.00 | 400 | 1000 | 10 | 25 | 400 | 200.0 | 347.7 | 452.3 |
| 21 | 7.04 | 50 | 1000 | 10 | 25 | 58 | 200.0 | 0.0 | 800.0 |
| 22 | 7.04, | 150 | 1000 | 10 | 25 | 150 | 200.0 | 92.5 | 707.6 |
| 23 | 7.04 | 200 | 1000 | 10 | 25 | 200 | 200.0 | 142.5 | 657.6 |
| 24 | 7.04 | 250 | 1000 | 10 | 25 | 250 | 200.0 | 192.5 | 607.6 |
| 25 | 7.04 | 400 | 1000 | 10 | 25 | 400 | 200.0 | 342.5 | 457.6 |
| 26 | 7.55 | 50 | 1000 | 10 | 25 | 64 | 200.0 | 0.0 | 800.0 |

TABLE 24-continued

| Sample | | | Actual Final | | | Stock Volumes to Add (μL) | | | |
|---|---|---|---|---|---|---|---|---|---|
| Number | pH | Na (mM) | Vol (μL) | rHSA (mg/mL) | Phosphate (mM) | Na (mM) | rHSA (50 mg/mL)* | NaCl (1M) | Water |
| 27 | 7.55 | 150 | 1000 | 10 | 25 | 150 | 200.0 | 86.5 | 713.5 |
| 28 | 7.55 | 200 | 1000 | 10 | 25 | 200 | 200.0 | 136.5 | 663.5 |
| 29 | 7.55 | 250 | 1000 | 10 | 25 | 250 | 200.0 | 186.5 | 613.5 |
| 30 | 7.55 | 400 | 1000 | 10 | 25 | 400 | 200.0 | 336.5 | 463.5 |
| 31 | 7.98 | 50 | 1000 | 10 | 25 | 64 | 200.0 | 0.0 | 800.0 |
| 32 | 7.98 | 150 | 1000 | 10 | 25 | 150 | 200.0 | 86.5 | 713.5 |
| 33 | 7.98 | 200 | 1000 | 10 | 25 | 200 | 200.0 | 136.5 | 663.5 |
| 34 | 7.98 | 250 | 1000 | 10 | 25 | 250 | 200.0 | 186.5 | 613.5 |
| 35 | 7.98 | 400 | 1000 | 10 | 25 | 400 | 200.0 | 336.5 | 463.5 |

*Albumin stocks are described in Table 23.

For the pH 7 (measure pH 7.04), 7.5 (measured pH 7.55) and 8 (measure pH 7.98) samples the stabilizing effect of the sodium was inconclusive when measuring insoluble aggregates as detected by the A350 nm absorbance increase. Therefore after the 2 hour incubation at 65° C. incubation in the spectrophotometer the samples were removed, centrifuged to remove any large particles and the samples analyzed for soluble aggregates by GP-HPLC (as per Example 4). The data was expressed as % monomeric albumin remaining (the higher the value the more stable the formulation).

Figure 19:
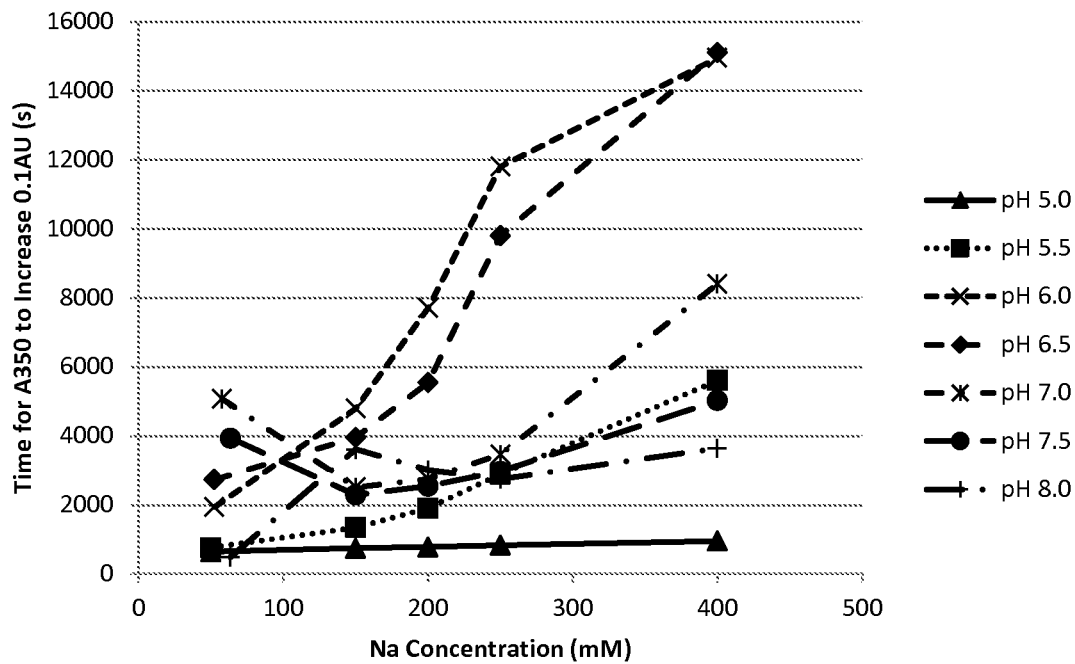
FIG. 19 shows the effect of pH and sodium ion concentration on albumin stability as determined by the time taken (seconds) for the absorbance (A350) to increase by 0.1 AU.
Figure 20:
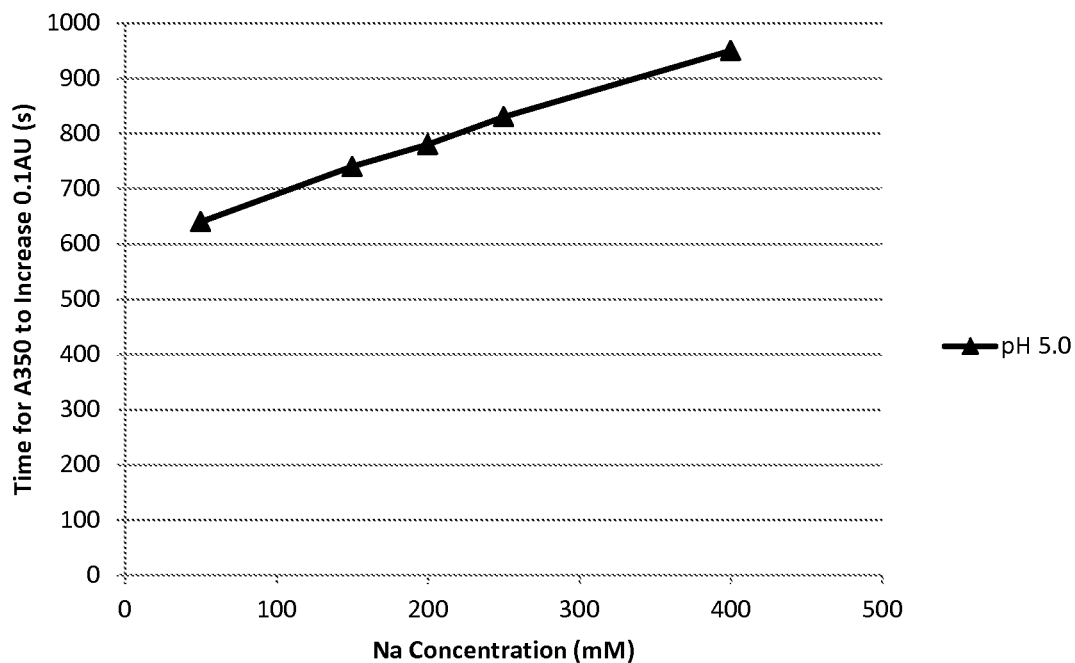
FIG. 20 shows the effect of sodium ion concentration on albumin stability at pH 5.0 as determined by the time taken (seconds) for the absorbance (A350) to increase by 0.1 AU.
Figure 21:
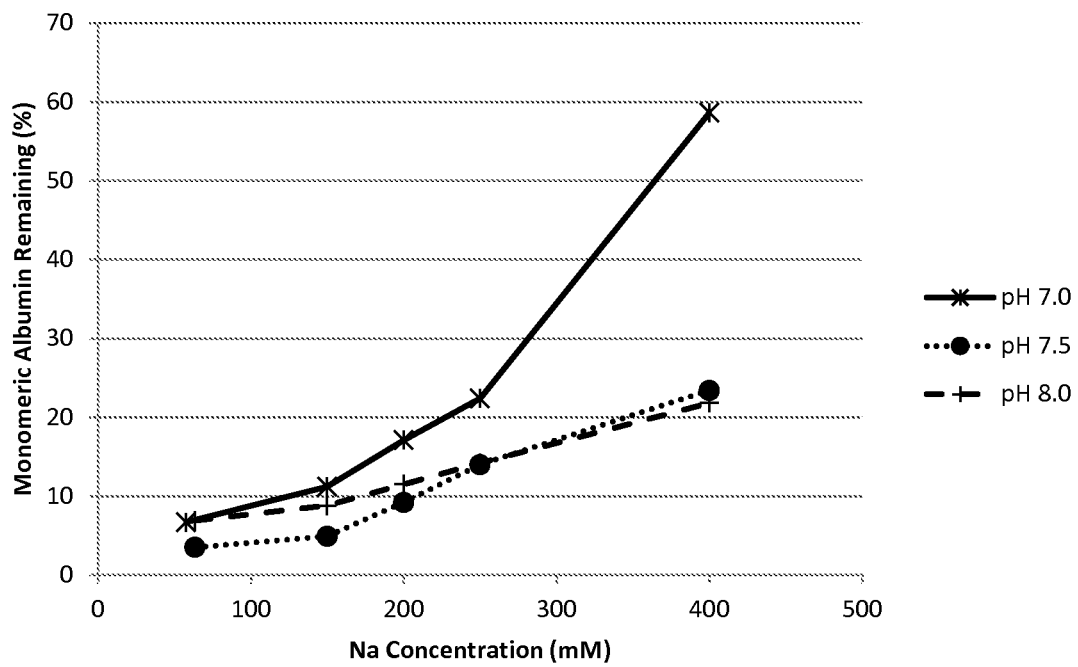
FIG. 21 shows the effect of sodium ion concentration on albumin stability at pH 7.0, 7.5 and 8.0 as determined by the remaining monomer content following incubation at 65° C. for 2 hours.

Results:

All controls were valid. FIGS. 19, 20 and 21 show the stability of albumin relative to sodium ion concentration. The results for the pH 6.5 controls run at the same time as the pH7, 7.5 and 8 samples gave a mean of 82% monomer content.

Conclusions:

For all pHs from pH 5 to pH 6.5 it was clear that there was an increase in albumin stability with increasing albumin concentration as measured by the A350 absorbance increase (insoluble aggregates).

At pHs 7, 7.5 and 8 the trend was not clear (FIG. 19) with a possible dip in stability around 150 mM Na. However, when these samples were analyzed by GP-HPLC for soluble aggregates and % monomer remaining (FIG. 21) there was a clear trend of increasing stability with increasing sodium. The reason that this trend was not observed for the insoluble aggregates may be due to the fact that these pHs are the furthest from the pI of albumin (5.2 for albumin) and therefore they are less likely to precipitate with the aggregates coming out of solution.

The pH 6.5 controls had higher levels of monomer remaining at the same sodium ion concentration (250 mM) than any of the higher pHs showing that pH 6.5 is the more stable pH for albumin.

Combining both the insoluble and soluble aggregate data shows that increasing sodium concentration increases albumin stability from pH 5 to pH 8.

Example 11

Effect of Octanoate on Stem Cell Cultures

Method:

The effect of octanoate on stem cell culture was carried out by a contract research organization: Cellartis AB (Gothenburg, Sweden). Briefly, albumin at 100 g/L with varying levels of octanoate (0.2, 0.5, 1.0 and 8.0 mM) was used as the albumin supplement in standard stem cell culture media. Human embryonic stem cells (cell lines SA121 and SA181 (Cellartis AB, cell lines deposited in the European Human Embryonic Stem Cell Registry)) were transferred from their standard media and grown through 5 passages in 6 well plates in the media supplemented with the albumin containing varying levels of octanoate. The cell growth over the 5 passages was assessed by monitoring the cell doubling times during consecutive passages in cell production. The doubling times of cultures should be within a range of 28-40 hours, and can be seen as a trend indicator. In order to determine the undifferentiation state of the cells after 5 passages in albumin supplemented media, antibodies against four different accepted markers for the undifferentiated state, namely Oct-4, SSEA-3, Tra-160 and hES-Cellect, were used for immunostaining.

Results:

Table 25 shows data for the doubling time. The initial doubling times are quite high, probably due to cells needing to adjust to the new culture medium composition. However, the doubling times between passages 2 and 4 are all within expected range except for the sample containing 8 mM octanoate which failed to maintain acceptable cell attachment and could not be continued past passage 2 even with modified medium and coating conditions. Doubling times for passage 5 were highly variable and for some samples lay considerably outside the standard range. However, it is difficult to draw conclusions as cultures were not expanded further.

TABLE 25

Doubling time in hours for each of the cell lines over five passages. Doubling time is presented in hours, and formula used is Td(h) = T * LOG2/LOG(cells harvested/cells seeded). T = time in hours between passages

| Cell line | Octanoate Present (mM) | Passage 1 | Passage 2 | Passage 3 | Passage 4 | Passage 5 |
|---|---|---|---|---|---|---|
| SA121 | 0.2 | 45.6 | 31.7 | 35.8 | 33.8 | 56.1 |
| | 0.5 | 44.5 | 36.5 | 42.3 | 44.9 | 30.4 |
| | 1.0 | 65.5 | 33.4 | 31.2 | 30.4 | 38.7 |
| | 8.0 | 61.8 | 46.0 | — | — | — |
| SA181 | 0.2 | 88.5 | 31.9 | 31.5 | 29.5 | 452 |
| | 0.5 | 144.0 | 34.3 | 37.3 | 29.0 | 134 |
| | 1.0 | 47.1 | 32.8 | 36.9 | 31.4 | 59.4 |
| | 8.0 | 117 | 89.7 | — | — | — |

Table 26 shows data for the immunocytochemical stainings for differentiation markers and shows that all the samples (except the sample containing 8 mM octanoate, since it did not reach 5 passages) supported cultures to maintain an undifferentiated state for the 5 passages tested.

TABLE 26

Summary of immunocytochemical staining performed on cells stained using antibodies against Oct-4, Tra-1 60, SSEA-3, hES-Cellect™ and SSEA-1.

| Cell line | Octanoate Present (mM) | Oct-4 | Tra-1 60 | SSEA-3 | hES-Cellect™ | SSEA-1 |
|---|---|---|---|---|---|---|
| SA121 | 0.2 | +++ | +++ | +++ | +++ | − |
| | 0.5 | +++ | +++ | +++ | +++ | − |
| | 1.0 | +++ | +++ | +++ | +++ | − |
| SA181 | 0.2 | +++ | +++ | +++ | +++ | − |
| | 0.5 | +++ | +++ | +++ | +++ | − |
| | 1.0 | +++ | +++ | +++ | +++ | − |

(+++) represents good staining and easy to detect, while (−) represents no staining detectable.

Conclusions:

The octanoate level present in the albumin is important for stem cell attachment, maintenance of undifferentiated cell growth. At 8 mM octanoate in 100 g/L albumin the octanoate is toxic to stem cells and does not allow their attachment to surfaces or cell growth.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An albumin formulation comprising:
   50 to 400 g·L$^{-1}$ of an albumin or a variant thereof, wherein said albumin consists of the amino acid sequence of SEQ ID NO: 2, and wherein said variant thereof consists of the amino acid sequence of SEQ ID NO: 2 having one or more amino acid substitutions and having at least 98% sequence identity to SEQ ID NO: 2,
   a solvent, and,
   200 mM or higher concentration of cations,
   wherein said formulation has a pH from about 6.0 to about 7.0,
   wherein the solvent is inorganic solvent, inorganic buffer, or organic buffer, and
   wherein the concentration of octanoate in said formulation is less than or equal to 1 mM octanoate.

2. The albumin formulation according to claim 1 wherein the cations are present at from 200 to 1000 mM.

3. The albumin formulation according to claim 2 wherein the cations are present at from 200 to 350 mM.

4. The albumin formulation according to claim 1 wherein the pH is about pH 6.5.

5. The albumin formulation according to claim 1 wherein the cations are selected from: sodium, potassium, calcium, magnesium, and ammonium.

6. The albumin formulation according to claim 1 wherein the cations are sodium ions.

7. The albumin formulation according to claim 6 which is substantially free of amino acids and/or substantially free of detergent.

8. The albumin formulation according to claim 1 which comprises:
   (a) less than 5 mM amino acids; and/or
   (b) less than 20 mg·L$^{-1}$ detergent.

9. The albumin formulation according to claim 1, wherein the albumin is HSA of SEQ ID NO: 2.

10. The albumin formulation according to claim 1 wherein the albumin is at a concentration of from 50 g·L$^{-1}$ to 250 g·L$^{-1}$.

11. The albumin formulation according to claim 1 wherein the albumin is a recombinant albumin.

12. The albumin formulation according to claim 1 comprising:
   (a) 50 to 250 g·L$^{-1}$ albumin;
   (b) 225 to 275 mM Na$^{30}$;
   (c) 20 to 30 mM phosphate;
   and having a pH of about 6.5.

13. The albumin formulation according to claim 1 which is substantially free of octanoate.

14. The albumin formulation of claim 1, wherein the albumin formulation is more stable than a control albumin formulation comprising 150 mM Na.

15. The albumin formulation of claim 1, wherein said variant has at least 99% sequence identity to SEQ ID NO: 2.

16. The albumin formulation of claim 1, wherein said variant has one or more point mutations selected from the group consisting of K573P, K573Y, K573W and K500A of SEQ ID NO: 2.

17. A method of culturing cells comprising incubating cells in a culture medium comprising the albumin formulation of claim 1 and a basal medium.

18. The method according to claim 17 in which the cells comprise stem cells.

19. A method of stabilizing albumin or a variant thereof, the method comprising formulating an albumin with a solvent to 50 to 400 g·L$^{-1}$, 200 mM or higher concentration of cations, less than or equal to 1 mM octanoate, at a pH from about 6.0 to about 7.0, wherein the solvent is inorganic solvent, inorganic buffer, or organic buffer, wherein the albumin is human serum albumin (HSA) consisting of the amino acid sequence of SEQ ID NO: 2, and wherein said variant thereof consists of the amino acid sequence of SEQ ID NO: 2 having one or more amino acid substitutions and having at least 98% sequence identity to SEQ ID NO: 2.

\* \* \* \* \*

UNITED STATES PATENT AND TRADEMARK OFFICE
CERTIFICATE OF CORRECTION

Page 1 of 1

PATENT NO. : 10,844,349 B2
APPLICATION NO. : 14/130639
DATED : November 24, 2020
INVENTOR(S) : Sandra Marie Merkel et al.

It is certified that error appears in the above-identified patent and that said Letters Patent is hereby corrected as shown below:

In the Claims

Column 102, Claim 12, Line number 33, please replace "(b) 225 to 275 mM $Na^{30}$;" with --(b) 225 to 275 mM $Na^+$;--.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 19

<210> SEQ ID NO 1
<211> LENGTH: 1758
<212> TYPE: DNA
<213> ORGANISM: Homo sapiens
<220> FEATURE:
<221> NAME/KEY: misc_feature
<222> LOCATION: (1)..(1758)
<223> OTHER INFORMATION: cDNA encoding HSA

<400> SEQUENCE: 1
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca gaagacatcc ttactttat gcccccggaac tccttttctt tgctaaaagg     480
tataaagctg cttttacaga atgttgccaa gctgctgata agctgcctg cctgttgcca     540
```

-continued

```
aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag gcggaccttt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg cagatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gcagcaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg atgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc aaggcaaca    1620
aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttataa                                                 1758
```

<210> SEQ ID NO 2
<211> LENGTH: 585
<212> TYPE: PRT
<213> ORGANISM: Homo sapiens

<400> SEQUENCE: 2

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
```

-continued

```
            145                 150                 155                 160
Tyr Lys Ala Ala Phe Thr Glu Cys Cys Gln Ala Ala Asp Lys Ala Ala
                    165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575
```

```
        Ala Ala Ser Gln Ala Ala Leu Gly Leu
                    580                 585

<210> SEQ ID NO 3
<211> LENGTH: 609
<212> TYPE: PRT
<213> ORGANISM: Homo sapiens

<400> SEQUENCE: 3

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
 50                 55                  60

Lys Leu Val Asn Glu Val Thr Glu Phe Ala Lys Thr Cys Val Ala Asp
 65                 70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
```

```
        355                 360                 365
Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 4
<211> LENGTH: 621
<212> TYPE: PRT
<213> ORGANISM: Pan troglodytes

<400> SEQUENCE: 4

Met Asn Glu Ser Ser Cys Cys Ser Thr Ser Leu Pro Ala Phe Gly Val
1               5                   10                  15

Ser Val Leu Asp Ser Gly His Ser Ser Ser Ala Tyr Ser Arg Gly
                20                  25                  30

Val Phe Arg Arg Asp Ala His Lys Ser Glu Val Ala His Arg Phe Lys
            35                  40                  45

Asp Leu Gly Glu Glu Asn Phe Lys Ala Leu Val Leu Val Ala Phe Ala
        50                  55                  60

Gln Tyr Leu Gln Gln Cys Pro Phe Glu Asp His Val Lys Leu Val Asn
65                  70                  75                  80

Glu Val Thr Glu Phe Ala Lys Thr Cys Val Ala Asp Glu Ser Ala Glu
                85                  90                  95

Asn Cys Asp Lys Ser Leu His Thr Leu Phe Gly Asp Lys Leu Cys Thr
            100                 105                 110

Val Ala Thr Leu Arg Glu Lys Tyr Gly Glu Met Ala Asp Cys Cys Ala
```

-continued

```
            115                 120                 125
Lys Gln Glu Pro Glu Arg Asn Glu Cys Phe Leu Gln His Lys Asp Asp
130                 135                 140

Asn Pro Asn Leu Pro Arg Leu Val Arg Pro Glu Val Asp Val Met Cys
145                 150                 155                 160

Thr Ala Phe His Asp Asn Glu Gly Thr Phe Leu Lys Lys Tyr Leu Tyr
                165                 170                 175

Glu Val Ala Arg Arg His Pro Tyr Phe Tyr Ala Pro Glu Leu Leu Phe
                180                 185                 190

Phe Ala Glu Arg Tyr Lys Ala Ala Phe Thr Glu Cys Cys Gln Ala Ala
                195                 200                 205

Asp Lys Ala Ala Cys Leu Leu Pro Lys Leu Asp Glu Leu Arg Asp Glu
210                 215                 220

Gly Lys Ala Ser Ser Ala Lys Gln Arg Leu Lys Cys Ala Ser Leu Gln
225                 230                 235                 240

Lys Phe Gly Glu Arg Ala Phe Lys Ala Trp Ala Val Ala Arg Leu Ser
                245                 250                 255

Gln Arg Phe Pro Lys Ala Glu Phe Ala Glu Val Ser Lys Leu Val Thr
                260                 265                 270

Asp Leu Thr Lys Val His Thr Glu Cys Cys His Gly Asp Leu Leu Glu
                275                 280                 285

Cys Ala Asp Asp Arg Ala Asp Leu Ala Lys Tyr Ile Cys Glu Asn Gln
290                 295                 300

Asp Ser Ile Ser Ser Lys Leu Lys Glu Cys Cys Glu Lys Pro Leu Leu
305                 310                 315                 320

Glu Lys Ser His Cys Leu Ala Glu Val Glu Asn Asp Glu Met Pro Ala
                325                 330                 335

Asp Leu Pro Ser Leu Ala Ala Asp Phe Val Glu Ser Lys Glu Val Cys
                340                 345                 350

Lys Asn Tyr Ala Glu Ala Lys Asp Val Phe Leu Gly Met Phe Leu Tyr
                355                 360                 365

Glu Tyr Ala Arg Arg His Pro Asp Tyr Ser Val Val Leu Leu Leu Arg
                370                 375                 380

Leu Ala Lys Thr Tyr Glu Thr Thr Leu Glu Lys Cys Cys Ala Ala Ala
385                 390                 395                 400

Asp Pro His Glu Cys Tyr Ala Lys Val Phe Asp Glu Phe Lys Pro Leu
                405                 410                 415

Val Glu Glu Pro Gln Asn Leu Ile Lys Gln Asn Cys Glu Leu Phe Glu
                420                 425                 430

Gln Leu Gly Glu Tyr Lys Phe Gln Asn Ala Leu Leu Val Arg Tyr Thr
                435                 440                 445

Lys Lys Val Pro Gln Val Ser Thr Pro Thr Leu Val Glu Val Ser Arg
450                 455                 460

Asn Leu Gly Lys Val Gly Ser Lys Cys Cys Lys His Pro Glu Ala Lys
465                 470                 475                 480

Arg Met Pro Cys Ala Glu Asp Tyr Leu Ser Val Val Leu Asn Gln Leu
                485                 490                 495

Cys Val Leu His Glu Lys Thr Pro Val Ser Asp Arg Val Thr Lys Cys
                500                 505                 510

Cys Thr Glu Ser Leu Val Asn Arg Arg Pro Cys Phe Ser Ala Leu Glu
                515                 520                 525

Val Asp Glu Thr Tyr Val Pro Lys Glu Phe Asn Ala Glu Thr Phe Thr
530                 535                 540
```

Phe His Ala Asp Ile Cys Thr Leu Ser Glu Lys Glu Arg Gln Ile Lys
545                 550                 555                 560

Lys Gln Thr Ala Leu Val Glu Leu Val Lys His Lys Pro Lys Ala Thr
                565                 570                 575

Lys Glu Gln Leu Lys Ala Val Met Asp Asp Phe Ala Ala Phe Val Glu
            580                 585                 590

Lys Cys Cys Lys Ala Asp Asp Lys Glu Thr Cys Phe Ala Glu Glu Gly
        595                 600                 605

Lys Lys Leu Val Ala Ala Ser Gln Ala Ala Leu Gly Leu
    610                 615                 620

<210> SEQ ID NO 5
<211> LENGTH: 608
<212> TYPE: PRT
<213> ORGANISM: Macaca mulatta

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Asp Thr His Lys Ser Glu Val Ala
            20                  25                  30

His Arg Phe Lys Asp Leu Gly Glu Glu His Phe Lys Gly Leu Val Leu
        35                  40                  45

Val Ala Phe Ser Gln Tyr Leu Gln Gln Cys Pro Phe Glu Glu His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Leu Val Arg Pro Glu Val
    130                 135                 140

Asp Val Met Cys Thr Ala Phe His Asp Asn Glu Ala Thr Phe Leu Lys
145                 150                 155                 160

Lys Tyr Leu Tyr Glu Val Ala Arg Arg His Pro Tyr Phe Tyr Ala Pro
                165                 170                 175

Glu Leu Leu Phe Phe Ala Ala Arg Tyr Lys Ala Ala Phe Ala Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Asp Arg Ala Phe Lys Ala Trp Ala Val
225                 230                 235                 240

Ala Arg Leu Ser Gln Lys Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Ser Lys Leu Lys Glu Cys Cys Asp

```
            290                 295                 300
Lys Pro Leu Leu Glu Lys Ser His Cys Leu Ala Glu Val Glu Asn Asp
305                 310                 315                 320

Glu Met Pro Ala Asp Leu Pro Ser Leu Ala Ala Asp Tyr Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Met
        355                 360                 365

Leu Leu Leu Arg Leu Ala Lys Ala Tyr Glu Ala Thr Leu Glu Lys Cys
    370                 375                 380

Cys Ala Ala Ala Asp Pro His Glu Cys Tyr Ala Lys Val Phe Asp Glu
385                 390                 395                 400

Phe Gln Pro Leu Val Glu Glu Pro Gln Asn Leu Val Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ala Lys Cys Cys Lys Leu
    450                 455                 460

Pro Glu Ala Lys Arg Met Pro Cys Ala Glu Asp Tyr Leu Ser Val Val
465                 470                 475                 480

Leu Asn Arg Leu Cys Val Leu His Glu Lys Thr Pro Val Ser Glu Lys
                485                 490                 495

Val Thr Lys Cys Cys Thr Glu Ser Leu Val Asn Arg Arg Pro Cys Phe
            500                 505                 510

Ser Ala Leu Glu Leu Asp Glu Ala Tyr Val Pro Lys Ala Phe Asn Ala
        515                 520                 525

Glu Thr Phe Thr Phe His Ala Asp Met Cys Thr Leu Ser Glu Lys Glu
    530                 535                 540

Lys Gln Val Lys Lys Gln Thr Ala Leu Val Glu Leu Val Lys His Lys
545                 550                 555                 560

Pro Lys Ala Thr Lys Glu Gln Leu Lys Gly Val Met Asp Asn Phe Ala
                565                 570                 575

Ala Phe Val Glu Lys Cys Cys Lys Ala Asp Asp Lys Glu Ala Cys Phe
            580                 585                 590

Ala Glu Glu Gly Pro Lys Phe Val Ala Ala Ser Gln Ala Ala Leu Ala
        595                 600                 605

<210> SEQ ID NO 6
<211> LENGTH: 608
<212> TYPE: PRT
<213> ORGANISM: Mesocricetus auratus

<400> SEQUENCE: 6

Met Lys Trp Val Thr Phe Leu Leu Leu Phe Val Ser Asp Ser Ala
1               5                   10                  15

Phe Ser Arg Gly Leu Phe Arg Arg Asp Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Phe Leu Gln Lys Cys Pro Tyr Glu Glu His Val
    50                  55                  60
```

-continued

```
Lys Leu Val Asn Glu Val Thr Asp Phe Ala Lys Thr Cys Val Ala Asp
 65                  70                  75                  80

Glu Ser Ala Glu Asn Cys Asp Lys Ser Leu His Thr Leu Phe Gly Asp
             85                  90                  95

Lys Leu Cys Ala Ile Pro Thr Leu Arg Asp Ser Tyr Gly Glu Leu Ala
            100                 105                 110

Asp Cys Cys Ala Lys Lys Glu Pro Glu Arg Asn Glu Cys Phe Leu Lys
        115                 120                 125

His Lys Asp Asp His Pro Asn Leu Pro Pro Phe Val Arg Pro Asp Ala
    130                 135                 140

Glu Ala Met Cys Thr Ser Phe Gln Glu Asn Ala Val Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Ser Ala Ile Met Thr Glu Cys
            180                 185                 190

Cys Gly Glu Ala Asp Lys Ala Ala Cys Ile Thr Pro Lys Leu Asp Ala
        195                 200                 205

Leu Lys Glu Lys Ala Leu Ala Ser Ser Val Asn Gln Arg Leu Lys Cys
    210                 215                 220

Ser Ser Leu Gln Arg Phe Gly Gln Arg Ala Phe Lys Ala Trp Ala Val
225                 230                 235                 240

Ala Arg Met Ser Gln Lys Phe Pro Lys Ala Asp Phe Ala Glu Ile Thr
                245                 250                 255

Lys Leu Ala Thr Asp Leu Thr Lys Leu Thr Glu Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Ser Ile Ser Ser Lys Leu Gln Ala Cys Cys Asp
    290                 295                 300

Lys Pro Val Leu Lys Lys Ser His Cys Leu Ser Glu Val Glu Asn Asp
305                 310                 315                 320

Asp Leu Pro Ala Asp Leu Pro Ser Leu Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ala Arg Arg His Pro Asp Tyr Ser Val Ala
        355                 360                 365

Leu Leu Leu Arg Leu Ala Lys Lys Tyr Glu Ala Thr Leu Glu Lys Cys
    370                 375                 380

Cys Ala Glu Ala Asp Pro Ser Ala Cys Tyr Gly Lys Val Leu Asp Glu
385                 390                 395                 400

Phe Gln Pro Leu Val Glu Glu Pro Lys Asn Leu Val Lys Ala Asn Cys
                405                 410                 415

Glu Leu Phe Glu Lys Leu Gly Glu Tyr Gly Phe Gln Asn Ala Leu Ile
            420                 425                 430

Val Arg Tyr Thr Gln Lys Ala Pro Gln Val Ser Thr Pro Thr Leu Val
        435                 440                 445

Glu Ala Ala Arg Asn Leu Gly Lys Val Gly Ser Lys Cys Cys Val Leu
    450                 455                 460

Pro Glu Ala Gln Arg Leu Pro Cys Val Glu Asp Tyr Ile Ser Ala Ile
465                 470                 475                 480

Leu Asn Arg Val Cys Val Leu His Glu Lys Thr Pro Val Ser Glu Gln
```

```
                        485               490               495
    Val Thr Lys Cys Cys Thr Gly Ser Val Val Glu Arg Arg Pro Cys Phe
                    500               505               510
    Ser Ala Leu Pro Val Asp Glu Thr Tyr Val Pro Lys Glu Phe Lys Ala
                    515               520               525
    Glu Thr Phe Thr Phe His Ala Asp Ile Cys Ser Leu Pro Glu Lys Glu
                    530               535               540
    Lys Gln Met Lys Lys Gln Ala Ala Leu Val Glu Leu Val Lys His Lys
    545               550               555               560
    Pro Lys Ala Thr Gly Pro Gln Leu Arg Thr Val Leu Gly Glu Phe Thr
                    565               570               575
    Ala Phe Leu Asp Lys Cys Cys Lys Ala Glu Asp Lys Glu Ala Cys Phe
                    580               585               590
    Ser Glu Asp Gly Pro Lys Leu Val Ala Ser Ser Gln Ala Ala Leu Ala
                    595               600               605
```

<210> SEQ ID NO 7
<211> LENGTH: 608
<212> TYPE: PRT
<213> ORGANISM: Cavia porcellus

<400> SEQUENCE: 7

```
    Met Lys Trp Val Thr Phe Ile Ser Leu Leu Phe Leu Phe Ser Ser Val
    1               5                   10                  15
    Tyr Ser Arg Gly Val Phe Arg Arg Glu Ala His Lys Ser Glu Ile Ala
                    20                  25                  30
    His Arg Phe Asn Asp Leu Gly Glu Gly His Phe Lys Gly Leu Val Leu
                    35                  40                  45
    Ile Thr Leu Ser Gln His Leu Gln Lys Ser Pro Phe Glu Glu His Val
                    50                  55                  60
    Lys Leu Val Asn Glu Val Thr Asp Phe Ala Lys Ala Cys Val Ala Asp
    65                  70                  75                  80
    Glu Ser Ala Gln Asn Cys Gly Lys Ala Ile Ala Thr Leu Phe Gly Asp
                    85                  90                  95
    Lys Val Cys Ala Ile Pro Ser Leu Arg Glu Thr Tyr Gly Glu Leu Ala
                    100                 105                 110
    Asp Cys Cys Ala Lys Glu Asp Pro Asp Arg Val Glu Cys Phe Leu Gln
                    115                 120                 125
    His Lys Asp Asp Asn Pro Asn Leu Pro Pro Phe Glu Arg Pro Glu Pro
                    130                 135                 140
    Glu Ala Leu Cys Thr Ala Phe Lys Glu Asn Asn Asp Arg Phe Ile Gly
    145                 150                 155                 160
    His Tyr Leu Tyr Glu Val Ser Arg Arg His Pro Tyr Phe Tyr Ala Pro
                    165                 170                 175
    Glu Leu Leu Tyr Tyr Ala Glu Lys Tyr Lys Asn Ala Leu Thr Glu Cys
                    180                 185                 190
    Cys Glu Ala Ala Asp Lys Ala Ala Cys Leu Thr Pro Lys Leu Asp Ala
                    195                 200                 205
    Ile Lys Glu Lys Ala Leu Val Ser Ser Ala Gln Gln Arg Leu Lys Cys
                    210                 215                 220
    Ala Ser Leu Gln Lys Phe Gly Glu Arg Ala Phe Lys Ala Trp Ser Val
    225                 230                 235                 240
    Ala Arg Leu Ser Gln Lys Phe Pro Lys Ala Glu Phe Ala Glu Ile Ser
                    245                 250                 255
```

-continued

Thr Ile Val Thr Ser Leu Thr Lys Val Thr Lys Glu Cys Cys His Gly
            260                 265                 270

Asp Leu Leu Glu Cys Ala Asp Asp Arg Gln Glu Leu Ala Lys Tyr Met
        275                 280                 285

Cys Glu His Gln Asp Ser Ile Ser Ser Lys Leu Lys Glu Cys Cys Val
    290                 295                 300

Lys Pro Thr Leu Gln Lys Ala His Cys Ile Leu Glu Ile Gln Arg Asp
305                 310                 315                 320

Glu Leu Pro Thr Glu Leu Pro Asp Leu Ala Val Asp Phe Val Glu Asp
                325                 330                 335

Lys Glu Val Cys Lys Asn Phe Ala Glu Ala Lys Asp Val Phe Leu Gly
            340                 345                 350

Thr Phe Leu Tyr Glu Tyr Ser Arg Arg His Pro Glu Tyr Ser Ile Gly
        355                 360                 365

Met Leu Leu Arg Ile Ala Lys Gly Tyr Glu Ala Lys Leu Glu Lys Cys
    370                 375                 380

Cys Ala Glu Ala Asp Pro His Ala Cys Tyr Ala Lys Val Phe Asp Glu
385                 390                 395                 400

Leu Gln Pro Leu Ile Asp Glu Pro Lys Lys Leu Val Gln Gln Asn Cys
                405                 410                 415

Glu Leu Phe Asp Lys Leu Gly Glu Tyr Gly Phe Gln Asn Ala Leu Ala
            420                 425                 430

Val Arg Tyr Thr Gln Lys Ala Pro Gln Val Ser Thr Pro Thr Leu Val
        435                 440                 445

Glu Tyr Ala Arg Lys Leu Gly Ser Val Gly Thr Lys Cys Cys Ser Leu
    450                 455                 460

Pro Glu Thr Glu Arg Leu Ser Cys Thr Glu Asn Tyr Leu Ala Leu Ile
465                 470                 475                 480

Leu Asn Arg Leu Cys Ile Leu His Glu Lys Thr Pro Val Ser Glu Arg
                485                 490                 495

Val Thr Lys Cys Cys Thr Glu Ser Leu Val Asn Arg Arg Pro Cys Phe
            500                 505                 510

Ser Ala Leu His Val Asp Glu Thr Tyr Val Pro Lys Pro Phe His Ala
        515                 520                 525

Asp Ser Phe Thr Phe His Ala Asp Ile Cys Thr Leu Pro Glu Lys Glu
    530                 535                 540

Lys Gln Val Lys Lys Gln Met Ala Leu Val Glu Leu Val Lys His Lys
545                 550                 555                 560

Pro Lys Ala Ser Glu Glu Gln Met Lys Thr Val Met Gly Asp Phe Ala
                565                 570                 575

Ala Phe Leu Lys Lys Cys Cys Asp Ala Asp Asn Lys Glu Ala Cys Phe
            580                 585                 590

Thr Glu Asp Gly Pro Lys Leu Val Ala Lys Cys Gln Ala Thr Leu Ala
        595                 600                 605

<210> SEQ ID NO 8
<211> LENGTH: 608
<212> TYPE: PRT
<213> ORGANISM: Mus musculus

<400> SEQUENCE: 8

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

```
His Arg Tyr Asn Asp Leu Gly Glu Gln His Phe Lys Gly Leu Val Leu
         35                  40                  45

Ile Ala Phe Ser Gln Tyr Leu Gln Lys Cys Ser Tyr Asp Glu His Ala
 50                  55                  60

Lys Leu Val Gln Glu Val Thr Asp Phe Ala Lys Thr Cys Val Ala Asp
 65                  70                  75                  80

Glu Ser Ala Ala Asn Cys Asp Lys Ser Leu His Thr Leu Phe Gly Asp
                 85                  90                  95

Lys Leu Cys Ala Ile Pro Asn Leu Arg Glu Asn Tyr Gly Glu Leu Ala
                100                 105                 110

Asp Cys Cys Thr Lys Gln Glu Pro Glu Arg Asn Glu Cys Phe Leu Gln
                115                 120                 125

His Lys Asp Asp Asn Pro Ser Leu Pro Pro Phe Glu Arg Pro Glu Ala
    130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
            180                 185                 190

Cys Ala Glu Ala Asp Lys Glu Ser Cys Leu Thr Pro Lys Leu Asp Gly
            195                 200                 205

Val Lys Glu Lys Ala Leu Val Ser Ser Val Arg Gln Arg Met Lys Cys
    210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
                260                 265                 270

Asp Leu Leu Glu Cys Ala Asp Asp Arg Ala Glu Leu Ala Lys Tyr Met
            275                 280                 285

Cys Glu Asn Gln Ala Thr Ile Ser Ser Lys Leu Gln Thr Cys Cys Asp
    290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
            355                 360                 365

Leu Leu Leu Arg Leu Ala Lys Lys Tyr Glu Ala Thr Leu Glu Lys Cys
    370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
            420                 425                 430

Val Arg Tyr Thr Gln Lys Ala Pro Gln Val Ser Thr Pro Thr Leu Val
    435                 440                 445
```

```
Glu Ala Ala Arg Asn Leu Gly Arg Val Gly Thr Lys Cys Cys Thr Leu
    450                 455                 460
Pro Glu Asp Gln Arg Leu Pro Cys Val Glu Asp Tyr Leu Ser Ala Ile
465                 470                 475                 480
Leu Asn Arg Val Cys Leu Leu His Glu Lys Thr Pro Val Ser Glu His
                485                 490                 495
Val Thr Lys Cys Cys Ser Gly Ser Leu Val Glu Arg Arg Pro Cys Phe
            500                 505                 510
Ser Ala Leu Thr Val Asp Glu Thr Tyr Val Pro Lys Glu Phe Lys Ala
        515                 520                 525
Glu Thr Phe Thr Phe His Ser Asp Ile Cys Thr Leu Pro Glu Lys Glu
    530                 535                 540
Lys Gln Ile Lys Lys Gln Thr Ala Leu Ala Glu Leu Val Lys His Lys
545                 550                 555                 560
Pro Lys Ala Thr Ala Glu Gln Leu Lys Thr Val Met Asp Asp Phe Ala
                565                 570                 575
Gln Phe Leu Asp Thr Cys Cys Lys Ala Ala Asp Lys Asp Thr Cys Phe
            580                 585                 590
Ser Thr Glu Gly Pro Asn Leu Val Thr Arg Cys Lys Asp Ala Leu Ala
        595                 600                 605

<210> SEQ ID NO 9
<211> LENGTH: 608
<212> TYPE: PRT
<213> ORGANISM: Rattus norvegicus

<400> SEQUENCE: 9

Met Lys Trp Val Thr Phe Leu Leu Leu Leu Phe Ile Ser Gly Ser Ala
1               5                   10                  15
Phe Ser Arg Gly Val Phe Arg Arg Glu Ala His Lys Ser Glu Ile Ala
            20                  25                  30
His Arg Phe Lys Asp Leu Gly Glu Gln His Phe Lys Gly Leu Val Leu
        35                  40                  45
Ile Ala Phe Ser Gln Tyr Leu Gln Lys Cys Pro Tyr Glu Glu His Ile
    50                  55                  60
Lys Leu Val Gln Glu Val Thr Asp Phe Ala Lys Thr Cys Val Ala Asp
65                  70                  75                  80
Glu Asn Ala Glu Asn Cys Asp Lys Ser Ile His Thr Leu Phe Gly Asp
                85                  90                  95
Lys Leu Cys Ala Ile Pro Lys Leu Arg Asp Asn Tyr Gly Glu Leu Ala
            100                 105                 110
Asp Cys Cys Ala Lys Gln Glu Pro Glu Arg Asn Glu Cys Phe Leu Gln
        115                 120                 125
His Lys Asp Asp Asn Pro Asn Leu Pro Pro Phe Gln Arg Pro Glu Ala
    130                 135                 140
Glu Ala Met Cys Thr Ser Phe Gln Glu Asn Pro Thr Ser Phe Leu Gly
145                 150                 155                 160
His Tyr Leu His Glu Val Ala Arg Arg His Pro Tyr Phe Tyr Ala Pro
                165                 170                 175
Glu Leu Leu Tyr Tyr Ala Glu Lys Tyr Asn Glu Val Leu Thr Gln Cys
            180                 185                 190
Cys Thr Glu Ser Asp Lys Ala Ala Cys Leu Thr Pro Lys Leu Asp Ala
        195                 200                 205
Val Lys Glu Lys Ala Leu Val Ala Ala Val Arg Gln Arg Met Lys Cys
    210                 215                 220
```

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
            245                 250                 255

Lys Leu Ala Thr Asp Val Thr Lys Ile Asn Lys Glu Cys Cys His Gly
        260                 265                 270

Asp Leu Leu Glu Cys Ala Asp Asp Arg Ala Glu Leu Ala Lys Tyr Met
    275                 280                 285

Cys Glu Asn Gln Ala Thr Ile Ser Ser Lys Leu Gln Ala Cys Cys Asp
290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ser Arg Arg His Pro Asp Tyr Ser Val Ser
        355                 360                 365

Leu Leu Leu Arg Leu Ala Lys Lys Tyr Glu Ala Thr Leu Glu Lys Cys
370                 375                 380

Cys Ala Glu Gly Asp Pro Pro Ala Cys Tyr Gly Thr Val Leu Ala Glu
385                 390                 395                 400

Phe Gln Pro Leu Val Glu Pro Lys Asn Leu Val Lys Thr Asn Cys
                405                 410                 415

Glu Leu Tyr Glu Lys Leu Gly Glu Tyr Gly Phe Gln Asn Ala Val Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Asp Lys Glu
        530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
            580                 585                 590

Ala Thr Glu Gly Pro Asn Leu Val Ala Arg Ser Lys Glu Ala Leu Ala
        595                 600                 605

<210> SEQ ID NO 10
<211> LENGTH: 607
<212> TYPE: PRT
<213> ORGANISM: Bos taurus

```
<400> SEQUENCE: 10

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415
```

```
Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
        530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
                580                 585                 590

Val Glu Gly Pro Lys Leu Val Val Ser Thr Gln Thr Ala Leu Ala
            595                 600                 605

<210> SEQ ID NO 11
<211> LENGTH: 607
<212> TYPE: PRT
<213> ORGANISM: Equus caballus

<400> SEQUENCE: 11

Met Lys Trp Val Thr Phe Val Ser Leu Leu Phe Leu Phe Ser Ser Ala
1               5                   10                  15

Tyr Ser Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
```

```
                180             185             190
Pro Ala Asp Asp Lys Leu Ala Cys Leu Ile Pro Lys Leu Asp Ala Leu
            195                 200                 205
Lys Glu Arg Ile Leu Leu Ser Ser Ala Lys Glu Arg Leu Lys Cys Ser
    210                 215                 220
Ser Phe Gln Asn Phe Gly Glu Arg Ala Val Lys Ala Trp Ser Val Ala
225                 230                 235                 240
Arg Leu Ser Gln Lys Phe Pro Lys Ala Asp Phe Ala Glu Val Ser Lys
                245                 250                 255
Ile Val Thr Asp Leu Thr Lys Val His Lys Glu Cys Cys His Gly Asp
            260                 265                 270
Leu Leu Glu Cys Ala Asp Asp Arg Ala Asp Leu Ala Lys Tyr Ile Cys
        275                 280                 285
Glu His Gln Asp Ser Ile Ser Gly Lys Leu Lys Ala Cys Cys Asp Lys
    290                 295                 300
Pro Leu Leu Gln Lys Ser His Cys Ile Ala Glu Val Lys Glu Asp Asp
305                 310                 315                 320
Leu Pro Ser Asp Leu Pro Ala Leu Ala Ala Asp Phe Ala Glu Asp Lys
                325                 330                 335
Glu Ile Cys Lys His Tyr Lys Asp Ala Lys Asp Val Phe Leu Gly Thr
            340                 345                 350
Phe Leu Tyr Glu Tyr Ser Arg Arg His Pro Asp Tyr Ser Val Ser Leu
        355                 360                 365
Leu Leu Arg Ile Ala Lys Thr Tyr Glu Ala Thr Leu Glu Lys Cys Cys
    370                 375                 380
Ala Glu Ala Asp Pro Pro Ala Cys Tyr Arg Thr Val Phe Asp Gln Phe
385                 390                 395                 400
Thr Pro Leu Val Glu Glu Pro Lys Ser Leu Val Lys Lys Asn Cys Asp
                405                 410                 415
Leu Phe Glu Glu Val Gly Glu Tyr Asp Phe Gln Asn Ala Leu Ile Val
            420                 425                 430
Arg Tyr Thr Lys Lys Ala Pro Gln Val Ser Thr Pro Thr Leu Val Glu
        435                 440                 445
Ile Gly Arg Thr Leu Gly Lys Val Gly Ser Arg Cys Cys Lys Leu Pro
    450                 455                 460
Glu Ser Glu Arg Leu Pro Cys Ser Glu Asn His Leu Ala Leu Ala Leu
465                 470                 475                 480
Asn Arg Leu Cys Val Leu His Glu Lys Thr Pro Val Ser Glu Lys Ile
                485                 490                 495
Thr Lys Cys Cys Thr Asp Ser Leu Ala Glu Arg Arg Pro Cys Phe Ser
            500                 505                 510
Ala Leu Glu Leu Asp Glu Gly Tyr Val Pro Lys Glu Phe Lys Ala Glu
        515                 520                 525
Thr Phe Thr Phe His Ala Asp Ile Cys Thr Leu Pro Glu Asp Glu Lys
    530                 535                 540
Gln Ile Lys Lys Gln Ser Ala Leu Ala Glu Leu Val Lys His Lys Pro
545                 550                 555                 560
Lys Ala Thr Lys Glu Gln Leu Lys Thr Val Leu Gly Asn Phe Ser Ala
                565                 570                 575
Phe Val Ala Lys Cys Cys Gly Arg Glu Asp Lys Glu Ala Cys Phe Ala
            580                 585                 590
Glu Glu Gly Pro Lys Leu Val Ala Ser Ser Gln Leu Ala Leu Ala
        595                 600                 605
```

<210> SEQ ID NO 12
<211> LENGTH: 607
<212> TYPE: PRT
<213> ORGANISM: Equus asinus

<400> SEQUENCE: 12

```
Met Lys Trp Val Thr Phe Val Ser Leu Leu Phe Leu Phe Ser Ser Ala
1               5                   10                  15

Tyr Phe Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Ala Gly Cys Leu Ile Pro Lys Leu Asp Ala Leu
        195                 200                 205

Lys Glu Arg Ile Leu Leu Ser Ser Ala Lys Glu Arg Leu Lys Cys Ser
    210                 215                 220

Ser Phe Gln Lys Phe Gly Glu Arg Ala Phe Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Thr Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Thr Tyr Glu Ala Thr Leu Glu Lys Cys Cys
```

```
                370             375             380
Ala Glu Ala Asp Pro Pro Ala Cys Tyr Ala Thr Val Phe Asp Gln Phe
385             390             395             400

Thr Pro Leu Val Glu Glu Pro Lys Ser Leu Val Lys Lys Asn Cys Asp
                405             410             415

Leu Phe Glu Glu Val Gly Glu Tyr Asp Phe Gln Asn Ala Leu Ile Val
            420             425             430

Arg Tyr Thr Lys Lys Ala Pro Gln Val Ser Thr Pro Thr Leu Val Glu
        435             440             445

Ile Gly Arg Thr Leu Gly Lys Val Gly Ser Arg Cys Cys Lys Leu Pro
    450             455             460

Glu Ser Glu Arg Leu Pro Cys Ser Glu Asn His Leu Ala Leu Ala Leu
465             470             475             480

Asn Arg Leu Cys Val Leu His Glu Lys Thr Pro Val Ser Glu Lys Ile
                485             490             495

Thr Lys Cys Cys Thr Asp Ser Leu Ala Glu Arg Arg Pro Cys Phe Ser
            500             505             510

Ala Leu Glu Leu Asp Glu Gly Tyr Ile Pro Lys Glu Phe Lys Ala Glu
        515             520             525

Thr Phe Thr Phe His Ala Asp Ile Cys Thr Leu Pro Glu Asp Glu Lys
    530             535             540

Gln Ile Lys Lys Gln Ser Ala Leu Ala Glu Leu Val Lys His Lys Pro
545             550             555             560

Lys Ala Thr Lys Glu Gln Leu Lys Thr Val Leu Gly Asn Phe Ser Ala
                565             570             575

Phe Val Ala Lys Cys Cys Gly Ala Glu Asp Lys Glu Ala Cys Phe Ala
            580             585             590

Glu Glu Gly Pro Lys Leu Val Ala Ser Ser Gln Leu Ala Leu Ala
        595             600             605

<210> SEQ ID NO 13
<211> LENGTH: 608
<212> TYPE: PRT
<213> ORGANISM: Oryctolagus cuniculus

<400> SEQUENCE: 13

Met Lys Trp Val Thr Phe Ile Ser Leu Leu Phe Leu Phe Ser Ser Ala
1               5                   10                  15

Tyr Ser Arg Gly Val Phe Arg Arg Glu Ala His Lys Ser Glu Ile Ala
            20                  25                  30

His Arg Phe Asn Asp Val Gly Glu His Phe Ile Gly Leu Val Leu
            35                  40                  45

Ile Thr Phe Ser Gln Tyr Leu Gln Lys Cys Pro Tyr Glu Glu His Ala
    50                  55                  60

Lys Leu Val Lys Glu Val Thr Asp Leu Ala Lys Ala Cys Val Ala Asp
65                  70                  75                  80

Glu Ser Ala Ala Asn Cys Asp Lys Ser Leu His Asp Ile Phe Gly Asp
                85                  90                  95

Lys Ile Cys Ala Leu Pro Ser Leu Arg Asp Thr Tyr Gly Asp Val Ala
            100                 105                 110

Asp Cys Cys Glu Lys Lys Glu Pro Glu Arg Asn Glu Cys Phe Leu His
        115                 120                 125

His Lys Asp Asp Lys Pro Asp Leu Pro Pro Phe Ala Arg Pro Glu Ala
    130                 135                 140
```

```
Asp Val Leu Cys Lys Ala Phe His Asp Asp Glu Lys Ala Phe Phe Gly
145                 150                 155                 160

His Tyr Leu Tyr Glu Val Ala Arg Arg His Pro Tyr Phe Tyr Ala Pro
            165                 170                 175

Glu Leu Leu Tyr Tyr Ala Gln Lys Tyr Lys Ala Ile Leu Thr Glu Cys
                180                 185                 190

Cys Glu Ala Ala Asp Lys Gly Ala Cys Leu Thr Pro Lys Leu Asp Ala
        195                 200                 205

Leu Glu Gly Lys Ser Leu Ile Ser Ala Ala Gln Glu Arg Leu Arg Cys
        210                 215                 220

Ala Ser Ile Gln Lys Phe Gly Asp Arg Ala Tyr Lys Ala Trp Ala Leu
225                 230                 235                 240

Val Arg Leu Ser Gln Arg Phe Pro Lys Ala Asp Phe Thr Asp Ile Ser
                245                 250                 255

Lys Ile Val Thr Asp Leu Thr Lys Val His Lys Glu Cys Cys His Gly
                260                 265                 270

Asp Leu Leu Glu Cys Ala Asp Asp Arg Ala Asp Leu Ala Lys Tyr Met
            275                 280                 285

Cys Glu His Gln Glu Thr Ile Ser Ser His Leu Lys Glu Cys Cys Asp
        290                 295                 300

Lys Pro Ile Leu Glu Lys Ala His Cys Ile Tyr Gly Leu His Asn Asp
305                 310                 315                 320

Glu Thr Pro Ala Gly Leu Pro Ala Val Ala Glu Phe Val Glu Asp
                325                 330                 335

Lys Asp Val Cys Lys Asn Tyr Glu Glu Ala Lys Asp Leu Phe Leu Gly
            340                 345                 350

Lys Phe Leu Tyr Glu Tyr Ser Arg Arg His Pro Asp Tyr Ser Val Val
        355                 360                 365

Leu Leu Leu Arg Leu Gly Lys Ala Tyr Glu Ala Thr Leu Lys Lys Cys
        370                 375                 380

Cys Ala Thr Asp Asp Pro His Ala Cys Tyr Ala Lys Val Leu Asp Glu
385                 390                 395                 400

Phe Gln Pro Leu Val Asp Glu Pro Lys Asn Leu Val Lys Gln Asn Cys
                405                 410                 415

Glu Leu Tyr Glu Gln Leu Gly Asp Tyr Asn Phe Gln Asn Ala Leu Leu
            420                 425                 430

Val Arg Tyr Thr Lys Lys Val Pro Gln Val Ser Thr Pro Thr Leu Val
            435                 440                 445

Glu Ile Ser Arg Ser Leu Gly Lys Val Gly Ser Lys Cys Cys Lys His
450                 455                 460

Pro Glu Ala Glu Arg Leu Pro Cys Val Glu Asp Tyr Leu Ser Val Val
465                 470                 475                 480

Leu Asn Arg Leu Cys Val Leu His Glu Lys Thr Pro Val Ser Glu Lys
            485                 490                 495

Val Thr Lys Cys Cys Ser Glu Ser Leu Val Asp Arg Arg Pro Cys Phe
                500                 505                 510

Ser Ala Leu Gly Pro Asp Glu Thr Tyr Val Pro Lys Glu Phe Asn Ala
            515                 520                 525

Glu Thr Phe Thr Phe His Ala Asp Ile Cys Thr Leu Pro Glu Thr Glu
            530                 535                 540

Arg Lys Ile Lys Lys Gln Thr Ala Leu Val Glu Leu Val Lys His Lys
545                 550                 555                 560

Pro His Ala Thr Asn Asp Gln Leu Lys Thr Val Val Gly Glu Phe Thr
```

-continued

```
                565                 570                 575
Ala Leu Leu Asp Lys Cys Cys Ser Ala Glu Asp Lys Glu Ala Cys Phe
                580                 585                 590

Ala Val Glu Gly Pro Lys Leu Val Glu Ser Ser Lys Ala Thr Leu Gly
                595                 600                 605

<210> SEQ ID NO 14
<211> LENGTH: 583
<212> TYPE: PRT
<213> ORGANISM: Capra hircus

<400> SEQUENCE: 14

Asp Thr His Lys Ser Glu Ile Ala His Arg Phe Asn Asp Leu Gly Glu
  1               5                  10                  15

Glu Asn Phe Gln Gly Leu Val Leu Ile Ala Phe Ser Gln Tyr Leu Gln
                 20                  25                  30

Gln Cys Pro Phe Asp Glu His Val Lys Leu Val Lys Glu Leu Thr Glu
             35                  40                  45

Phe Ala Lys Thr Cys Val Ala Asp Glu Ser His Ala Gly Cys Asp Lys
         50                  55                  60

Ser Leu His Thr Leu Phe Gly Asp Glu Leu Cys Lys Val Ala Thr Leu
 65                  70                  75                  80

Arg Glu Thr Tyr Gly Asp Met Ala Asp Cys Cys Glu Lys Gln Glu Pro
                 85                  90                  95

Glu Arg Asn Glu Cys Phe Leu Lys His Lys Asp Asp Ser Pro Asp Leu
            100                 105                 110

Pro Lys Leu Lys Pro Glu Pro Asp Thr Leu Cys Ala Glu Phe Lys Ala
        115                 120                 125

Asp Glu Lys Lys Phe Trp Gly Lys Tyr Leu Tyr Glu Val Ala Arg Arg
    130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Ala Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
    210                 215                 220

Ala Asp Phe Thr Asp Val Thr Lys Ile Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp His Gln Asp Thr Leu Ser Ser
            260                 265                 270

Lys Leu Lys Glu Cys Cys Asp Lys Pro Val Leu Glu Lys Ser His Cys
        275                 280                 285

Ile Ala Glu Ile Asp Lys Asp Ala Val Pro Glu Asn Leu Pro Pro Leu
    290                 295                 300

Thr Ala Asp Phe Ala Glu Asp Lys Glu Val Cys Lys Asn Tyr Gln Glu
305                 310                 315                 320

Ala Lys Asp Val Phe Leu Gly Ser Phe Leu Tyr Glu Tyr Ser Arg Arg
                325                 330                 335
```

```
His Pro Glu Tyr Ala Val Ser Val Leu Leu Arg Leu Ala Lys Glu Tyr
            340                 345                 350

Glu Ala Thr Leu Glu Asp Cys Cys Ala Lys Glu Asp Pro His Ala Cys
        355                 360                 365

Tyr Ala Thr Val Phe Asp Lys Leu Lys His Leu Val Asp Glu Pro Gln
        370                 375                 380

Asn Leu Ile Lys Lys Asn Cys Glu Leu Phe Glu Lys His Gly Glu Tyr
385                 390                 395                 400

Gly Phe Gln Asn Ala Leu Ile Val Arg Tyr Thr Arg Lys Ala Pro Gln
                405                 410                 415

Val Ser Thr Pro Thr Leu Val Glu Ile Ser Arg Ser Leu Gly Lys Val
            420                 425                 430

Gly Thr Lys Cys Cys Ala Lys Pro Glu Ser Glu Arg Met Pro Cys Thr
        435                 440                 445

Glu Asp Tyr Leu Ser Leu Ile Leu Asn Arg Leu Cys Val Leu His Glu
        450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Asp Leu Thr Leu Asp Glu Thr Tyr
                485                 490                 495

Val Pro Lys Pro Phe Asp Gly Glu Ser Phe Thr Phe His Ala Asp Ile
            500                 505                 510

Cys Thr Leu Pro Asp Thr Glu Lys Gln Ile Lys Lys Gln Thr Ala Leu
        515                 520                 525

Val Glu Leu Leu Lys His Lys Pro Lys Ala Thr Asp Glu Gln Leu Lys
    530                 535                 540

Thr Val Met Glu Asn Phe Val Ala Phe Val Asp Lys Cys Cys Ala Ala
545                 550                 555                 560

Asp Asp Lys Glu Gly Cys Phe Leu Leu Glu Gly Pro Lys Leu Val Ala
                565                 570                 575

Ser Thr Gln Ala Ala Leu Ala
            580

<210> SEQ ID NO 15
<211> LENGTH: 607
<212> TYPE: PRT
<213> ORGANISM: Ovis aries

<400> SEQUENCE: 15

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Asn Asp Leu Gly Glu Glu Asn Phe Gln Gly Leu Val Leu
        35                  40                  45

Ile Ala Phe Ser Gln Tyr Leu Gln Gln Cys Pro Phe Asp Glu His Val
    50                  55                  60

Lys Leu Val Lys Glu Leu Thr Glu Phe Ala Lys Thr Cys Val Ala Asp
65                  70                  75                  80

Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
            100                 105                 110

Asp Cys Cys Glu Lys Gln Glu Pro Glu Arg Asn Glu Cys Phe Leu Asn
        115                 120                 125
```

```
His Lys Asp Asp Ser Pro Asp Leu Pro Lys Leu Lys Pro Glu Pro Asp
        130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
            165                 170                 175

Leu Leu Tyr Tyr Ala Asn Lys Tyr Asn Gly Val Phe Gln Glu Cys Cys
                180                 185                 190

Gln Ala Glu Asp Lys Gly Ala Cys Leu Leu Pro Lys Ile Asp Ala Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Asp Phe Thr Asp Val Thr Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
                275                 280                 285

Asp His Gln Asp Ala Leu Ser Ser Lys Leu Lys Glu Cys Cys Asp Lys
        290                 295                 300

Pro Val Leu Glu Lys Ser His Cys Ile Ala Glu Val Asp Lys Asp Ala
305                 310                 315                 320

Val Pro Glu Asn Leu Pro Pro Leu Thr Ala Asp Phe Ala Glu Asp Lys
                325                 330                 335

Glu Val Cys Lys Asn Tyr Gln Glu Ala Lys Asp Val Phe Leu Gly Ser
            340                 345                 350

Phe Leu Tyr Glu Tyr Ser Arg Arg His Pro Glu Tyr Ala Val Ser Val
                355                 360                 365

Leu Leu Arg Leu Ala Lys Glu Tyr Glu Ala Thr Leu Glu Asp Cys Cys
        370                 375                 380

Ala Lys Glu Asp Pro His Ala Cys Tyr Ala Thr Val Phe Asp Lys Leu
385                 390                 395                 400

Lys His Leu Val Asp Glu Pro Gln Asn Leu Ile Lys Lys Asn Cys Glu
                405                 410                 415

Leu Phe Glu Lys His Gly Glu Tyr Gly Phe Gln Asn Ala Leu Ile Val
            420                 425                 430

Arg Tyr Thr Arg Lys Ala Pro Gln Val Ser Thr Pro Thr Leu Val Glu
        435                 440                 445

Ile Ser Arg Ser Leu Gly Lys Val Gly Thr Lys Cys Cys Ala Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Asp Leu Thr Leu Asp Glu Thr Tyr Val Pro Lys Pro Phe Asp Glu Lys
        515                 520                 525

Phe Phe Thr Phe His Ala Asp Ile Cys Thr Leu Pro Asp Thr Glu Lys
530                 535                 540
```

```
Gln Ile Lys Lys Gln Thr Ala Leu Val Glu Leu Leu Lys His Lys Pro
545                 550                 555                 560

Lys Ala Thr Asp Glu Gln Leu Lys Thr Val Met Glu Asn Phe Val Ala
            565                 570                 575

Phe Val Asp Lys Cys Cys Ala Ala Asp Asp Lys Glu Gly Cys Phe Val
        580                 585                 590

Leu Glu Gly Pro Lys Leu Val Ala Ser Thr Gln Ala Ala Leu Ala
        595                 600                 605
```

<210> SEQ ID NO 16
<211> LENGTH: 608
<212> TYPE: PRT
<213> ORGANISM: canis lupus familiaris

<400> SEQUENCE: 16

```
Met Lys Trp Val Thr Phe Ile Ser Leu Phe Phe Leu Phe Ser Ser Ala
1               5                   10                  15

Tyr Ser Arg Gly Leu Val Arg Arg Glu Ala Tyr Lys Ser Glu Ile Ala
            20                  25                  30

His Arg Tyr Asn Asp Leu Gly Glu Glu His Phe Arg Gly Leu Val Leu
        35                  40                  45

Val Ala Phe Ser Gln Tyr Leu Gln Gln Cys Pro Phe Glu Asp His Val
50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
                85                  90                  95

Lys Leu Cys Thr Val Ala Ser Leu Arg Asp Lys Tyr Gly Asp Met Ala
            100                 105                 110

Asp Cys Cys Glu Lys Gln Glu Pro Asp Arg Asn Glu Cys Phe Leu Ala
        115                 120                 125

His Lys Asp Asp Asn Pro Gly Phe Pro Pro Leu Val Ala Pro Glu Pro
    130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Gln Gln Tyr Lys Gly Val Phe Ala Glu Cys
            180                 185                 190

Cys Gln Ala Ala Asp Lys Ala Ala Cys Leu Gly Pro Lys Ile Glu Ala
        195                 200                 205

Leu Arg Glu Lys Val Leu Leu Ser Ser Ala Lys Glu Arg Phe Lys Cys
    210                 215                 220

Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
                245                 250                 255

Lys Val Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Thr Lys Leu Lys Glu Cys Cys Asp
    290                 295                 300

Lys Pro Val Leu Glu Lys Ser Gln Cys Leu Ala Glu Val Glu Arg Asp
305                 310                 315                 320
```

Glu Leu Pro Gly Asp Leu Pro Ser Leu Ala Ala Asp Phe Val Glu Asp
            325                 330                 335

Lys Glu Val Cys Lys Asn Tyr Gln Glu Ala Lys Asp Val Phe Leu Gly
        340                 345                 350

Thr Phe Leu Tyr Glu Tyr Ala Arg Arg His Pro Glu Tyr Ser Val Ser
            355                 360                 365

Leu Leu Leu Arg Leu Ala Lys Glu Tyr Glu Ala Thr Leu Glu Lys Cys
        370                 375                 380

Cys Ala Thr Asp Asp Pro Pro Thr Cys Tyr Ala Lys Val Leu Asp Glu
385                 390                 395                 400

Phe Lys Pro Leu Val Asp Glu Pro Gln Asn Leu Val Lys Thr Asn Cys
            405                 410                 415

Glu Leu Phe Glu Lys Leu Gly Glu Tyr Gly Phe Gln Asn Ala Leu Leu
        420                 425                 430

Val Arg Tyr Thr Lys Lys Ala Pro Gln Val Ser Thr Pro Thr Leu Val
            435                 440                 445

Glu Val Ser Arg Lys Leu Gly Lys Val Gly Thr Lys Cys Cys Lys Lys
        450                 455                 460

Pro Glu Ser Glu Arg Met Ser Cys Ala Glu Asp Phe Leu Ser Val Val
465                 470                 475                 480

Leu Asn Arg Leu Cys Val Leu His Glu Lys Thr Pro Val Ser Glu Arg
            485                 490                 495

Val Thr Lys Cys Cys Ser Glu Ser Leu Val Asn Arg Arg Pro Cys Phe
        500                 505                 510

Ser Gly Leu Glu Val Asp Glu Thr Tyr Val Pro Lys Glu Phe Asn Ala
            515                 520                 525

Glu Thr Phe Thr Phe His Ala Asp Leu Cys Thr Leu Pro Glu Ala Glu
        530                 535                 540

Lys Gln Val Lys Gln Thr Ala Leu Val Glu Leu Lys His Lys
545                 550                 555                 560

Pro Lys Ala Thr Asp Glu Gln Leu Lys Thr Val Met Gly Asp Phe Gly
            565                 570                 575

Ala Phe Val Glu Lys Cys Cys Ala Ala Glu Asn Lys Glu Gly Cys Phe
        580                 585                 590

Ser Glu Glu Gly Pro Lys Leu Val Ala Ala Gln Ala Ala Leu Val
            595                 600                 605

<210> SEQ ID NO 17
<211> LENGTH: 615
<212> TYPE: PRT
<213> ORGANISM: Gallus gallus

<400> SEQUENCE: 17

Met Lys Trp Val Thr Leu Ile Ser Phe Ile Phe Leu Phe Ser Ser Ala
1               5                   10                  15

Thr Ser Arg Asn Leu Gln Arg Phe Ala Arg Asp Ala Glu His Lys Ser
            20                  25                  30

Glu Ile Ala His Arg Tyr Asn Asp Leu Lys Glu Glu Thr Phe Lys Ala
        35                  40                  45

Val Ala Met Ile Thr Phe Ala Gln Tyr Leu Gln Arg Cys Ser Tyr Glu
    50                  55                  60

Gly Leu Ser Lys Leu Val Lys Asp Val Val Asp Leu Ala Gln Lys Cys
65                  70                  75                  80

Val Ala Asn Glu Asp Ala Pro Glu Cys Ser Lys Pro Leu Pro Ser Ile

```
                     85                  90                  95
Ile Leu Asp Glu Ile Cys Gln Val Glu Lys Leu Arg Asp Ser Tyr Gly
                100                 105                 110

Ala Met Ala Asp Cys Cys Ser Lys Ala Asp Pro Glu Arg Asn Glu Cys
                115                 120                 125

Phe Leu Ser Phe Lys Val Ser Gln Pro Asp Phe Val Gln Pro Tyr Gln
            130                 135                 140

Arg Pro Ala Ser Asp Val Ile Cys Gln Glu Tyr Gln Asp Asn Arg Val
145                 150                 155                 160

Ser Phe Leu Gly His Phe Ile Tyr Ser Val Ala Arg Arg His Pro Phe
                165                 170                 175

Leu Tyr Ala Pro Ala Ile Leu Ser Phe Ala Val Asp Phe Glu His Ala
                180                 185                 190

Leu Gln Ser Cys Cys Lys Glu Ser Asp Val Gly Ala Cys Leu Asp Thr
                195                 200                 205

Lys Glu Ile Val Met Arg Glu Lys Ala Lys Gly Val Ser Val Lys Gln
            210                 215                 220

Gln Tyr Phe Cys Gly Ile Leu Lys Gln Phe Gly Asp Arg Val Phe Gln
225                 230                 235                 240

Ala Arg Gln Leu Ile Tyr Leu Ser Gln Lys Tyr Pro Lys Ala Pro Phe
                245                 250                 255

Ser Glu Val Ser Lys Phe Val His Asp Ser Ile Gly Val His Lys Glu
                260                 265                 270

Cys Cys Glu Gly Asp Met Val Glu Cys Met Asp Asp Met Ala Arg Met
            275                 280                 285

Met Ser Asn Leu Cys Ser Gln Gln Asp Val Phe Ser Gly Lys Ile Lys
            290                 295                 300

Asp Cys Cys Glu Lys Pro Ile Val Glu Arg Ser Gln Cys Ile Met Glu
305                 310                 315                 320

Ala Glu Phe Asp Glu Lys Pro Ala Asp Leu Pro Ser Leu Val Glu Lys
                325                 330                 335

Tyr Ile Glu Asp Lys Glu Val Cys Lys Ser Phe Glu Ala Gly His Asp
                340                 345                 350

Ala Phe Met Ala Glu Phe Val Tyr Glu Tyr Ser Arg Arg His Pro Glu
            355                 360                 365

Phe Ser Ile Gln Leu Ile Met Arg Ile Ala Lys Gly Tyr Glu Ser Leu
            370                 375                 380

Leu Glu Lys Cys Cys Lys Thr Asp Asn Pro Ala Glu Cys Tyr Ala Asn
385                 390                 395                 400

Ala Gln Glu Gln Leu Asn Gln His Ile Lys Glu Thr Gln Asp Val Val
                405                 410                 415

Lys Thr Asn Cys Asp Leu Leu His Asp His Gly Glu Ala Asp Phe Leu
                420                 425                 430

Lys Ser Ile Leu Ile Arg Tyr Thr Lys Lys Met Pro Gln Val Pro Thr
            435                 440                 445

Asp Leu Leu Leu Glu Thr Gly Lys Lys Met Thr Thr Ile Gly Thr Lys
450                 455                 460

Cys Cys Gln Leu Gly Glu Asp Arg Arg Met Ala Cys Ser Glu Gly Tyr
465                 470                 475                 480

Leu Ser Ile Val Ile His Asp Thr Cys Arg Lys Gln Glu Thr Thr Pro
                485                 490                 495

Ile Asn Asp Asn Val Ser Gln Cys Cys Ser Gln Leu Tyr Ala Asn Arg
                500                 505                 510
```

```
Arg Pro Cys Phe Thr Ala Met Gly Val Asp Thr Lys Tyr Val Pro Pro
        515                 520                 525

Pro Phe Asn Pro Asp Met Phe Ser Phe Asp Glu Lys Leu Cys Ser Ala
    530                 535                 540

Pro Ala Glu Glu Arg Glu Val Gly Gln Met Lys Leu Leu Ile Asn Leu
545                 550                 555                 560

Ile Lys Arg Lys Pro Gln Met Thr Glu Gln Ile Lys Thr Ile Ala
            565                 570                 575

Asp Gly Phe Thr Ala Met Val Asp Lys Cys Cys Lys Gln Ser Asp Ile
                580                 585                 590

Asn Thr Cys Phe Gly Glu Gly Ala Asn Leu Ile Val Gln Ser Arg
            595                 600                 605

Ala Thr Leu Gly Ile Gly Ala
        610                 615

<210> SEQ ID NO 18
<211> LENGTH: 607
<212> TYPE: PRT
<213> ORGANISM: Sus scrofa

<400> SEQUENCE: 18

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Glu Pro Glu Arg Asn Glu Cys Phe Leu Gln
        115                 120                 125

His Lys Asn Asp Asn Pro Asp Ile Pro Lys Leu Lys Pro Asp Pro Val
    130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205

Arg Glu Lys Val Leu Thr Ser Ala Ala Lys Gln Arg Leu Lys Cys Ala
    210                 215                 220

Ser Ile Gln Lys Phe Gly Glu Arg Ala Phe Lys Ala Trp Ser Leu Ala
225                 230                 235                 240

Arg Leu Ser Gln Arg Phe Pro Lys Ala Asp Phe Thr Glu Ile Ser Lys
                245                 250                 255

Ile Val Thr Asp Leu Ala Lys Val His Lys Glu Cys Cys His Gly Asp
```

```
                    260                 265                 270
Leu Leu Glu Cys Ala Asp Asp Arg Ala Asp Leu Ala Lys Tyr Ile Cys
            275                 280                 285

Glu Asn Gln Asp Thr Ile Ser Thr Lys Leu Lys Glu Cys Cys Asp Lys
        290                 295                 300

Pro Leu Leu Glu Lys Ser His Cys Ile Ala Glu Ala Lys Arg Asp Glu
305                 310                 315                 320

Leu Pro Ala Asp Leu Asn Pro Leu Glu His Asp Phe Val Glu Asp Lys
                325                 330                 335

Glu Val Cys Lys Asn Tyr Lys Glu Ala Lys His Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Ile Tyr Glu Ala Thr Leu Glu Asp Cys Cys
    370                 375                 380

Ala Lys Glu Asp Pro Pro Ala Cys Tyr Ala Thr Val Phe Asp Lys Phe
385                 390                 395                 400

Gln Pro Leu Val Asp Glu Pro Lys Asn Leu Ile Lys Gln Asn Cys Glu
                405                 410                 415

Leu Phe Glu Lys Leu Gly Glu Tyr Gly Phe Gln Asn Ala Leu Ile Val
            420                 425                 430

Arg Tyr Thr Lys Lys Val Pro Gln Val Ser Thr Pro Thr Leu Val Glu
        435                 440                 445

Val Ala Arg Lys Leu Gly Leu Val Gly Ser Arg Cys Cys Lys Arg Pro
    450                 455                 460

Glu Glu Glu Arg Leu Ser Cys Ala Glu Asp Tyr Leu Ser Leu Val Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Lys Pro Lys Glu Phe Val Glu Gly
        515                 520                 525

Thr Phe Thr Phe His Ala Asp Leu Cys Thr Leu Pro Glu Asp Glu Lys
    530                 535                 540

Gln Ile Lys Lys Gln Thr Ala Leu Val Glu Leu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
            580                 585                 590

Val Glu Gly Pro Lys Phe Val Ile Glu Ile Arg Gly Ile Leu Ala
        595                 600                 605

<210> SEQ ID NO 19
<211> LENGTH: 584
<212> TYPE: PRT
<213> ORGANISM: Mus musculus

<400> SEQUENCE: 19

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30
```

```
Lys Cys Ser Tyr Asp Glu His Ala Lys Leu Val Gln Glu Val Thr Asp
            35                  40                  45

Phe Ala Lys Thr Cys Val Ala Asp Glu Ser Ala Ala Asn Cys Asp Lys
 50                  55                  60

Ser Leu His Thr Leu Phe Gly Asp Lys Leu Cys Ala Ile Pro Asn Leu
 65                  70                  75                  80

Arg Glu Asn Tyr Gly Glu Leu Ala Asp Cys Cys Thr Lys Gln Glu Pro
                 85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
            115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
            195                 200                 205

Arg Ala Phe Lys Ala Trp Ala Val Ala Arg Leu Ser Gln Thr Phe Pro
            210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
            275                 280                 285

Cys Leu Ser Glu Val Glu His Asp Thr Met Pro Ala Asp Leu Pro Ala
            290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
            355                 360                 365

Cys Tyr Gly Thr Val Leu Ala Glu Phe Gln Pro Leu Val Glu Glu Pro
370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
            435                 440                 445

Val Glu Asp Tyr Leu Ser Ala Ile Leu Asn Arg Val Cys Leu Leu His
```

```
                450                 455                 460
Glu Lys Thr Pro Val Ser Glu His Val Thr Lys Cys Cys Ser Gly Ser
465                     470                 475                 480

Leu Val Glu Arg Arg Pro Cys Phe Ser Ala Leu Thr Val Asp Glu Thr
            485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
        530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
            565                 570                 575

Thr Arg Cys Lys Asp Ala Leu Ala
            580
```